US012805760B2

(12) United States Patent
Pryor et al.

(10) Patent No.: US 12,805,760 B2
(45) Date of Patent: Nov. 24, 2026

(54) TRANSCUTANEOUS ANALYTE SENSORS, APPLICATORS THEREFOR, AND ASSOCIATED METHODS

(71) Applicant: DexCom, Inc., San Diego, CA (US)

(72) Inventors: Jack Pryor, Ladera Ranch, CA (US); Sebastian Böhm, San Diego, CA (US); David DeRenzy, San Diego, CA (US); Jason Halac, Solana Beach, CA (US); Daniel S. Kline, Encinitas, CA (US); Phong Lieu, San Diego, CA (US); Adam J. Livingston, Vista, CA (US); Steve Masterson, Encinitas, CA (US); Paul V. Neale, San Diego, CA (US); Peter C. Simpson, Cardiff, CA (US); Antonio Joao Ubach, Tucson, AZ (US)

(73) Assignee: Dexcom, Inc., San Diego, CA (US)

(*) Notice: Subject to any disclaimer, the term of this patent is extended or adjusted under 35 U.S.C. 154(b) by 984 days.

(21) Appl. No.: 17/696,582

(22) Filed: Mar. 16, 2022

(65) Prior Publication Data

US 2022/0202318 A1 Jun. 30, 2022

Related U.S. Application Data

(63) Continuation of application No. 16/537,400, filed on Aug. 9, 2019, now Pat. No. 11,304,631, which is a (Continued)

(51) Int. Cl.
*A61B 5/145* (2006.01)
*A61B 5/00* (2006.01)

(52) U.S. Cl.
CPC ........ *A61B 5/14503* (2013.01); *A61B 5/0004* (2013.01); *A61B 5/0031* (2013.01);
(Continued)

(58) Field of Classification Search
CPC . A61B 5/14503; A61B 5/0004; A61B 5/0031; A61B 5/14532; A61B 5/6833;
(Continued)

(56) References Cited

U.S. PATENT DOCUMENTS

| | | | |
|---|---|---|---|
| 65,604 | A | 6/1867 | Reynolds |
| 5,299,571 | A | 4/1994 | Mastrototaro |

(Continued)

FOREIGN PATENT DOCUMENTS

| | | | | |
|---|---|---|---|---|
| WO | 2007016399 | A2 | 2/2007 | |
| WO | 2011026130 | A1 | 3/2011 | |
| WO | WO-2011119898 | A1 * | 9/2011 | ............ A61B 17/34 |

OTHER PUBLICATIONS

International Preliminary Report on Patentability for Application No. PCT/US2013/035097 mailed Oct. 16, 2014, 13 pages.

(Continued)

*Primary Examiner* — Christian Jang
(74) *Attorney, Agent, or Firm* — Snell & Wilmer LLP

(57) ABSTRACT

The present embodiments relate generally to systems and methods for measuring an analyte in a host. More particularly, the present embodiments provide sensor applicators and methods of use with pushbutton activation that implant the sensor, withdraw the insertion needle, engage the transmitter with the housing, and disengage the applicator from the housing, all in one smooth motion. Some embodiments contemplate engagement of the transmitter with the housing after release of the applicator.

8 Claims, 89 Drawing Sheets

Related U.S. Application Data continuation of application No. 14/976,558, filed on Dec. 21, 2015, now abandoned, which is a continuation of application No. 13/826,372, filed on Mar. 14, 2013, now Pat. No. 9,931,065.

(60) Provisional application No. 61/620,152, filed on Apr. 4, 2012.

(52) U.S. Cl.
CPC ........ *A61B 5/14532* (2013.01); *A61B 5/6833* (2013.01); *A61B 5/6849* (2013.01); *A61B 2560/0412* (2013.01); *A61B 2560/0443* (2013.01)

(58) Field of Classification Search
CPC .......... A61B 5/6849; A61B 2560/0412; A61B 2560/0443
See application file for complete search history.

(56) References Cited

U.S. PATENT DOCUMENTS

| | | | | |
|---|---|---|---|---|
| 5,390,571 | A | 2/1995 | Fox, III et al. | |
| 5,390,671 | A | 2/1995 | Lord et al. | |
| 5,568,806 | A | 10/1996 | Cheney, II et al. | |
| 5,586,553 | A | 12/1996 | Halili et al. | |
| 5,680,858 | A | 10/1997 | Hansen et al. | |
| 5,851,197 | A | 12/1998 | Marano et al. | |
| 5,954,643 | A | 9/1999 | Vanantwerp et al. | |
| 5,993,411 | A | 11/1999 | Choi | |
| 6,093,172 | A | 7/2000 | Funderburk et al. | |
| 6,197,001 | B1 | 3/2001 | Wilson et al. | |
| 6,254,586 | B1 | 7/2001 | Mann et al. | |
| 6,275,717 | B1 | 8/2001 | Gross et al. | |
| 6,293,925 | B1 | 9/2001 | Safabash et al. | |
| 6,607,509 | B2 | 8/2003 | Bobroff et al. | |
| 6,695,860 | B1 | 2/2004 | Ward et al. | |
| 6,936,006 | B2 | 8/2005 | Sabra | |
| 6,990,366 | B2 | 1/2006 | Say et al. | |
| 6,991,619 | B2 | 1/2006 | Marano-Ford et al. | |
| 6,991,620 | B2 | 1/2006 | Marano-Ford et al. | |
| 6,997,907 | B2 | 2/2006 | Safabash et al. | |
| 7,003,336 | B2 | 2/2006 | Holker et al. | |
| 7,022,108 | B2 | 4/2006 | Marano-Ford et al. | |
| 7,130,544 | B2 | 10/2006 | Kasahara et al. | |
| 7,207,974 | B2 | 4/2007 | Safabash et al. | |
| 7,228,162 | B2 | 6/2007 | Ward et al. | |
| 7,310,544 | B2 | 12/2007 | Brister et al. | |
| 7,318,816 | B2 | 1/2008 | Bobroff et al. | |
| 7,343,188 | B2 | 3/2008 | Sohrab | |
| 7,381,184 | B2 | 6/2008 | Funderburk et al. | |
| 7,494,465 | B2 | 2/2009 | Brister et al. | |
| 7,497,827 | B2 | 3/2009 | Brister et al. | |
| 7,582,059 | B2 | 9/2009 | Funderburk et al. | |
| 7,585,287 | B2 | 9/2009 | Bresina et al. | |
| 7,654,956 | B2 | 2/2010 | Brister et al. | |
| 7,660,615 | B2 | 2/2010 | Vanantwerp et al. | |
| 7,682,338 | B2 | 3/2010 | Griffin | |
| 7,686,787 | B2 | 3/2010 | Moberg et al. | |
| 7,697,967 | B2 | 4/2010 | Stafford | |
| 7,699,807 | B2 | 4/2010 | Faust et al. | |
| 7,704,229 | B2 | 4/2010 | Moberg et al. | |
| 7,731,657 | B2 | 6/2010 | Stafford | |
| 7,735,344 | B2 | 6/2010 | Omura et al. | |
| 7,736,310 | B2 | 6/2010 | Taub | |
| 7,736,338 | B2 | 6/2010 | Kavazov et al. | |
| 7,736,344 | B2 | 6/2010 | Moberg et al. | |
| 7,740,613 | B2 | 6/2010 | Yokoi et al. | |
| 7,744,589 | B2 | 6/2010 | Mounce et al. | |
| 7,762,793 | B2 | 7/2010 | Gray et al. | |
| 7,771,393 | B2 | 8/2010 | Liniger et al. | |
| 7,774,145 | B2 | 8/2010 | Brauker et al. | |
| 7,785,293 | B2 | 8/2010 | Gray et al. | |
| 7,789,857 | B2 | 9/2010 | Moberg et al. | |
| 7,815,607 | B2 | 10/2010 | Rutti et al. | |
| 7,846,132 | B2 | 12/2010 | Gravesen et al. | |
| 7,850,652 | B2 | 12/2010 | Liniger et al. | |
| 8,029,441 | B2 | 10/2011 | Mazza et al. | |
| 8,029,442 | B2 | 10/2011 | Funderburk et al. | |
| 8,721,544 | B2 | 5/2014 | Roesicke et al. | |
| 8,764,657 | B2 | 7/2014 | Curry et al. | |
| 9,186,098 | B2 | 11/2015 | Lee et al. | |
| 9,245,167 | B2 | 1/2016 | Carver et al. | |
| 9,265,453 | B2 | 2/2016 | Curry et al. | |
| 9,402,544 | B2 | 8/2016 | Yee et al. | |
| 9,615,779 | B2 | 4/2017 | Pryor et al. | |
| 9,931,065 | B2 | 4/2018 | Pryor et al. | |
| 2003/0100040 | A1* | 5/2003 | Bonnecaze | A61B 5/0031 435/14 |
| 2005/0267505 | A9 | 12/2005 | Shraga | |
| 2006/0016700 | A1 | 1/2006 | Brister et al. | |
| 2006/0052810 | A1* | 3/2006 | Freeman | A61B 5/15113 606/181 |
| 2006/0222566 | A1* | 10/2006 | Brauker | A61B 5/6833 422/68.1 |
| 2007/0027381 | A1 | 2/2007 | Stafford | |
| 2007/0060801 | A1 | 3/2007 | Neinast | |
| 2007/0208244 | A1 | 9/2007 | Brauker et al. | |
| 2008/0114280 | A1* | 5/2008 | Stafford | A61B 5/1468 604/19 |
| 2008/0161656 | A1 | 7/2008 | Bruce et al. | |
| 2008/0242962 | A1 | 10/2008 | Roesicke et al. | |
| 2008/0319414 | A1 | 12/2008 | Yodfat et al. | |
| 2009/0105569 | A1 | 4/2009 | Stafford | |
| 2009/0299301 | A1 | 12/2009 | Gottlieb et al. | |
| 2011/0021889 | A1* | 1/2011 | Hoss | A61B 5/7221 600/310 |
| 2011/0082484 | A1 | 4/2011 | Saravia et al. | |
| 2011/0288574 | A1* | 11/2011 | Curry | A61B 5/150022 606/185 |
| 2012/0095406 | A1 | 4/2012 | Gyrn et al. | |
| 2012/0303043 | A1 | 11/2012 | Donnay | |
| 2012/0323098 | A1* | 12/2012 | Moein | A61B 5/6848 29/832 |
| 2013/0150691 | A1* | 6/2013 | Pace | A61B 5/0002 600/347 |
| 2013/0267811 | A1 | 10/2013 | Pryor et al. | |
| 2013/0267812 | A1 | 10/2013 | Pryor et al. | |
| 2013/0267813 | A1 | 10/2013 | Pryor et al. | |
| 2014/0031655 | A1 | 1/2014 | Stafford | |
| 2015/0025338 | A1 | 1/2015 | Lee et al. | |
| 2015/0025345 | A1 | 1/2015 | Funderburk et al. | |
| 2016/0106349 | A1 | 4/2016 | Pryor et al. | |
| 2019/0357818 | A1 | 11/2019 | Pryor et al. | |

OTHER PUBLICATIONS

International Search Report and Written Opinion for Application No. PCT/US2013/035097 mailed Nov. 14, 2013, 18 pages.

* cited by examiner

TRANSCUTANEOUS ANALYTE SENSORS, APPLICATORS THEREFOR, AND ASSOCIATED METHODS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/537,400, filed on Aug. 9, 2019, which is a continuation of U.S. application Ser. No. 14/976,558, filed Dec. 21, 2015, now abandoned, which is a continuation of U.S. application Ser. No. 13/826,372, filed on Mar. 14, 2013, now U.S. Pat. No. 9,931,065, which claims priority to U.S. Provisional Application No. 61/620,152, filed on Apr. 4, 2012. Each of the aforementioned applications is incorporated by reference herein in its entirety, and each is hereby expressly made a part of this specification.

TECHNICAL FIELD

Systems and methods for measuring an analyte in a host are provided. More particularly, systems and methods for applying a transcutaneous analyte measurement system to a host.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-owering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

The process of applying the sensor to the person is important for such a system to be effective and user friendly. The application process should result in the sensor assembly being attached to the person in a state where it is capable of sensing glucose level information, communicating the glucose level information to the transmitter, and transmitting the glucose level information to the receiver.

SUMMARY

The present systems and methods relate to systems and methods measuring an analyte in a host, and for applying a transcutaneous analyte measurement system to a host. The various embodiments of the present systems and methods for processing analyte sensor data have several features, no single one of which is solely responsible for their desirable attributes. Without limiting the scope of the present embodiments as expressed by the claims that follow, their more prominent features now will be discussed briefly. After considering this discussion, and particularly after reading the section entitled “Detailed Description,” one will understand how the features of the present embodiments provide the advantages described herein.

One aspect of the present embodiments includes the realization that, with some sensors, the process of applying the sensor to the person is important for such a system to be effective and user friendly. Accordingly, a device configured for ease of application may be beneficial. Similarly, a method of application is desirable if it results in the sensor assembly readily being attached to the person in a state where it is capable of sensing glucose level information, communicating the glucose level information to the transmitter, and transmitting the glucose level information to the receiver.

Accordingly, in a first aspect, a device is provided for applying an on-skin sensor assembly to skin of a host, the device comprising: a base configured to secure a housing, wherein the housing is configured to receive an electronics unit, wherein the electronics unit is configured to generate analyte information based on a signal from a sensor; a sensor insertion mechanism configured to insert the sensor into the host; and a trigger configured, in response to being activated, to cause the sensor insertion mechanism to insert the sensor into the host, to secure the electronics unit to the housing such that the sensor electrically contacts the electronics unit, and to cause the housing to detach from the base.

In an embodiment of the first aspect, which is generally applicable, particularly with any other embodiment of the first aspect, the electronics unit is configured, in response to the trigger being activated and/or the electrical connection of the sensor to the electronics unit, to generate analyte information. In some embodiments, the electronics unit is configured to transmit the generated analyte information in response to the generation of analyte information.

In an embodiment of the first aspect, which is generally applicable, particularly with any other embodiment of the first aspect, the housing comprises an adhesive configured to attach the housing to the host. In some embodiments, the adhesive is covered by a liner and/or the adhesive is air permeable and waterproof or water resistant, and/or the adhesive has a backing, and the sensor is configured, when inserted into the host, to extend through the adhesive and backing, and wherein the backing is configured to be moisture permeable at a location proximal to the sensor, and/or the adhesive has a backing that is moisture impermeable in an area peripheral to the housing and the electronics unit.

In an embodiment of the first aspect, which is generally applicable, particularly with any other embodiment of the first aspect, the housing is configured such that the electronics unit cannot be removed from the housing while the housing is adhered to the skin of the host.

In an embodiment of the first aspect, which is generally applicable, particularly with any other embodiment of the first aspect, wherein the sensor insertion mechanism comprises a needle configured to be inserted into the host while the needle holds the sensor, and to be retracted from the host while leaving a portion of the sensor in the host. In certain embodiments, the sensor insertion mechanism further comprises: a needle hub connected to the needle; a wheel configured to move the needle hub; and a torsion spring configured to apply a torque to the wheel; wherein the sensor mechanism is configured, in response to the activation of the trigger, to rotate the wheel in response to the torque from the torsion spring, whereby the needle is inserted into the host and retracted from the host. In certain embodiments, the sensor insertion mechanism further comprises a push rod configured to prevent the sensor from being retracted from the host with the needle. In certain embodiments, the push rod is positioned at least partially within the needle, and is configured to move with the needle as the needle is inserted into the host, and to remain fixed as the needle is retracted from the host.

In an embodiment of the first aspect, which is generally applicable, particularly with any other embodiment of the first aspect, the base is configured to draw the electronics unit into the housing. In certain embodiments, the device can further comprise a magnet configured to draw the electronics unit into the housing, wherein the magnet is situated in the electronics unit or the housing. In certain embodiments, the base can comprise one or more springs configured to draw the electronics unit into the housing. In certain embodiments, each spring can comprise a flexible linear portion having a connection protrusion, wherein the connection protrusion is configured to engage the electronics unit and to cause the linear portion to flex as the electronics unit is inserted into the base, and wherein the connection protrusion is configured to exert a lateral force on the electronics unit to draw the electronics unit into the housing.

In an embodiment of the first aspect, which is generally applicable, particularly with any other embodiment of the first aspect, the device further comprises a standoff configured to limit an extent to which the electronics unit is inserted into the housing prior to sensor insertion. In certain embodiments the trigger is further configured, in response to being activated, to release the electronics unit from the standoff after sensor insertion, and wherein the electronics unit is configured, in response to being released from the standoff, to be secured to the housing such that the sensor electrically connects to one or more contacts on the electronics unit. In certain embodiments, in use, a time between sensor insertion into the host and the electronics unit securing to the housing is less than about 1 second. In certain embodiments, at least one contact on the electronics unit is more rigid than the sensor, and wherein the electronics unit is configured such that, when fully secured to the housing, the at least one contact presses the sensor into an elastomeric seal such that the elastomeric seal is compressed and conforms to the sensor. In certain embodiments, the sensor, when inserted into the host, is configured to be secured in place in the electronics unit by an adhesive material comprising at least one of a high tack gel, a pressure sensitive adhesive, and a two part adhesive. In certain embodiments, the device further comprises a container configured to hold the adhesive material, wherein the container is further configured, as a result of the trigger activation but before the electronics unit is released from a lock, to be compressed so as to release the adhesive material. In certain embodiments, the sensor is configured to be secured in place, after insertion into the host, by one or more of a clamp, a wedge, a barb, a one way valve, or a tension lock. In certain embodiments, the sensor is configured, after insertion into the host, to be surrounded by an elastomeric seal, and wherein the electronics unit is configured, in response to the electronics unit being released from a lock, to compress the elastomeric seal to secure the sensor and to form a seal around the sensor. In certain embodiments, the sensor is configured, after insertion into the host, to be secured in place by a first group of one or more elastomeric seals configured to press against the sensor with a first force and a second group of one or more elastomeric seals configured to press against the sensor with a second force, wherein the first and second forces have different magnitudes or different directions. In certain embodiments, at least one of the first and second groups of elastomeric seals is configured to be compressed while the sensor is inserted through the seals. In certain embodiments, the sensor and needle are configured, after the electronics unit is secured to the housing, to have a mechanical blockage therebetween. In certain embodiments, the sensor is configured, after the electronics unit is secured to the housing, to be sealed and secured by a ferrule surrounding the sensor. In certain embodiments, the device is configured to disengage from the housing and from the electronics unit in response to the electronics unit being released from a lock. In certain embodiments, the device is configured to provide one or more tactile, auditory, or visual indications that the electronics unit has been inserted into the housing to the extent permitted by a lock. In certain embodiments, the device can further comprise an opening through which a mark on the electronics unit is visible if the electronics unit has been inserted into the housing to the extent permitted by the standoff. In certain embodiments, the device can further comprise a drawing mechanism, wherein a position of the drawing mechanism is configured to visually indicate whether the electronics unit has been inserted into the housing to the extent permitted by the standoff.

In an embodiment of the first aspect, which is generally applicable, particularly with any other embodiment of the first aspect, the device can further comprise a trigger lock configured to prevent activation of the trigger. In certain embodiments, the trigger is configured to be released from the trigger lock in response to at least partial insertion of the electronics unit into the device.

In an embodiment of the first aspect, which is generally applicable, particularly with any other embodiment of the first aspect, the housing is configured to substantially fully encapsulate the electronics unit against the host. In certain embodiments, the housing is configured to form a shell that encloses a drawing mechanism, and wherein the housing comprises a septum through which the sensor insertion mechanism is configured to insert the sensor.

In an embodiment of the first aspect, which is generally applicable, particularly with any other embodiment of the first aspect, the sensor insertion mechanism is configured to insert the sensor into the host at a maximum velocity influenced by a flywheel.

In an embodiment of the first aspect, which is generally applicable, particularly with any other embodiment of the first aspect, the sensor insertion mechanism is configured to insert the sensor into the host at a maximum velocity influenced by a fluid passage aperture.

In an embodiment of the first aspect, which is generally applicable, particularly with any other embodiment of the first aspect, the sensor insertion mechanism is configured to insert the sensor into the host at a maximum velocity influenced by a mass of a component of the sensor insertion mechanism.

In an embodiment of the first aspect, which is generally applicable, particularly with any other embodiment of the first aspect, the sensor insertion mechanism is configured to insert the sensor into the host at a maximum velocity influenced by a centrifugal brake.

In an embodiment of the first aspect, which is generally applicable, particularly with any other embodiment of the first aspect, the trigger is configured to cause the sensor insertion mechanism to insert the sensor into the host, to secure the electronics unit to the housing such that the sensor electrically contacts the electronics unit, and to cause the housing to detach from the base, when motion is provided to the trigger by a user. In certain embodiments the sensor insertion mechanism comprises a needle carrier configured to decelerate at a rate limited by a bumper. In certain embodiments, the sensor insertion mechanism comprises a tab protruding in an axial direction from a wheel and configured to rotate about a fixed point, wherein rotational movement of the tab translates into a linear movement of a needle carrier to insert the sensor into the host.

In an embodiment of the first aspect, which is generally applicable, particularly with any other embodiment of the first aspect, the device can have a size and shape so as to substantially fit within a palm of a hand.

In an embodiment of the first aspect, which is generally applicable, particularly with any other embodiment of the first aspect, the base is substantially oval and extends substantially perpendicularly from a substantially oval shaped wall, and wherein the wall surrounds a top portion on which the trigger is disposed. In certain embodiments, the trigger forms substantially an entire top of the device.

In an embodiment of the first aspect, which is generally applicable, particularly with any other embodiment of the first aspect, the device further comprises a protective cover configured to cover the electronics unit and the housing after sensor insertion and to secure the electronics unit to the housing. In some embodiments, an internal portion of the protective cover conforms to the shape of the base and the electronics unit. In some embodiments, the protective cover is waterproof or water resistant, and is air permeable. In some embodiments, the protective cover is molded to have an appearance of an animal or a character. In some embodiments, the protective cover comprises an adhesive that attaches the protective cover to the housing and/or electronics unit.

In an embodiment of the first aspect, which is generally applicable, particularly with any other embodiment of the first aspect, the device has an exterior formed at least partly of a hard plastic.

In an embodiment of the first aspect, which is generally applicable, particularly with any other embodiment of the first aspect, the device further comprises an elastomer, wherein the elastomer is situated at least partly around a perimeter of the device and is configured to relieve strain caused by movement of the host.

In an embodiment of the first aspect, which is generally applicable, particularly with any other embodiment of the first aspect, the electronics unit is configured, once it is secured to the housing, to destroy the housing upon removal from the housing.

In an embodiment of the first aspect, which is generally applicable, particularly with any other embodiment of the first aspect, the device further comprises a blood reservoir configured to receive blood from the host through a weep hole in the housing. In some embodiments, the reservoir comprises at least one of a sponge, a super absorbent polymer, or a wicking material configured to absorb the blood. In some embodiments, the reservoir is an aerated reservoir.

In an embodiment of the first aspect, which is generally applicable, particularly with any other embodiment of the first aspect, the electronics unit comprises at least one electrical contact comprising one or more conductive materials selected from carbon, a carbon embedded silicone elastomer, a conductive polymer, or a conductive salt.

In an embodiment of the first aspect, which is generally applicable, particularly with any other embodiment of the first aspect, the sensor comprises an electrical contact comprising one or more conductive materials selected from carbon, a carbon embedded silicone elastomer, a conductive polymer, or a conductive salt.

In a second aspect, a method is provided of applying an on-skin sensor assembly to a host, wherein the on-skin sensor assembly comprises a housing secured to the applicator, wherein the housing is configured to receive an electronics unit, the method comprising: attaching an applicator to a skin of a host, the applicator comprising a sensor insertion mechanism, a trigger, and a base; inserting the electronics unit into the housing, wherein the electronics unit is configured to generate analyte information based on a signal from a sensor; activating the trigger, thereby causing the sensor insertion mechanism to insert a sensor into the host, to secure the electronics unit to the housing such that the sensor electrically contacts the electronics unit, and to cause the housing to detach from the base; and removing the applicator from the skin of the host, whereby an on-skin sensor assembly comprising the housing, the electronics unit, and the inserted sensor remains on the skin of the host.

In an embodiment of the second aspect, which is generally applicable, particularly with any other embodiment of the second aspect, attaching the applicator to the skin of the host occurs before the electronics unit is inserted into the housing.

In an embodiment of the second aspect, which is generally applicable, particularly with any other embodiment of the second aspect, attaching the applicator to the skin of the host occurs after the electronics unit is inserted into the housing.

In an embodiment of the second aspect, which is generally applicable, particularly with any other embodiment of the second aspect, the method further comprises before applying the applicator, removing a door from the applicator covering a port configured for receiving the electronics unit when the electronics unit is inserted into the housing.

In an embodiment of the second aspect, which is generally applicable, particularly with any other embodiment of the second aspect, the method further comprises a removable liner covering an adhesive patch, wherein the adhesive patch is attached to the housing and radially extends from the housing, and wherein the adhesive patch comprises an adhesive configured to attach the base to the host. In certain embodiments, the adhesive patch is removably attached to the base with a second adhesive that is weaker than the adhesive configured to attach the base to the host, and/or the adhesive patch comprises a removable second liner situated between the base and the adhesive patch. In certain embodiments, the second liner is removably attached to the base with a second adhesive. In certain embodiments, the device is provided in a package configured to contain the base, the housing, the sensor insertion mechanism, and the trigger, wherein the package comprises the removable liner covering the adhesive patch. In certain embodiments, the package further comprises a cover, wherein the cover is a component of the applicator. In certain embodiments, the package further comprises a removable door, wherein the removable door covers a port configured for receiving the electronics unit. In certain embodiments, the removable liner comprises instructions printed thereon for using the applicator. In certain embodiments, multiple applicators are provided in the package.

In an embodiment of the second aspect, which is generally applicable, particularly with any other embodiment of the second aspect, the applicator comprises a removable liner covering an adhesive patch, wherein the adhesive patch is attached to the housing, wherein the adhesive patch comprises an adhesive configured to attach the base to the host, wherein removing the applicator from the package exposes the adhesive, and wherein attaching the applicator causes the adhesive to attach the housing to the host.

In a third aspect, a method is provided of applying an on-skin sensor assembly to a host, the method comprising: attaching an applicator to a skin of a host, the applicator comprising a sensor insertion mechanism, a trigger, and a base; a housing secured to the applicator, wherein the housing is configured to receive an electronics unit; activating the trigger, thereby causing the sensor insertion mechanism to insert a sensor into the host and to cause the housing to detach from the base; removing the applicator from the skin of the host, whereby the housing and the inserted sensor remain on the skin of the host; and inserting the electronics unit into the housing, wherein the electronics unit is configured to generate analyte information based on a signal from the sensor, and wherein the electronics unit is secured to the housing such that the sensor electrically contacts the electronics unit, whereby an on-skin sensor assembly comprising the housing, the electronics unit, and the inserted sensor is obtained.

In an embodiment of the third aspect, which is generally applicable, particularly with any other embodiment of the third aspect, the housing is configured to receive the electronics unit in a partially seated configuration, and wherein the trigger is configured, in response to being activated, to cause the sensor insertion mechanism to insert the sensor into the host and to fully seat the electronics unit to the housing such that the sensor electrically contacts the electronics unit. In certain embodiments, the partially seated configuration is provided by a lock configured to limit an extent to which the electronics unit can be inserted into the housing prior to sensor insertion. In certain embodiments, the trigger is further configured to release the electronics unit from the lock after sensor insertion, wherein in response to the electronics unit being released from the lock, the electronics unit is configured to be secured to the housing such that the sensor electrically connects to one or more contacts on the electronics unit. In certain embodiments, a time between the sensor insertion into the host and the electronics unit securing the sensor is less than about 1 s.

In an embodiment of the third aspect, which is generally applicable, particularly with any other embodiment of the third aspect, the base is configured to draw the electronics unit into the housing. In certain embodiments, at least one of the electronics unit and the housing comprises a magnet configured to draw the electronics unit into the housing. In certain embodiments, the base comprises one or more springs configured to draw the electronics unit into the housing. In certain embodiments, each spring is connected to a contact element, wherein the contact element is configured to engage the electronics unit and to cause the spring to compress as the electronics unit is inserted into the housing, and wherein the contact element is configured to exert a lateral force on the electronics unit to draw the electronics unit into the housing. In certain embodiments, each spring comprises a flexible linear portion having a connection protrusion, wherein the connection protrusion is configured to engage the electronics unit and to cause the linear portion to flex as the electronics unit is inserted into the base, and wherein the connection protrusion is configured to exert a lateral force on the electronics unit to draw the electronics unit into the housing.

In an embodiment of the third aspect, which is generally applicable, particularly with any other embodiment of the third aspect, the device is configured to provide one or more tactile, auditory, or visual indications that the electronics unit has been inserted into the housing in the partially seated configuration.

In an embodiment of the third aspect, which is generally applicable, particularly with any other embodiment of the third aspect, the device further comprises a trigger lock configured to prevent activation of the trigger. In certain embodiments, the trigger is configured to be released from the trigger lock in response to at least partial insertion of the electronics unit into the housing.

In an embodiment of the third aspect, which is generally applicable, particularly with any other embodiment of the third aspect, the housing is configured to adhere to a host's skin, wherein, in use, the sensor is configured to extend through the housing and into the host's skin; and the electronics unit is configured to operably connect to the sensor and generate analyte information based on a signal from the sensor when the electronics unit is secured within the housing, wherein operable connection of the electronics unit to the sensor comprises pressing the sensor against one or more electrical contacts of the electronics unit, and wherein the sensor is configured to be held in the assembly with a retention force.

In an embodiment of the third aspect, which is generally applicable, particularly with any other embodiment of the third aspect, the sensor is configured such that connection of the electronics unit to the sensor causes the sensor to bend, whereby the sensor is configured to conform to the shape of the one or more electrical contacts.

In an embodiment of the third aspect, which is generally applicable, particularly with any other embodiment of the third aspect, the sensor is configured to be secured in place after insertion in the host by an adhesive material comprising at least one of a high tack gel, a pressure sensitive adhesive, or a two part adhesive. In certain embodiments, the adhesive material is configured to be enclosed in the container, and wherein the container is configured to be compressed so as to release the adhesive material upon activation of the trigger.

In an embodiment of the third aspect, which is generally applicable, particularly with any other embodiment of the third aspect, the sensor is configured to be secured in place by one or more of a clamp, a wedge, a barb, a one way valve, or a tension lock.

In an embodiment of the third aspect, which is generally applicable, particularly with any other embodiment of the third aspect, the housing comprises an elastomeric seal configured to form a seal around the sensor when the electronics unit is operably connected to the sensor.

In an embodiment of the third aspect, which is generally applicable, particularly with any other embodiment of the third aspect, the sensor is configured, after insertion into the host, to be secured in place by a first group of one or more elastomeric seals configured to press against the sensor with a first force and a second group of one or more elastomeric seals configured to press against the sensor with a second force, wherein the first and second forces have different magnitudes and/or different directions. In certain embodiments, at least one of the first and second groups of elastomeric seals is configured to be compressed while the sensor is inserted through the seals.

In an embodiment of the third aspect, which is generally applicable, particularly with any other embodiment of the third aspect, the sensor and needle are configured, after the electronics unit is secured to the housing, to have a mechanical blockage therebetween.

In an embodiment of the third aspect, which is generally applicable, particularly with any other embodiment of the third aspect, the sensor is configured, after the electronics unit is secured to the housing, to be sealed and secured by a ferrule surrounding the sensor.

In an embodiment of the third aspect, which is generally applicable, particularly with any other embodiment of the third aspect, the sensor is in a form of a wire.

In an embodiment of the third aspect, which is generally applicable, particularly with any other embodiment of the third aspect, the retention force is at least about 0.1 pounds when subjected to a standard pull test or a standard push test.

In an embodiment of the third aspect, which is generally applicable, particularly with any other embodiment of the third aspect, the electronics unit is inserted into the housing after the applicator is removed from the skin of the host.

In a fourth aspect, a device is provided for applying an on-skin sensor assembly to skin of a host, the device comprising: a base configured to secure a housing, wherein the housing is configured to receive a transmitter, and the transmitter is configured to generate analyte information based on a signal from a sensor; and a mechanism configured to, in response to a single action by a user, cause the sensor to be inserted into the host, to secure the electronics unit to the housing such that the sensor electrically contacts the electronics unit, and to cause the housing to detach from the base.

In an embodiment of the fourth aspect, which is generally applicable, particularly with any other embodiment of the fourth aspect, the mechanism includes a trigger, and the single action comprises activating the trigger to release stored energy and set components within the device in motion. In certain embodiments, the stored energy is stored in a torsion spring that, when released, causes a wheel to rotate. In certain embodiments, rotation of the wheel induces linear motion in a needle carrier. In certain embodiments, the wheel and the needle carrier comprise a Scotch yoke.

In an embodiment of the fourth aspect, which is generally applicable, particularly with any other embodiment of the fourth aspect, the mechanism further includes a pushrod and a needle, and when the mechanism is activated the pushrod ejects the sensor from a lumen of the needle and subsequently retracts into the needle lumen.

In an embodiment of the fourth aspect, which is generally applicable, particularly with any other embodiment of the fourth aspect, the mechanism is prevented from actuation until the transmitter is partially seated within the housing.

In a fifth aspect, a device is provided for applying an on-skin sensor assembly to skin of a host, the device comprising: a sensor; a sensor insertion mechanism containing the sensor; and a housing containing the sensor insertion mechanism, the housing being substantially dome shaped such that it is configured to be comfortably held in the palm of a hand, and such that the housing can be held during a process of inserting the sensor into the skin of the host at any location on the abdomen of the host with the host's wrist in a neutral position.

In a sixth aspect, a device is provided for applying an on-skin sensor assembly to skin of a host, the device comprising: a base configured to secure a housing, wherein the housing is configured to receive an electronics unit, wherein the electronics unit is configured to generate analyte information based on a signal from a sensor; a sensor insertion mechanism configured to insert the sensor into the host, and including a needle carrying the sensor, a rotatable wheel, and a linearly translatable needle carrier; and a trigger configured, in response to being activated, to cause the rotatable wheel to rotate, which in turn causes the linearly translatable needle carrier to translate toward the host to implant the sensor, and subsequently to translate away from the host to withdraw the needle from the host.

In an embodiment of the sixth aspect, which is generally applicable, particularly with any other embodiment of sixth aspect, the wheel and the needle carrier comprise a Scotch yoke.

In an embodiment of the sixth aspect, which is generally applicable, particularly with any other embodiment of sixth aspect, the device further comprises a torsion spring that stores energy, and when the trigger is activated, the energy stored in the torsion spring is released, causing the wheel to rotate. In some embodiments, the wheel includes a flange, and the trigger bears against the flange to retain the energy stored within the torsion spring.

In an embodiment of the sixth aspect, which is generally applicable, particularly with any other embodiment of sixth aspect, the device further comprises a pushrod and a needle, and when the trigger is activated the pushrod ejects the sensor from a lumen of the needle and subsequently retracts into the needle lumen.

In an embodiment of the sixth aspect, which is generally applicable, particularly with any other embodiment of sixth aspect, the trigger is prevented from actuation until the electronics unit is partially seated within the housing.

In a seventh aspect, a device is provided for applying an on-skin sensor assembly to skin of a host, the device comprising: a base configured to secure a housing; and an electronics unit including at least one electrical contact, wherein the housing is configured to receive the electronics unit, wherein the electronics unit is configured to generate analyte information based on a signal from a sensor; wherein the base includes a mechanism to apply a seating force to the electronics unit in a direction of insertion of the electronics unit into the housing upon partial seating of the electronics unit within the housing.

In an embodiment of the seventh aspect, which is generally applicable, particularly with any other embodiment of seventh aspect, the seating force is about 0.25-3 lbs.

In an embodiment of the seventh aspect, which is generally applicable, particularly with any other embodiment of seventh aspect, upon activation of the device, a sealing force is applied to the sensor that is about 2-3 times the magnitude of the seating force.

In an embodiment of the seventh aspect, which is generally applicable, particularly with any other embodiment of seventh aspect, the mechanism includes a pair of spring arms, and the spring arms are pre-loaded with stored energy, and partially seating the electronics unit within the housing releases the stored energy.

In an embodiment of the seventh aspect, which is generally applicable, particularly with any other embodiment of seventh aspect, the mechanism includes a pair of spring arms, and the spring arms are pre-loaded with stored energy, and activating the device releases the stored energy.

In an embodiment of the seventh aspect, which is generally applicable, particularly with any other embodiment of seventh aspect, upon activation of the device the force moves the electronics unit farther into the housing, causing the at least one electrical contact to contact the sensor.

In an embodiment of the seventh aspect, which is generally applicable, particularly with any other embodiment of seventh aspect, the mechanism comprises at least one spring. In certain embodiments, the at least one spring is a leaf spring. In certain embodiments, the at least one spring is a pair of leaf springs located on opposite sides of the electronics unit.

In an embodiment of the seventh aspect, which is generally applicable, particularly with any other embodiment of seventh aspect, partial seating of the electronics unit releases a trigger lock, thereby allowing the device to be actuated. In certain embodiments, if the electronics unit backs out from the partially seated position, the trigger lock reengages, thereby preventing the device from being actuated.

In an eighth aspect, a device is provided for applying an on-skin sensor assembly to skin of a host, the device comprising: a housing; and an electronics unit, wherein the electronics unit is configured to generate analyte information based on a signal from a sensor; a sensor insertion mechanism configured to insert the sensor into the host; and a trigger configured, in response to being activated, to cause the sensor insertion mechanism to insert the sensor into skin of the host, and to secure the electronics unit to the housing such that the sensor electrically contacts the electronics unit, and in such a way that reuse of the sensor is prevented.

In an embodiment of the eighth aspect, which is generally applicable, particularly with any other embodiment of eighth aspect, the electronics unit may not be removed from the housing without destroying the housing.

In an embodiment of the eighth aspect, which is generally applicable, particularly with any other embodiment of eighth aspect, the electronics unit may not be removed from the housing without removing an adhesive patch located between the housing and the host from the housing or from the host.

In an embodiment of the eighth aspect, which is generally applicable, particularly with any other embodiment of eighth aspect, when the housing is adhered to the host's skin, the skin blocks movement of a lever, which is used to remove the transmitter from the housing such that the transmitter can only be removed from the housing after the sensor has been removed from the body and is thereby rendered unusable.

In a ninth aspect, a device is provided for applying an on-skin sensor assembly to skin of a host, the device comprising: a housing, wherein the housing is configured to receive an electronics unit, wherein the electronics unit is configured to generate analyte information based on a signal from a sensor; a sensor insertion mechanism configured to insert the sensor into the host; a trigger configured, in response to being activated, to cause the sensor insertion mechanism to insert the sensor into the host; and a trigger lock configured to prevent activation of the trigger until the electronics unit is partially seated within the housing.

In an embodiment of the ninth aspect, which is generally applicable, particularly with any other embodiment of ninth aspect, the trigger lock comprises a projection on a rear side of the trigger that engages a surface to prevent movement of the trigger.

In an embodiment of the ninth aspect, which is generally applicable, particularly with any other embodiment of ninth aspect, if the electronics unit backs out from the partially seated position, the trigger lock reengages, thereby preventing the device from being actuated.

In an embodiment of the ninth aspect, which is generally applicable, particularly with any other embodiment of ninth aspect, the electronics unit disengages the trigger lock as it is partially seated within the housing.

In further aspects and embodiments, the above method features of the various aspects are formulated in terms of a system as in various aspects, having the analyte sensor and control means configured to carry out the method features. Any of the features of an embodiment of any of the aspects, including but not limited to any embodiments of any of the first through ninth aspects referred to above, is applicable to all other aspects and embodiments identified herein, including but not limited to any embodiments of any of the first through ninth aspects referred to above. Moreover, any of the features of an embodiment of the various aspects, including but not limited to any embodiments of any of the first through ninth aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the first through ninth aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the first through ninth aspects referred to above.

DETAILED DESCRIPTION

The following description and examples illustrate some example embodiments of the disclosed invention in detail. Those of skill in the art will recognize that there are numerous variations and modifications of this invention that are encompassed by its scope. Accordingly, the description of a certain example embodiment should not be deemed to limit the scope of the present invention.

Sensor System and Applicator

Figure 1:
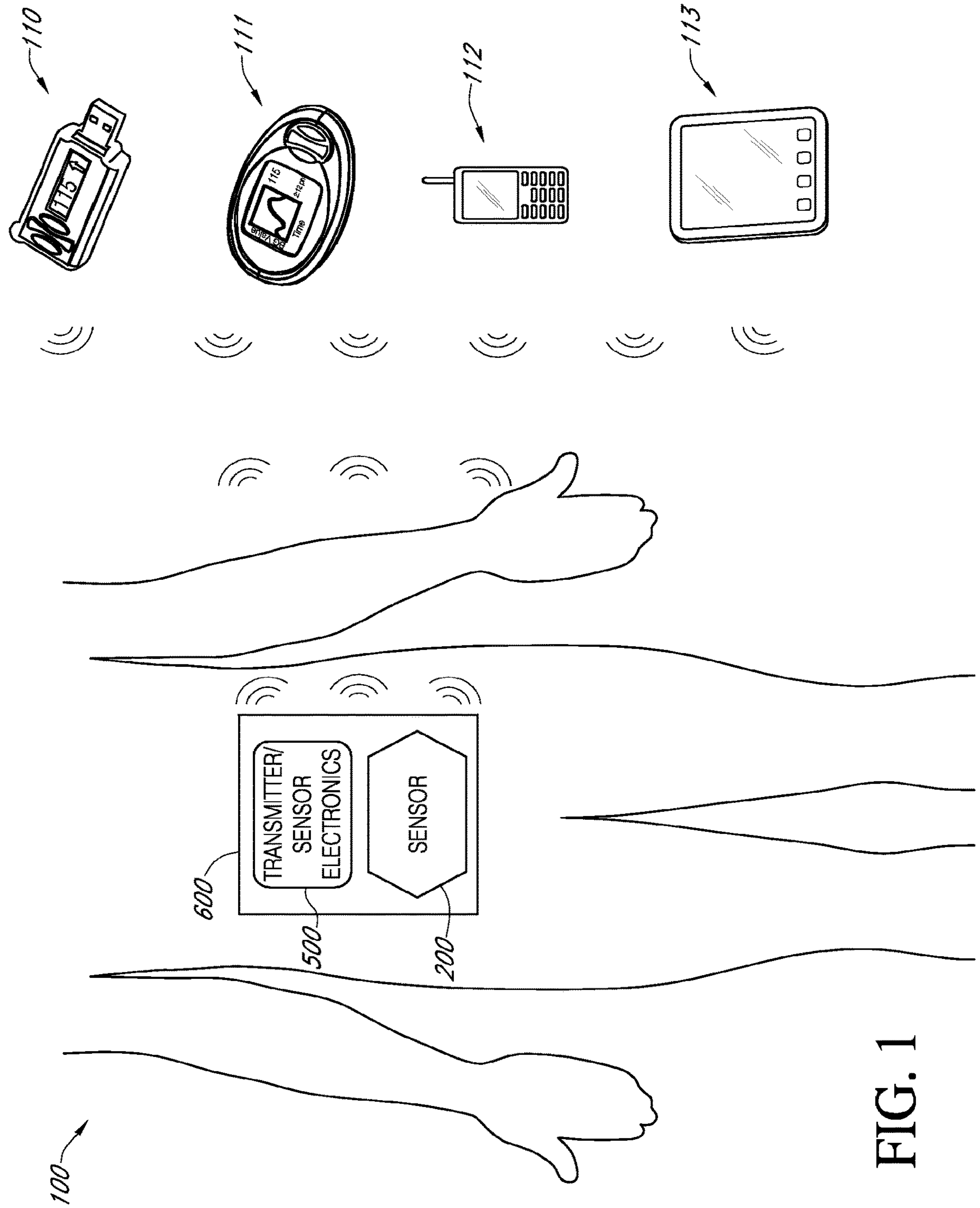
FIG. 1 is a schematic view of a continuous analyte sensor system attached to a host and communicating with other devices.

FIG. 1 is a schematic of a continuous analyte sensor system 100 attached to a host and communicating with a number of other example devices 110-113. A transcutaneous analyte sensor system comprising an on-skin sensor assembly 600 is shown which is fastened to the skin of a host via a disposable housing (not shown). The system includes a transcutaneous analyte sensor 200 and an electronics unit (referred to interchangeably as "sensor electronics" or "transmitter") 500 for wirelessly transmitting analyte information to a receiver. During use, a sensing portion of the sensor 200 is under the host's skin and a contact portion of the sensor 200 is electrically connected to the electronics unit 500. The electronics unit 500 is engaged with a housing which is attached to an adhesive patch fastened to the skin of the host.

The on-skin sensor assembly 600 may be attached to the host with use of an applicator adapted to provide convenient and secure application. Such an applicator may also be used for attaching the electronics unit 500 to a housing, inserting the sensor 200 through the host's skin, and connecting the sensor 200 to the electronics unit 500. Once the electronics unit 500 is engaged with the housing and the sensor 200 has been inserted and is connected to the electronics unit 500, the applicator detaches from the sensor assembly.

In general, the continuous analyte sensor system 100 includes any sensor configuration that provides an output signal indicative of a concentration of an analyte. The output signal including (e.g., sensor data, such as a raw data stream, filtered data, smoothed data, and/or otherwise transformed sensor data) is sent to the receiver, which is described in more detail below. In one embodiment, the analyte sensor system 100 includes a transcutaneous glucose sensor, such as is described in US Patent Publication No. US-2011-0027127-A1, the contents of which is hereby incorporated by reference in its entirety. In some embodiments, the sensor system 100 includes a continuous glucose sensor and comprises a transcutaneous sensor such as described in U.S. Pat. No. 6,565,509 to Say et al., for example. In another embodiment, the sensor system 100 includes a continuous glucose sensor and comprises a subcutaneous sensor such as described with reference to U.S. Pat. No. . 6,579,690 to Bonnecaze et al. or U.S. Pat. No. 6,484,046 to Say et al., for example. In another embodiment, the sensor system 100 includes a continuous glucose sensor and comprises a refillable subcutaneous sensor such as described with reference to U.S. Pat. No. 6,512,939 to Colvin et al. In another embodiment, the sensor system 100 includes a continuous glucose sensor and comprises an intravascular sensor such as described with reference to U.S. Pat. No. 6,477,395 to Schulman et al., for example. In another embodiment, the sensor system 100 includes a continuous glucose sensor and comprises an intravascular sensor such as described with reference to U.S. Pat. No. 6,424,847 to Mastrototaro et al. Other signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entirety. The sensor extends through a housing, which maintains the sensor on the skin and provides for electrical connection of the sensor to sensor electronics, provided in the electronics unit.

In one embodiment, the sensor is formed from a wire or is in a form of a wire. For example, the sensor can include an elongated conductive body, such as, a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments, the smallest dimension of the elongated conductive body is less than about 0.1 inches, less than about 0.075 inches, less than about 0.05 inches, less than about 0.025 inches, less than about 0.01 inches, less than about 0.004 inches, or less than about 0.002 inches. The sensor may have a circular cross-section. In some embodiments, the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To such a clad electrode, one or two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

In certain embodiments, the materials used to form the elongated conductive body (e.g., stainless steel, titanium, tantalum, platinum, platinum-iridium, iridium, certain polymers, and/or the like) can be strong and hard, and therefore are resistant to breakage. For example, in some embodiments, the ultimate tensile strength of the elongated conductive body is from about 80 kPsi to about 500 kPsi. In another example, in some embodiments, the Young's modulus of the elongated conductive body is from about 160 GPa to about 220 GPa. In still another example, in some embodiments, the yield strength of the elongated conductive body is from about 60 kPsi to about 2200 kPsi. Ultimate tensile strength, Young's modulus, and yield strength are discussed in greater detail elsewhere herein. In some embodiments, the sensor's small diameter provides (e.g., imparts, enables) flexibility to these materials, and therefore to the sensor as a whole. Thus, the sensor can withstand repeated forces applied to it by surrounding tissue. One measurement of the sensor's ability to withstand the implantation environment is fatigue life, which is described in greater detail in the section entitled "Multi-Axis Bending." In some embodiments, the fatigue life of the sensor is at least 1,000 cycles of flexing of from about 28° to about 110° at a bend radius of about 0.125-inches.

In addition to providing structural support, resiliency and flexibility, in some embodiments, the core (or a component thereof) provides electrical conduction for an electrical signal from the working electrode to sensor electronics (not shown), which are described elsewhere herein. In some embodiments, the core comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is conductive material selected to provide electrical conduction between the core and the first layer, and/or to attach the first layer to the core (e.g., if the first layer is formed of a material that does not attach well to the core material). In another embodiment, the core is formed of a non-conductive material (e.g., a non-conductive metal and/or a non-conductive polymer) and the first layer is a conductive material, such as stainless steel, titanium, tantalum, a conductive polymer, and/or the like. The core and the first layer can be of a single (or same) material, e.g., platinum. One skilled in the art appreciates that additional configurations are possible.

In the illustrated embodiments, the electronics unit 500 is releasably attachable to the sensor 200. The electronics unit 500 includes electronic circuitry associated with measuring and processing the continuous analyte sensor data, and is configured to perform algorithms associated with processing and calibration of the sensor data. For example, the electronics unit 500 can provide various aspects of the functionality of a sensor electronics module as described in U.S. Patent Publication No. US-2009-0240120-A1 and U.S. patent application Ser. No. 13/247,856 filed Sep. 28, 2011 and entitled "ADVANCED CONTINUOUS ANALYTE MONITORING SYSTEM," the contents of which are hereby incorporated by reference in their entirety. The electronics unit 500 may include hardware, firmware, and/or software that enable measurement of levels of the analyte via a glucose sensor, such as an analyte sensor 200. For example, the electronics unit 500 can include a potentiostat, a power source for providing power to the sensor 200, other components useful for signal processing and data storage, and preferably a telemetry module for one- or two-way data communication between the electronics unit 500 and one or more receivers, repeaters, and/or display devices, such as devices 110-113. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The electronics unit 500 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, and the like. Examples of systems and methods for processing sensor analyte data are described in more detail herein and in U.S. Pat. Nos. 7,310,544, 6,931,327, U.S. Patent Publication No. 2005-0043598-A1, U.S. Patent Publication No. 2007-0032706-A1, U.S. Patent Publication No. 2007-0016381-A1, U.S. Patent Publication No. 2008-0033254-A1, U.S. Patent Publication No. 2005-0203360-A1, U.S. Patent Publication No. 2005-0154271-A1, U.S. Patent Publication No. 2005-0192557-A1, U.S. Patent Publication No. 2006-0222566-A1, U.S. Patent Publication No. 2007-0203966-A1 and U.S. Patent Publication No. 2007-0208245-A1, the contents of which are hereby incorporated by reference in their entirety.

One or more repeaters, receivers and/or display devices, such as key fob repeater 110, medical device receiver 111 (e.g., insulin delivery device and/or dedicated glucose sensor receiver), smart phone 112, portable computer 113, and the like are operatively linked to the electronics unit, which receive data from the electronics unit 500, which is also referred to as the transmitter and/or sensor electronics body herein, and in some embodiments transmit data to the electronics unit 500. For example, the sensor data can be transmitted from the sensor electronics unit 500 to one or more of key fob repeater 110, medical device receiver 111, smart phone 112, portable computer 113, and the like. In one embodiment, a display device includes an input module with a quartz crystal operably connected to an RF transceiver (not shown) that together function to transmit, receive and synchronize data streams from the electronics unit 500. However, the input module can be configured in any manner that is capable of receiving data from the electronics unit 500. Once received, the input module sends the data stream to a processor that processes the data stream, such as described in more detail below. The processor is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. The processor includes hardware that performs the processing described herein, for example read-only memory (ROM) provides permanent or semi-permanent storage of data, storing data such as sensor ID (sensor identity), receiver ID (receiver identity), and programming to process data streams (for example, programming for performing estimation and other algorithms described elsewhere herein) and random access memory (RAM) stores the system's cache memory and is helpful in data processing. An output module, which may be integral with and/or operatively connected with the processor, includes programming for generating output based on the sensor data received from the electronics unit (and any processing that incurred in the processor).

In some embodiments, analyte values are displayed on a display device. In some embodiments, prompts or messages can be displayed on the display device to convey information to the user, such as reference outlier values, requests for reference analyte values, therapy recommendations, deviation of the measured analyte values from the estimated analyte values, or the like. Additionally, prompts can be displayed to guide the user through calibration or troubleshooting of the calibration.

Additionally, data output from the output module can provide wired or wireless, one- or two-way communication between the receiver and an external device. The external device can be any device that interfaces or communicates with the receiver. In some embodiments, the external device is a computer, and the receiver is able to download current or historical data for retrospective analysis by a physician, for example. In some embodiments, the external device is a modem, and the receiver is able to send alerts, warnings, emergency messages, or the like, via telecommunication lines to another party, such as a doctor or family member. In some embodiments, the external device is an insulin pen, and the receiver is able to communicate therapy recommendations, such as insulin amount and time to the insulin pen. In some embodiments, the external device is an insulin pump, and the receiver is able to communicate therapy recommendations, such as insulin amount and time to the insulin pump. The external device can include other technology or medical devices, for example pacemakers, implanted analyte sensor patches, other infusion devices, telemetry devices, or the like. The receiver may communicate with the external device, and/or any number of additional devices, via any suitable communication protocol, including radio frequency, Bluetooth, universal serial bus, any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, ANT, and/or a proprietary communication protocol.

FIGS. 2A-2D are perspective views of the on-skin sensor assembly and applicator at various stages in a method of an application process in a generally applicable embodiment.

Figure 2A:
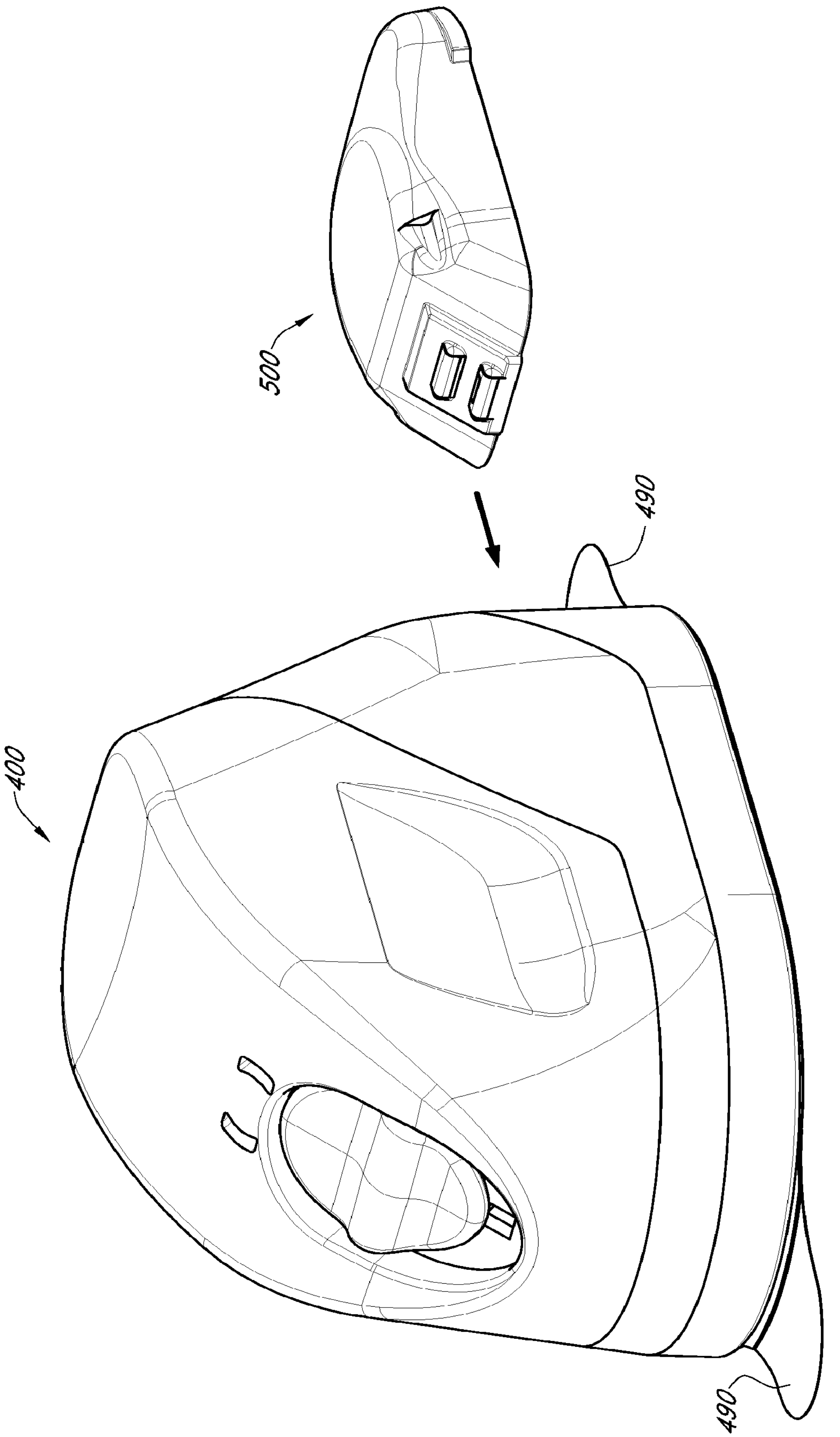
FIGS. 2A-2D are front perspective views of a sensor system and applicator at various stages of a process for applying the sensor system to a host.
Figure 2B:
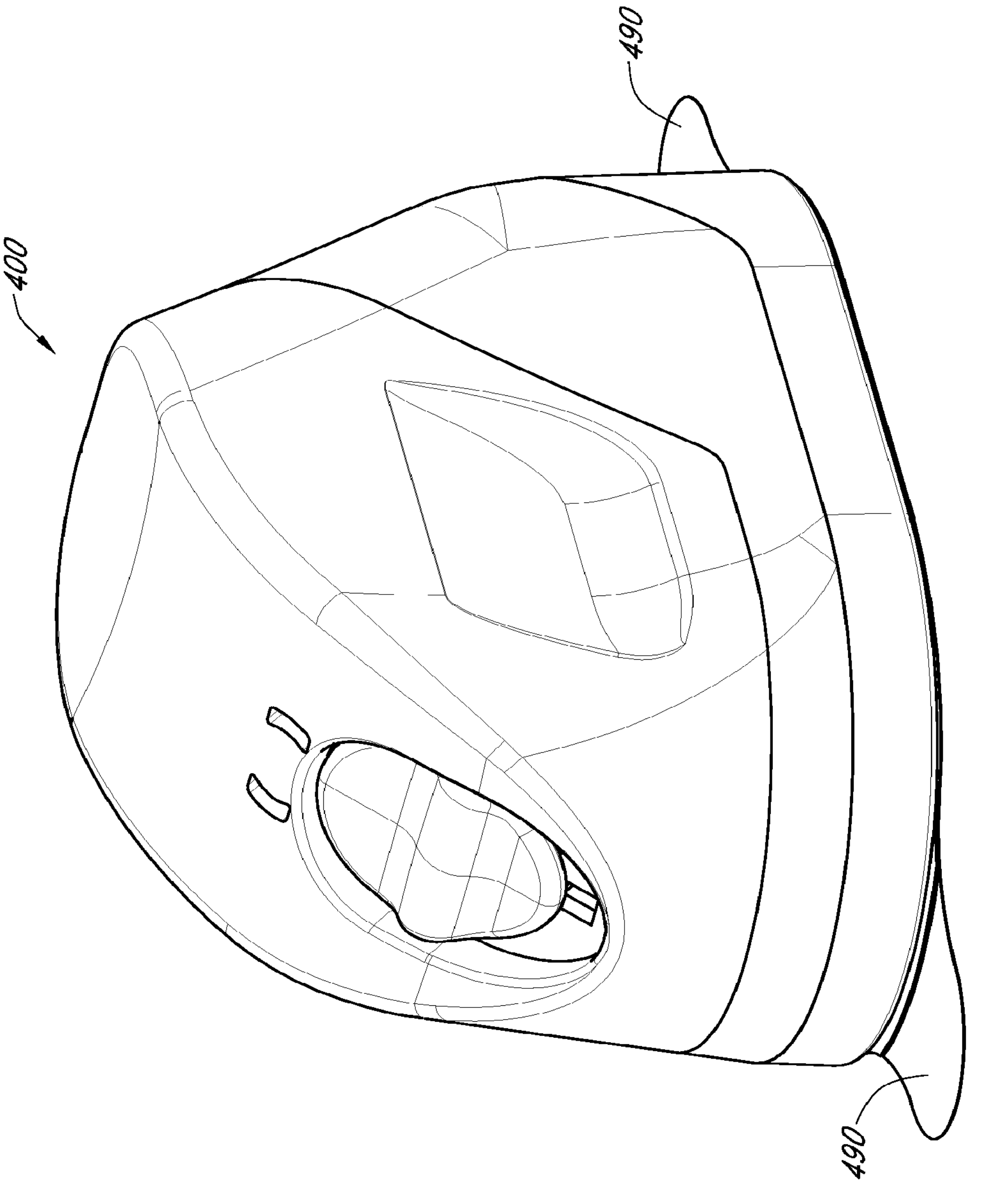
Figure 2C:
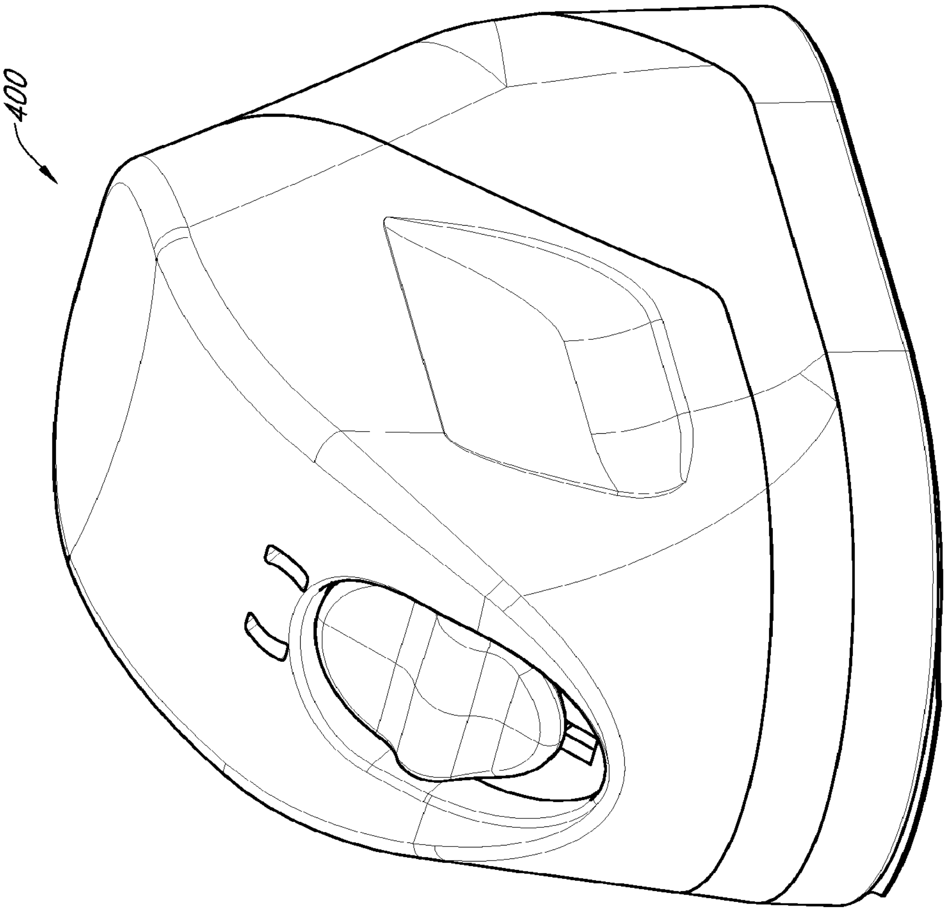
Figure 2D:
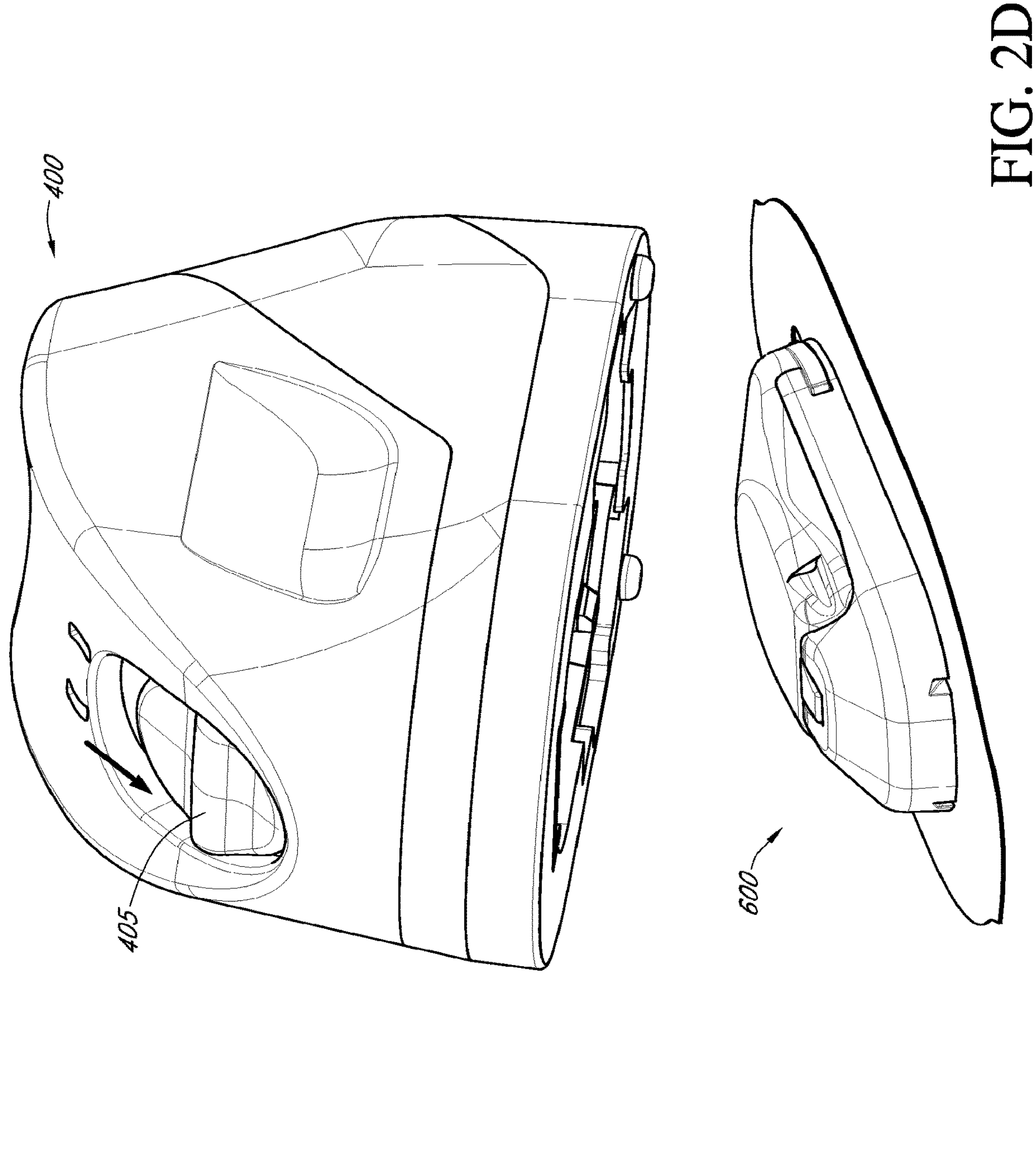

FIG. 2A shows an embodiment of an applicator 400. The applicator 400 has a liner 490 connected thereto which covers an adhesive (not shown). FIG. 2A also shows an embodiment of an electronics unit, also referred to as a transmitter 500. As indicated, the transmitter 500 is inserted through an opening 830 (FIG. 29B) in the applicator 400 and at least partially seated in the housing, as further discussed below. FIG. 2B shows the applicator 400 having the transmitter 500 (not shown) inserted therein. FIG. 2C shows the applicator 500 having the liner 490 (not shown) removed. The removal of the liner 490 exposes an adhesive (not shown) by which the on-skin sensor assembly 600 is attached to the host. After removal of the liner the applicator is placed on to the host. In some embodiments, the transmitter 500 may be inserted into the applicator 400 after the applicator is placed on to the host. FIG. 2D shows that trigger (may be referred to interchangeably as "button") 405 has been activated. The activation of the trigger causes the applicator 400 to insert the sensor into the host, seat the transmitter 500 into the housing, thereby electrically contacting the sensor to electrical contacts of the transmitter 500, and detach the applicator 400 from the on-skin sensor assembly 600. This embodiment advantageously allows the described actions to be automatically performed with a single trigger activation. In some embodiments, the trigger activation also causes the on-skin sensor assembly 600 to begin sensing and transmitting data. In this way, the system embodied here allows a user to perform a few simple steps: insert the transmitter, peel the liner, stick the adhesive to skin and click (activate) the trigger, after which the sensor is automatically inserted (including needle insertion and subsequent retraction), the applicator is automatically released (from the housing) and optionally the sensor electronics automatically begin the sensor session, thereby requiring minimal user interaction to initiate a sensor session.

These results and actions are discussed below in more detail. While specific embodiments are discussed which provide certain mechanical devices for performing the functions discussed, one of skill in the art understands that various modifications may be made. For example, although the embodiment of FIGS. 2A-2D describes a method whereby the transmitter 500 is at least partially seated in the housing prior to sensor insertion, modifications could provide for a system wherein the transmitter 500 is seated in the housing after sensor insertion and applicator removal.

Figure 3A:
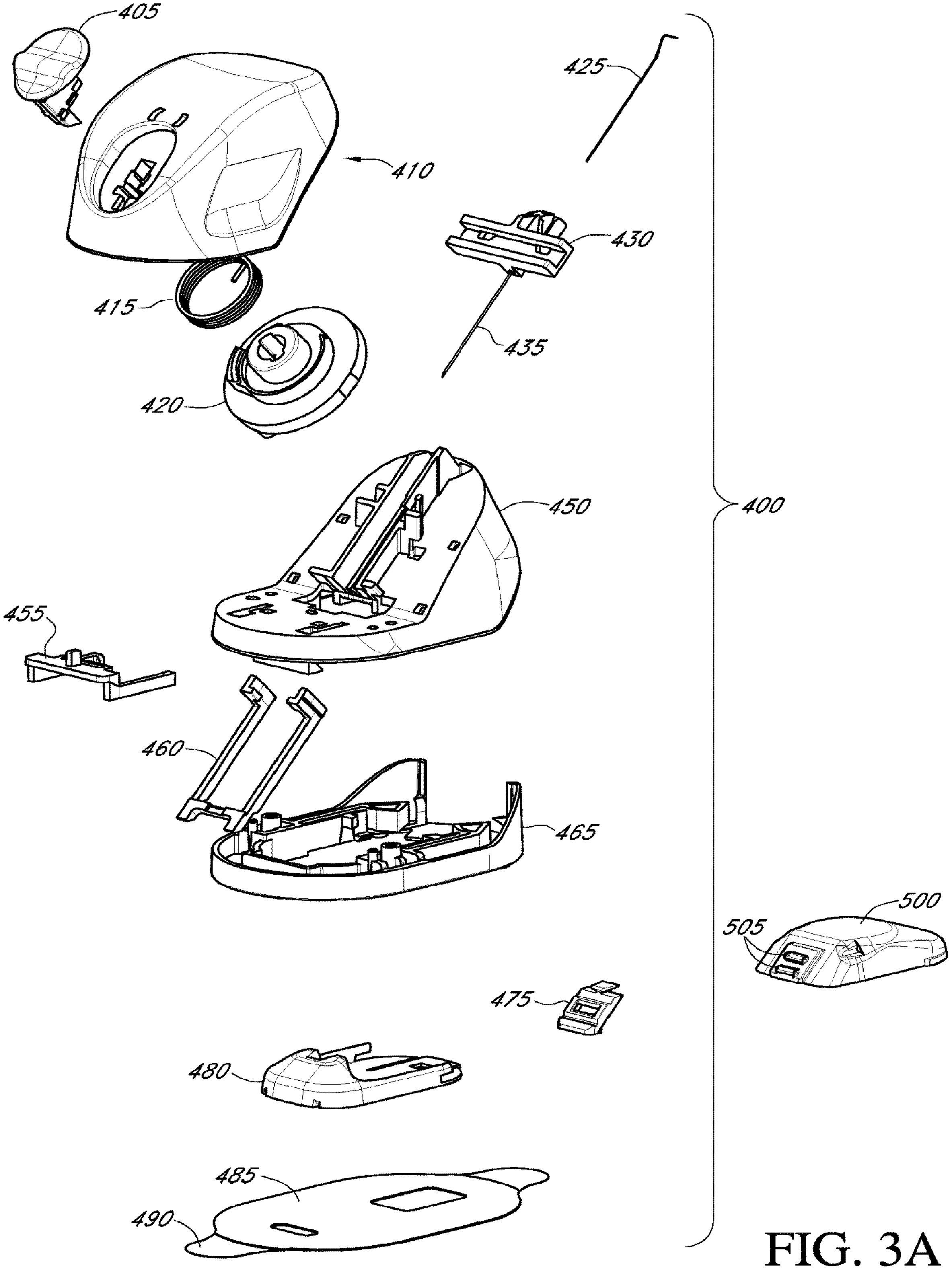
FIG. 3A is an exploded view of the sensor system and applicator of FIGS. 2A-2D.

FIG. 3A is an exploded view of an embodiment of an applicator 400 used in the process shown in FIGS. 2A-2D. Other implementations may be used. Trigger 405 is attached to front cover (may be referred to interchangeably as "housing") 410, and is activated in order to actuate the applicator 400 to cause the applicator 400 to perform the various actions described above and below. Front cover 410 is connected to back cover 450, and front and back covers 410 and 450 cooperatively house a sensor insertion mechanism. The sensor insertion mechanism includes torsion spring 415, wheel 420, push rod 425, needle hub (also referred to as "needle carrier") 430, and needle 435, in which the sensor (not shown) is held prior to activation of the trigger 405. In response to the trigger 405 being activated, the sensor insertion mechanism inserts the sensor into the host.

The applicator also includes a trigger lock 455, which prevents the trigger 405 from being activated until the transmitter 500 has been inserted so as to be at least partially seated in the housing 480. As discussed above and in further detail below, the transmitter 500 is at least partially seated in the housing 480 by inserting the transmitter 500 through the opening in the applicator 400, and is subsequently fully seated into the housing 480 in response to the trigger 405 being activated. A transmitter standoff 460 prevents premature seating of the transmitter 500 fully into the housing 480. Base 465 is connected to the back cover 450 and receives the inserted transmitter 500. The base 465 also guides the transmitter 500 into the housing 480 as the transmitter 500 is inserted into the applicator 400.

The housing 480 includes elastomeric seal 475 positioned within the housing 480 to engage the leading end of the transmitter 500. In response to the applicator 400 being actuated, the transmitter 500 is pressed against the elastomeric seal 475 with the sensor (not shown) between the elastomeric seal 475 and electrical contacts 505 of the transmitter 500 after the sensor has been inserted into the host. Although a variety of embodiments are illustrated and described throughout the present disclosure, such as in FIGS. 3A, 3B, 7, 36 and 47-51, for each of the transmitter, electrical contact and/or elastomeric seal designs, it should be understood that each of the embodiments and descriptions associated therewith are wholly or partly combinable which is generally applicable, particularly with any other embodiment described herein.

Figure 36:
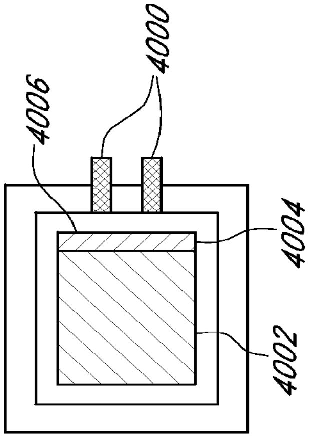
FIGS. 36-38 are schematic views of a moisture sensitive compression increasing seal, according to a generally applicable embodiment.
Figure 37:
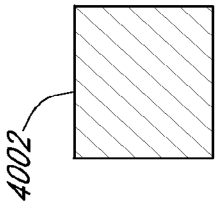
Figure 38:
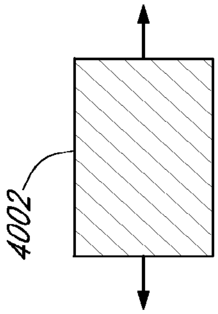

FIGS. 36-38 illustrate a two-part composite seal for sealing around the electrical contacts 4000 on the transmitter, which features are combinable, partly or wholly, with other embodiments described herein. In one form, the seal includes a liquid-activated expanding foam 4002 and a watertight sealing material 4004. The sealing material 4004 fills a leakage gap 4006. When the foam expands, as shown in the comparison of FIGS. 37 and 38, the leakage gap is sealed. In order to get a watertight seal, a small amount of compressive force may be applied to the foam. Due to tolerances of part fit and materials, it is impossible to guarantee a perfect fit in all configurations. This aspect translates to variations in sealing compressive force. The present embodiment works by the liquid-activated expanding foam increasing in thickness when exposed to water. This provides an additional gap-filling compressive force on the sealing surface material.

In some embodiments, the transmitter 500 includes contacts 505 that include a material which, despite being exposed to moisture, do not generate a substantial amount of electrochemical current. For example, carbon, a carbon embedded silicone elastomer, a conductive polymer, a conductive salt, and certain metals having the desired property may be used. In some embodiments, the sensor may include a similar material. Such materials reduce or eliminate current caused by an electrochemical reaction of the contacts with moisture or other contaminants.

Adhesive patch 485 is attached to the housing 480 and to liner 490. In some embodiments, the adhesive patch 485 is removably attached to the applicator base 465 on a first side with an adhesive which is weaker than the adhesive of the second, opposing, side for attaching to the host. Various adhesive patch embodiments described herein are combinable, partly or wholly, with other embodiments described herein. In some embodiments, the adhesive patch 485 is attached to a second liner, which is between the adhesive patch 485 and the applicator base 465. In some embodiments, the second liner is removable, for example after the applicator 400 has detached from the on-skin sensor assembly 600. The second liner may be removably attached to the applicator base 465 with an adhesive.

In some embodiments, the adhesive patch 485 includes an adhesive which is air permeable and waterproof or water resistant. In some embodiments, the adhesive patch 485 has a backing which is moisture permeable in the area where the sensor (discussed below) passes through the adhesive patch 485. In some embodiments, the adhesive patch 485 has a backing which is moisture impermeable in an area outside of the housing 480 and the transmitter 500. The adhesive of the adhesive patch 485 may be pressed onto the host after removal of the liner 490 by pressing on the applicator 400. In some embodiments, the applicator 490 has a surface which includes texture to aid in the application process. For example, ribs, bumps, or a rough surface may be included to allow for a firm grip on the applicator 490 to be established.

Figure 3B:
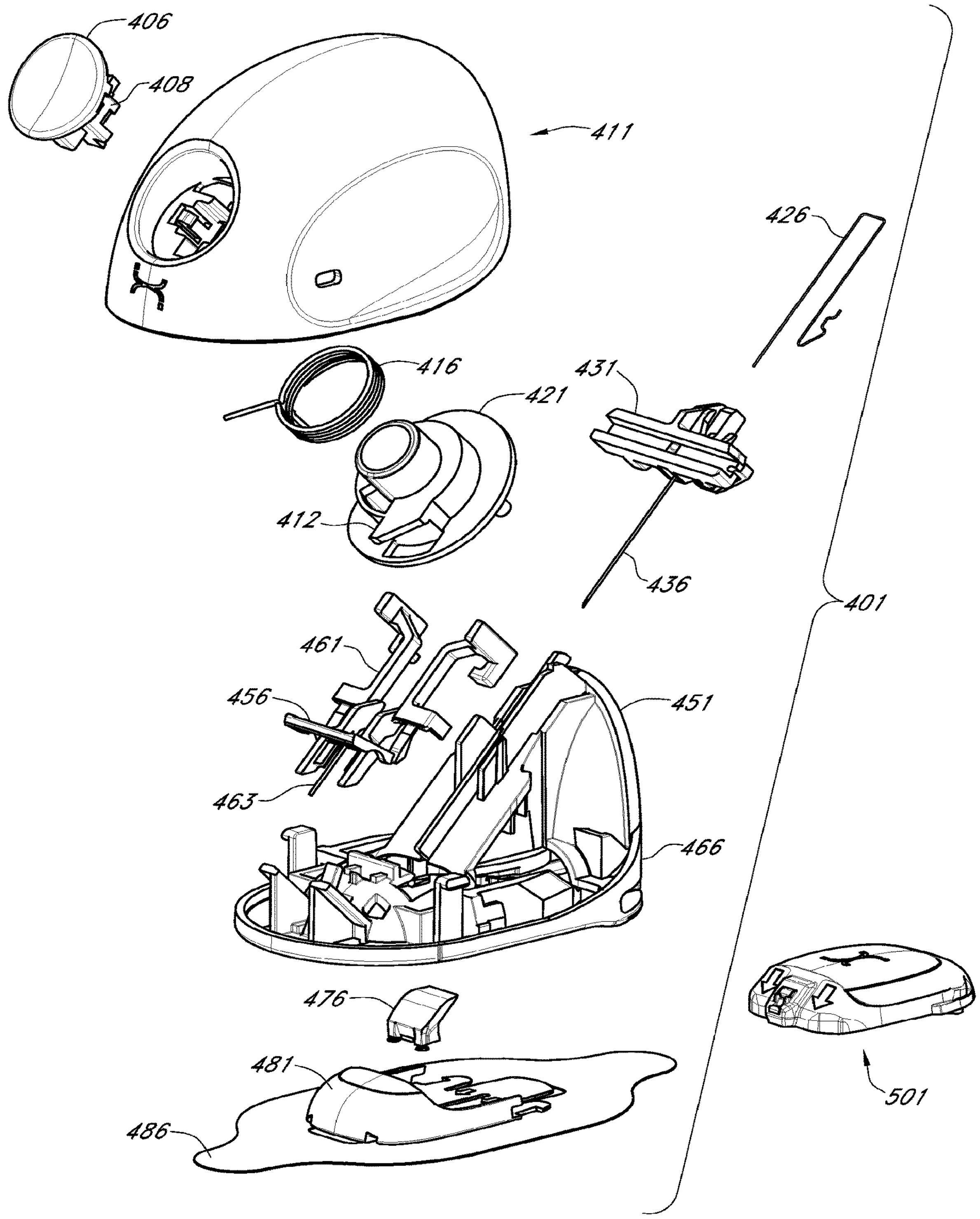
FIG. 3B is an exploded view of a generally applicable embodiment of a sensor system and applicator.
Figure 3C:
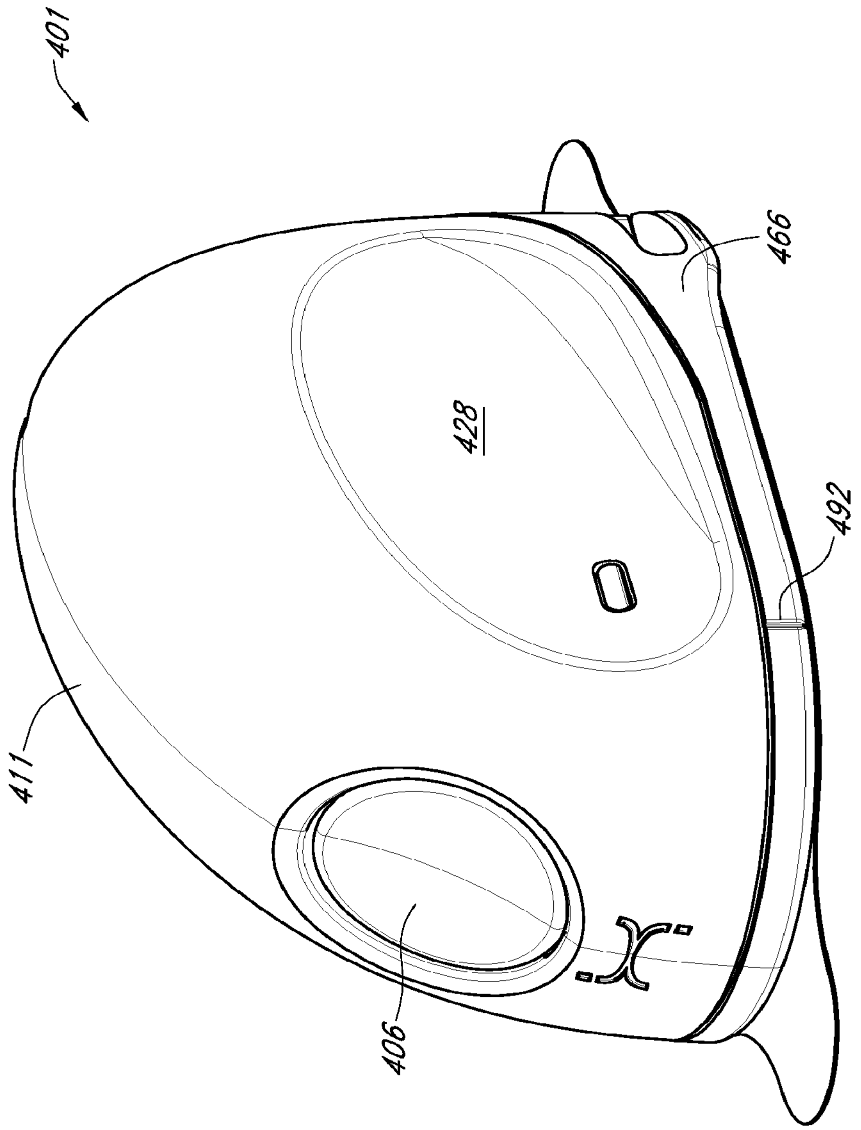
FIG. 3C is an assembled front perspective view of the sensor system and applicator of FIG. 3B.

FIG. 3B is an exploded view of another generally applicable embodiment of an applicator 401 and sensor system used in a process substantially the same as that shown in FIGS. 2A-2D, which embodiment is combinable, partly or wholly, with other embodiments described herein. FIG. 3C is a front perspective view of the sensor system and applicator of FIG. 3B. Other implementations may be used.

With reference to FIG. 3B, a trigger 406 is attached to a front cover 411, and is activated in order to actuate the applicator 401 to cause the applicator 401 to perform the various actions described below. Front cover 411 is connected to back cover 451, and front and back covers 411 and 451 cooperatively house a sensor insertion mechanism. The sensor insertion mechanism includes torsion spring 416, wheel 421, push rod 426, needle hub 431, and needle 436, in which the sensor (not shown) is held prior to activation of the trigger 406. In response to the trigger 406 being activated, the sensor insertion mechanism inserts the sensor into the host, as described below.

The front cover 411 may, for example, be constructed of any moldable plastic material, such as nylon, polyethylene, polyurethane, ethylene-vinyl acetate (EVA), polyether block amide (PEBAX), acrylonitrile butadiene styrene (ABS), polyether ether ketone (PEEK), polytetrafluoroethylene (PTFE), thermoplastic polyetherimide (ULTEM), or any other material. In some embodiments, the front cover 411 is constructed of polypropylene, which may provide desirable sound deadening characteristics when the sensor insertion mechanism is activated.

The applicator also includes a trigger lock 456, which prevents the trigger 406 from being activated until the transmitter 501 has been inserted so as to be at least partially seated in the housing 481. As discussed above and in further detail below, the transmitter 501 is at least partially seated in the housing 481 by inserting the transmitter 501 through the opening in the applicator 401, and is subsequently fully seated into the housing 481 in response to the trigger 406 being activated. A transmitter standoff 461 prevents premature seating of the transmitter 501 fully into the housing 481. Whereas in the embodiment of FIG. 3A the trigger lock 455 and the transmitter standoff 460 are separate pieces, in the embodiment of FIG. 3B these two components are combined into a unitary structure with the trigger lock 456 and the transmitter standoff 461 being connected by a living hinge (not shown) or other structure. The living hinge provides a spring return force when the trigger lock 456 is pivoted with respect to the transmitter standoff 461, as described in more detail below. Further, a cannula 463 extends from the transmitter standoff 461 and receives the needle 436 to provide additional column strength to the needle 436. The cannula 463 also isolates the needle 436 from the elastomeric seal 476, thus eliminating any potential of the needle 436 to drag broken-off portions of seal 476 into the body. It also eliminates any potential friction from the needle 436 sliding against or piercing through the seal 476.

The cannula 463 may be integral with the transmitter standoff 461, or a separate piece secured to the transmitter standoff 461. In one embodiment, the transmitter standoff 461 is a separate piece of stainless steel tubing. In some embodiments, the inner surface of the transmitter standoff 461 may include a lubricant to reduce friction with the needle 436 and the pushrod 426 when the applicator 401 is activated. For example, the lubricant may be a coating of polytetrafluoroethylene (PTFE), poly(p-xylylene) polymer, such as PARYLENE®, ethylene tetrafluoroethylene (ETFE), or silicone.

The back cover 451 includes a base 466 that receives the inserted transmitter 501. The base 466 also guides the transmitter 501 into the housing 481 as the transmitter 501 is inserted into the applicator 401.

In this generally applicable embodiment, the housing 481 includes an elastomeric seal 476 positioned within the housing 481 to engage the leading end of the transmitter 501. In response to the applicator 401 being actuated, the transmitter 501 is pressed against the elastomeric seal 476 with the sensor (not shown) between the elastomeric seal 476 and electrical contacts 506 of the transmitter 501 after the sensor has been inserted into the host.

In some embodiments, the transmitter 501 includes contacts 506 that include a material that, despite being exposed to moisture, do not generate a substantial amount of electrochemical current. For example, carbon, a carbon embedded silicone elastomer, a conductive polymer, a conductive salt, and certain metals having the desired property may be used. In some embodiments, the sensor may include substantially the same material. Such materials reduce or eliminate current caused by an electrochemical reaction of the contacts with moisture or other contaminants.

An adhesive patch 486 is attached to the housing 481. In some embodiments, the adhesive patch 486 is removably attached to the applicator base 466 on a first side with an adhesive that is weaker than the adhesive of the second, opposing, side for attaching to the host. In some embodiments, the adhesive patch 486 is attached to a second liner, which is between the adhesive patch 486 and the applicator base 466. In some embodiments, the second liner is removable, for example after the applicator 401 has detached from the on-skin sensor assembly 600. The second liner may be removably attached to the applicator base 466 with an adhesive.

In some embodiments, the adhesive patch 486 includes an adhesive that is air permeable and waterproof or water resistant. In some embodiments, the adhesive patch 486 has a backing that is moisture permeable in the area where the sensor (discussed below) passes through the adhesive patch 486. In some embodiments, the adhesive patch 486 has a backing that is moisture impermeable in an area outside of the housing 481 and the transmitter 501. The adhesive of the adhesive patch 486 may be pressed onto the host by pressing on the applicator 401. In some embodiments, the applicator 401 has a surface that includes texture to aid in the application process. For example, ribs, bumps, or a rough surface may be included to allow for a firm grip on the applicator 401 to be established.

In a generally applicable embodiment (i.e. independently combinable with any of the aspects or embodiments identified herein), with reference to FIG. 3C, the applicator 401 may comprise one or more features that make the applicator 401 easier to use and/or more ergonomic than previous applicators. For example, the illustrated embodiment of the button 406 has a concave outer surface, making it easy to locate with one's finger without even having to look. The surface may also have a different texture than the front cover 411. For example, the button 406 may be stippled or roughened while the front cover 411 is smooth, or vice versa. The button 406 may also be a different color than the front cover 411, such as a sharply contrasting color, thereby making it easier to distinguish visually from the front cover 411.

The illustrated embodiment of the front cover 411 is ergonomically shaped, substantially the same as a computer pointing device (mouse), in a manner that allows it to fit comfortably in the palm of the user's hand. For example, the front cover 411 has a domed or convex upper surface that creates a large surface area for contacting the user's palm, and concave portions 428 on opposite sides that receive the user's thumb on one side and fingers on the other side, both of which features strengthen the user's grip on the applicator 401. For increased grip, the concave portions 428 may also be textured, such as stippled or roughened, as described with respect to the button 406.

The ergonomic shape of the applicator 401 provides at least one additional benefit beyond making the applicator 401 easier and more comfortable to grip. For example, many applicators for continuous analyte sensors that are on the market today have an appearance that resembles a syringe. These applicators include a tubular portion that houses a piston-type drive that propels the needle to implant the sensor under the skin. Patients with diabetes understand that many syringes include needles, and needles evoke memories of oftentimes painful finger pricks to obtain blood samples and/or sensor implantations that may also be painful. Thus, the syringe-like appearance of many applicators may make them less attractive to patients. The present embodiments solve this problem by providing an overall appearance that resembles a computer mouse more than a syringe.

Figure 9A:
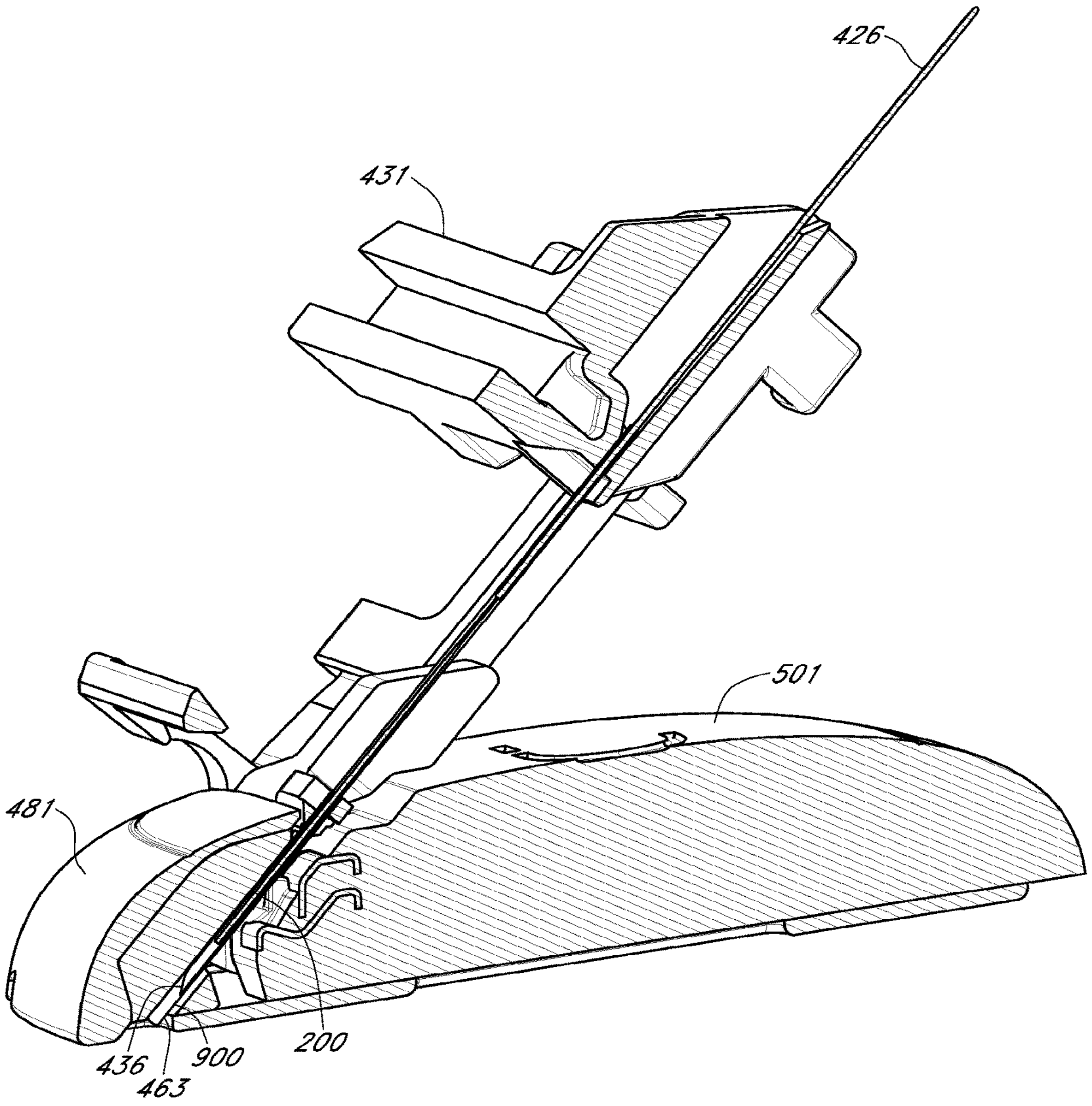
FIGS. 9A-9E are front perspective cross-sectional views of the applicator and sensor system of FIG. 3B at various stages in a method of applying the sensor system, showing actuation of a needle carrying the sensor and engagement of a proximal end of the sensor with contacts on a transmitter of the sensor system.
Figure 9A:
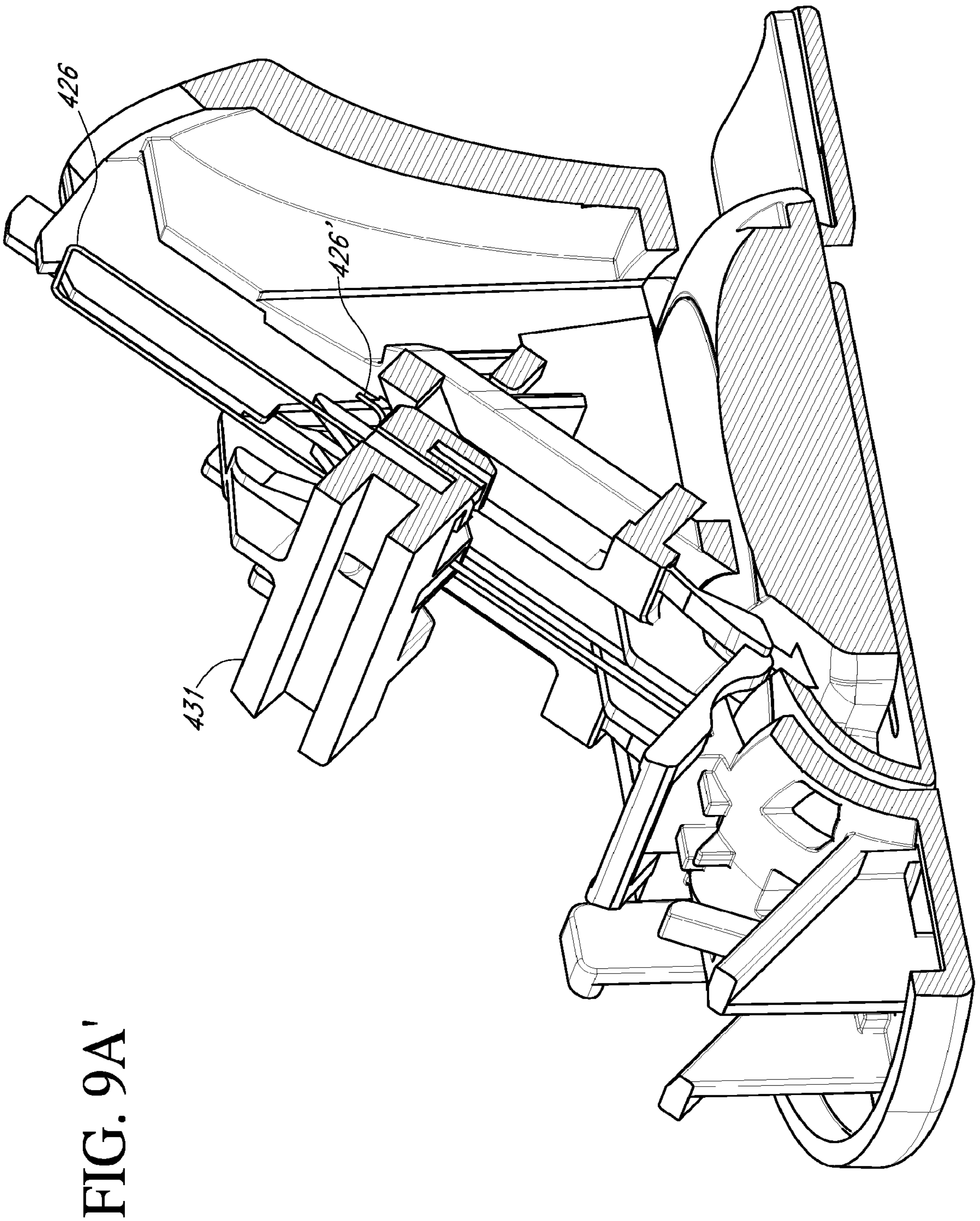

Also as shown in FIG. 3C, one or more embodiments of the present applicators may include score marks 492 on opposite sides of the base 466. The score marks 492 are substantially aligned with the lower end of the cannula 463 (FIG. 9A). The lower end of the cannula 463 is where the needle exits during the sensor insertion process, and thus substantially corresponds with the location on the host's skin where the sensor will be implanted. Thus, the score marks 409 assist the host in identifying exactly where the sensor will be placed in the skin. This aspect is advantageous, as the host may prefer to vary the location of the sensor from one implantation to the next so as to avoid irritating any one area of the skin.

Figure 4:
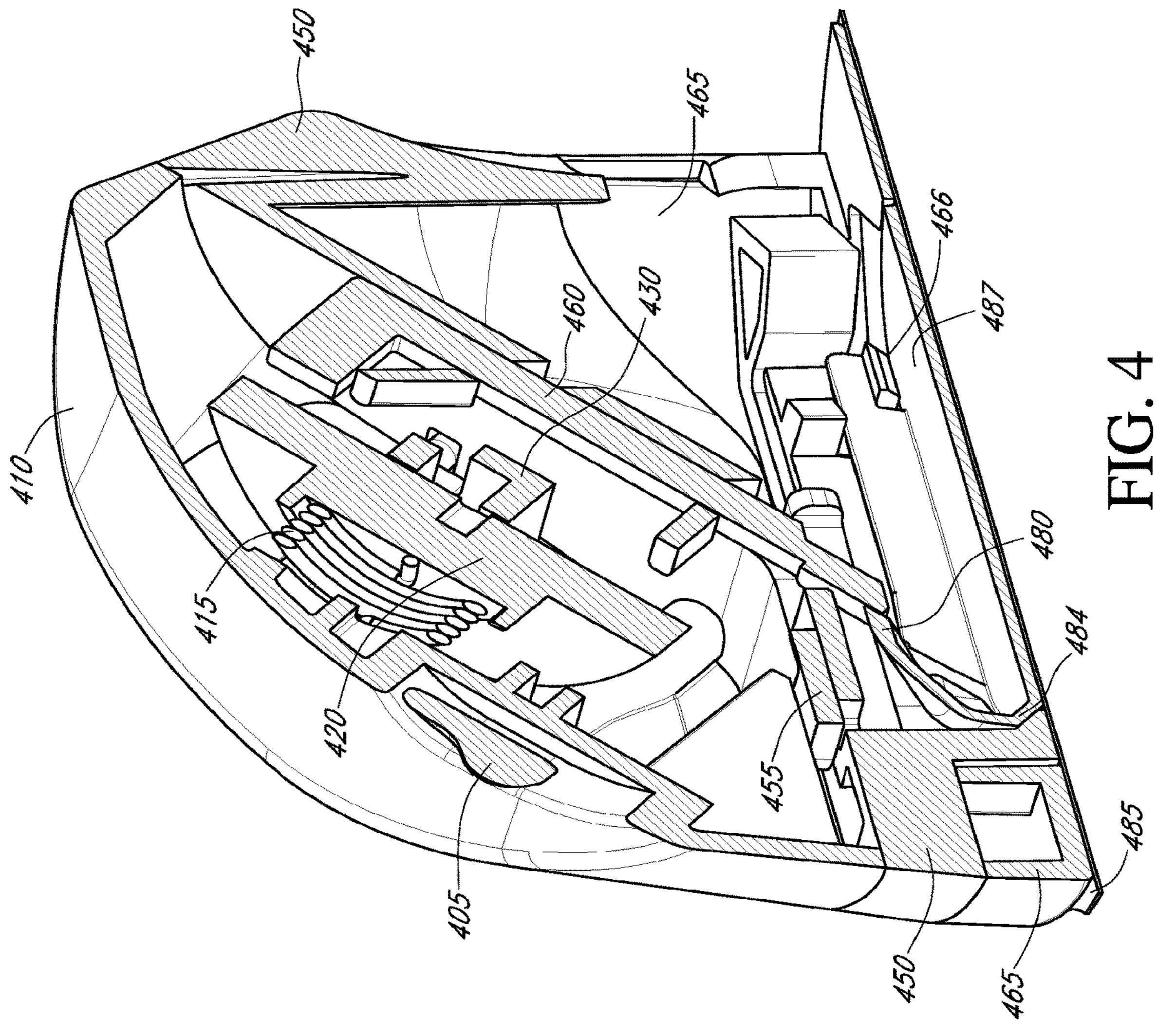
FIG. 4 is a side cross-sectional view of the applicator of FIG. 3A.

FIG. 4 is a cross-sectional view of the applicator of FIG. 3A prior to insertion of the transmitter 500, which embodiment is combinable, partly or wholly, with other embodiments described herein. In one form, automatic release of the applicator from the housing after sensor insertion and transmitter seating is provided. This figure illustrates the mechanisms for attachment of the applicator to the housing as shipped to the patient, or prior to the automatic release resulting from sensor insertion. As illustrated, the back cover 450 holds a nose 484 of the housing 480 and the projection 466 on the applicator snap arms 495 hold a tail 487 of the housing 480.

As shown, the front cover 410 is connected with the back cover 450. The front cover 410 and the back cover 450 form a cavity having the sensor insertion mechanism therebetween. As discussed above the sensor insertion mechanism includes torsion spring 415, wheel 420, push rod 425, needle hub 430, and needle 435. Push rod 425, needle hub 430, and needle 435 are not shown in FIG. 4 because they are not in the illustrated plane of the cross-section of the applicator.

A portion of trigger 405 is shown in a cavity of the front cover 410, and a portion of trigger lock 455 is shown within the front and back covers 410 and 450. The trigger locking function of the trigger lock 455 is not represented in this figure because the portions of the trigger 405 and the trigger lock 455 related to the function are not in the illustrated plane of the cross-section of the applicator.

Applicator base 465 is connected to the bottom portion of the back cover 450, and housing 480 is held in the applicator by the back cover 450 and projections 466 of the snap arms 495 in the applicator base 465. Optionally, adhesive patch 485 is attached to the housing 480, but is not attached to the applicator base 465 or the back cover 450. Elastomeric seal 475 is not shown because it is not in the illustrated plane of the cross-section of the applicator. Furthermore, liner 490 is not shown as it has been removed.

In some embodiments, the applicator includes a mechanism that creates a seating force, which pulls the transmitter 500 into the partially seated position within the housing 480. For example, the applicator may apply a seating force to the transmitter 500 to hold the transmitter 500 in a partially seated position within the housing 480 of the applicator during sensor insertion. The transmitter seating force may be about 0.25 lbs. to about 3 lbs, for example, while a sealing force, which is applied to the sensor after the applicator trigger 406 is activated, may be at least two times more than the transmitter seating force, such as 3×, 4×, 5×, 10×, 15×, 20×, etc. The applicator prevents the transmitter 500 from becoming fully seated within the housing 480 until after sensor insertion. The fully seated position within the housing 480, which occurs after sensor insertion, provides for an electrical connection of the sensor with the transmitter 500 and a seal 475 of the electrical connection. This configuration advantageously allows the transmitter 500 to be pre-seated (partially seated) by a user prior to sensor insertion, for example before the assembly is placed on a position on the body that may be difficult to reach, and ensures that a seal is formed at the electrical connection of the sensor with the transmitter 500, which is fully seated only after sensor insertion.

Figure 5A:
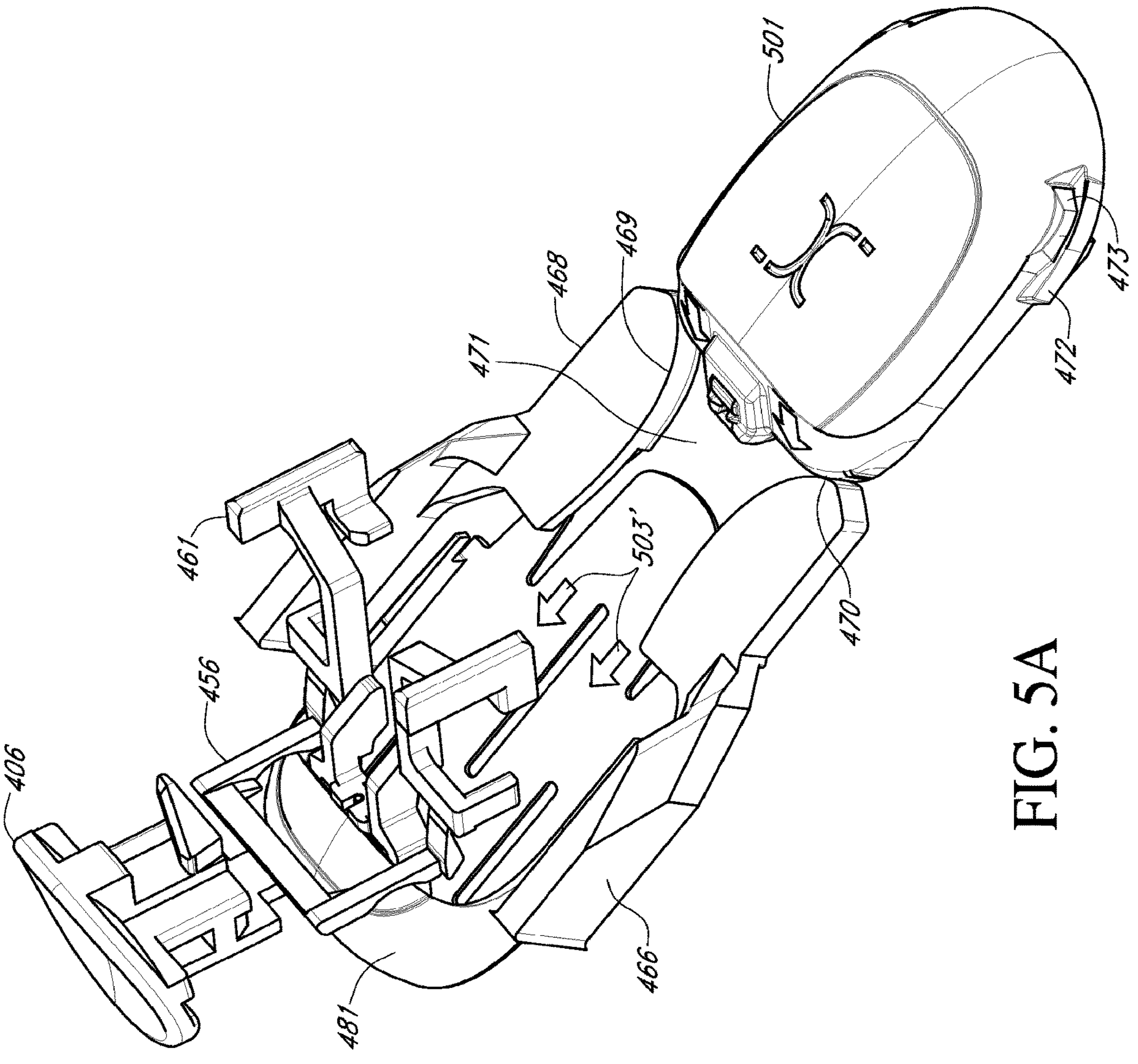
FIGS. 5A-5C are rear perspective views of select components of the applicator of FIG. 3B, showing a process for inserting the sensor system into the applicator.
Figure 5B:
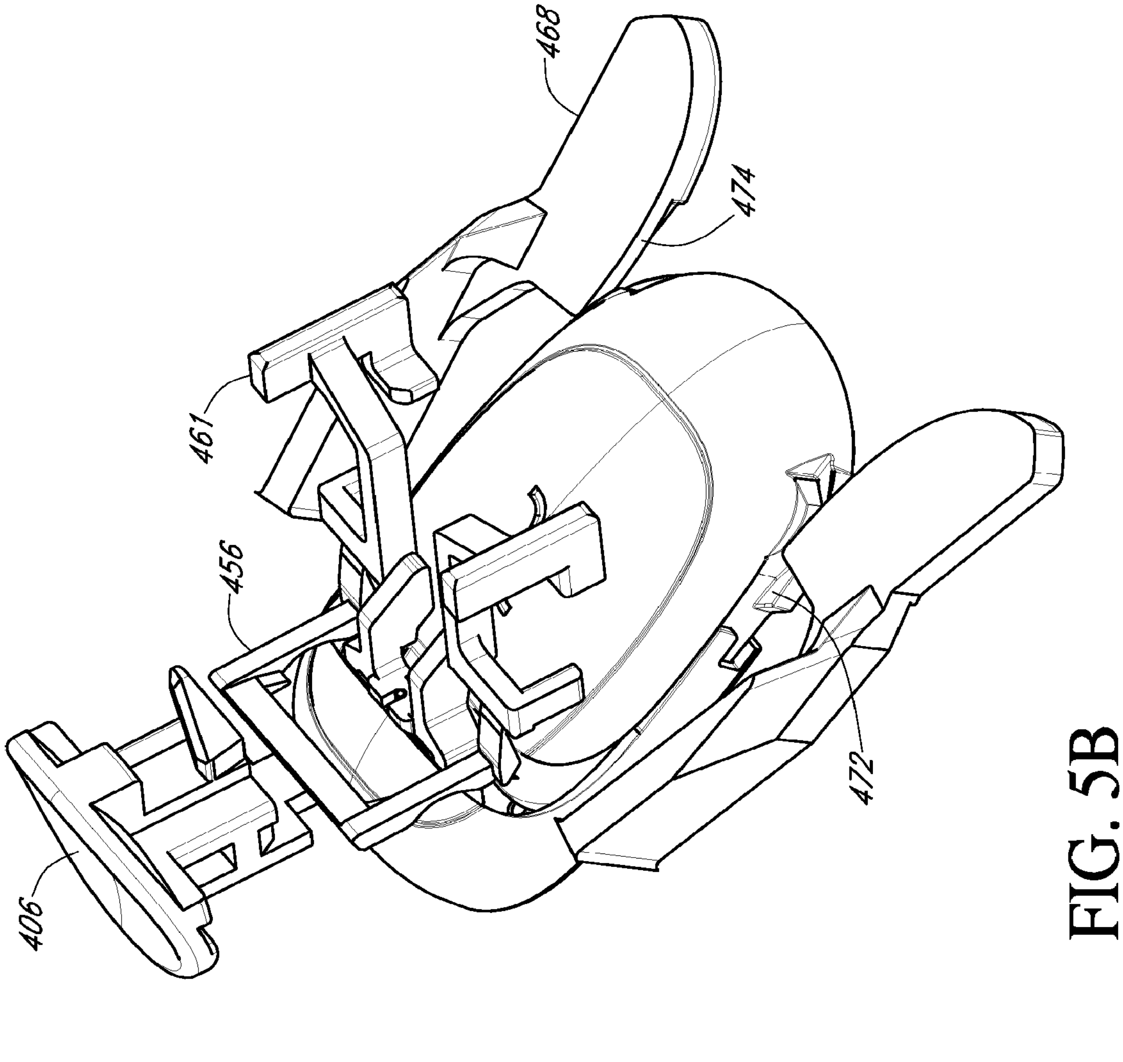
Figure 5C:
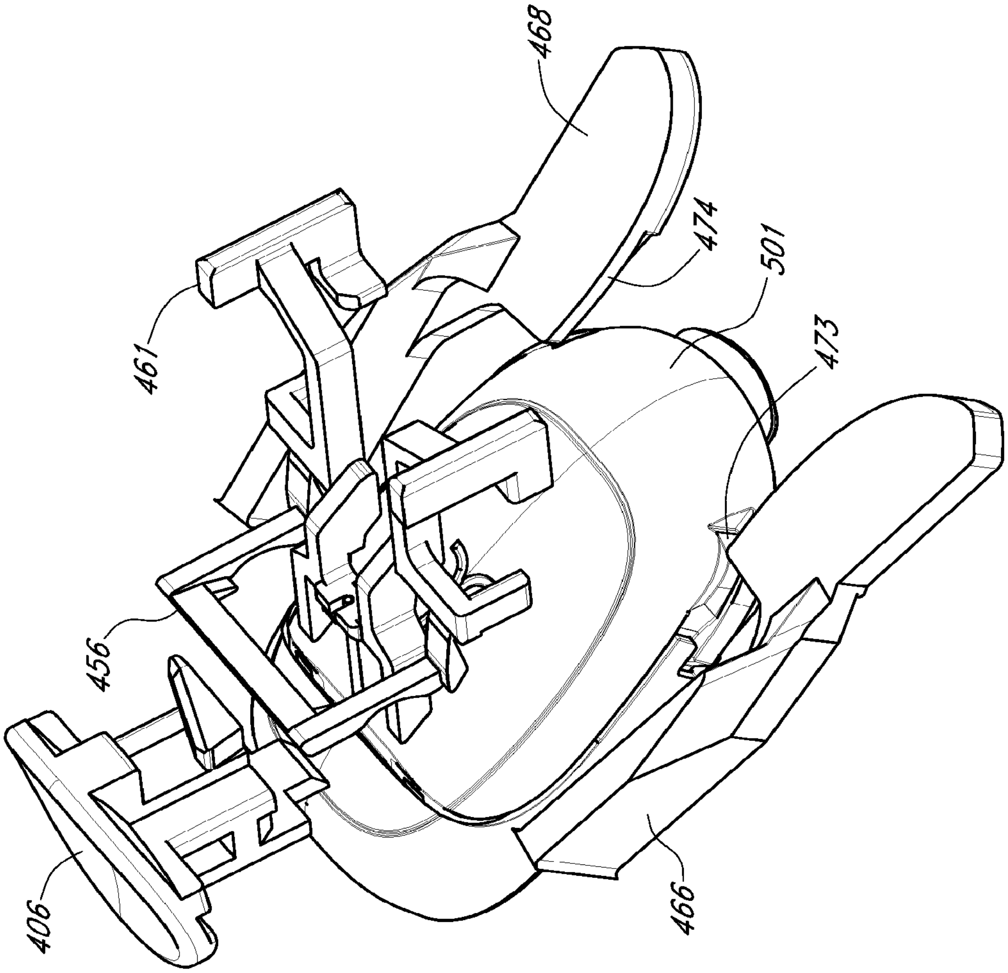

FIGS. 5A-5C are rear perspective views of select components of the applicator 401 at progressive stages in a method of inserting the transmitter 501 into the applicator 401 in one generally applicable embodiment, which is combinable, partly or wholly, with other embodiments described herein. For clarity, and with reference to FIG. 5A, only the following components are shown: the trigger 406, the trigger lock 456, the transmitter standoff 461, portions of the base 466, the housing 481, and the transmitter 501.

In some embodiments in which the system is designed for pre-seating of the transmitter prior to activation of the trigger (and subsequent sensor insertion and automatic full transmitter seating), a mechanism may be provided that prevents the trigger 406 from being actuated prior to partial seating of the transmitter 501 within the housing 481. The mechanism is designed to avoid user error, wherein if a user were to forget to pre-seat the transmitter 501 prior to actuating the trigger 406, the sensor would be inserted, but the transmitter would not be automatically fully seated. Accordingly, the trigger lock 455 is provided to prevent the trigger 406 from being actuated prior to the transmitter 501 being partially seated in the housing 481. In the illustrated embodiment, upon pre-seating (partial seating), the transmitter 501 engages the trigger lock 456, which disengages the trigger lock 456 from the trigger 406, allowing the trigger 406 to actuate. This process is described in further detail below. Also, in some embodiments, design modifications that achieve the same result could be used.

At the point of the application process shown in FIG. 5A, the transmitter 501 is poised for insertion into the base 466 and the housing 481. Rounded corners 470 at the leading end of the transmitter 501 contact rounded inner end surfaces 469 of a pair of spring arms 468 that are integrated into the base 466. A gap 471 between the spring arms 468 is narrower than a width of the transmitter 501. Thus, as the transmitter 501 is advanced into the base 466, the rounded corners 470 bear against the rounded inner end surfaces 469 and force the spring arms 468 apart. Corners at the trailing end of the transmitter 501 include protruding tabs 472 and recesses 473 that engage the spring arms 468 as the transmitter 501 advances farther into the base 466, as described further below. A height of each of the tabs 472 is less than a height of the transmitter 501, and the tabs 472 are located toward the lower surface of the transmitter 501.

With reference to FIG. 5B, each of the spring arms 468 includes an undercut portion 474 having a recess beneath. Further, a height of each of the tabs 472 is less than a height of the transmitter 501, and the tabs 472 are located toward the lower surface of the transmitter 501. Thus, as the transmitter 501 advances through the position shown in FIG. 5B, the tabs 472 pass through the recesses beneath the undercut portions 474. At this stage, the undercut portions 474 bear down on the tabs 472. Thus, as the tabs enter the recesses beneath the undercut portions 474, the force profile on the transmitter 501 transitions from a lateral squeezing force to a combination of lateral squeezing and downward (toward the host's skin) force. Also, as the rounded inner end surfaces 469 of the spring arms 468 wrap around the cammed surfaces of the transmitter, the seating force engages and pushes the transmitter forward.

With reference to FIG. 5C, with further advancement of the transmitter 501, eventually the undercut portions 474 come to rest in the recesses 473 at the trailing corners of the transmitter 501. As the undercut portions 474 enter the recesses 473, the stored spring force in the spring arms 468 relaxes slightly as the spring arms 468 move toward one another. This movement generates a force in the direction of advancement of the transmitter 501 as the undercut portions 474 bear on rearward facing surfaces of the recesses 473. This force not only draws the transmitter 501 into the housing 466, but also aids in retaining the transmitter 501 within the housing 466. And, in the position of FIG. 5C, the transmitter 501 is prevented from further inward movement because it contacts the transmitter standoff 461, which is in a fixed position within the applicator 401. Thus, at the point of the application process shown in FIG. 5C, the transmitter 501 is held in place by the spring arms 468 and transmitter standoff 461, whereby the transmitter is "partially seated" within the housing 481. In some embodiments, other means of drawing the transmitter 501 into the housing 466 may be used in place of, or in addition to, the spring arms 468. For example, one or more magnets may be positioned on or within the housing 481 and/or the transmitter 501.

Further, as the transmitter 501 advances from the position of FIG. 5B to the position of FIG. 5C, it contacts the trigger lock 456, causing the trigger lock 456 to pivot upward with respect to the transmitter standoff 461 and moving out of the path of the trigger 406. The trigger 406 is thus armed and the applicator 401 is ready to fire. If the transmitter 501 is subsequently backed out of the housing 481, the trigger lock 456 may advantageously pivot back to its original position under the influence of a return spring force, gravity, etc. For example, the trigger lock 456 may be attached to the transmitter standoff 461 with a living hinge that creates the return spring force. This feature relocks the trigger 406 to prevent accidental firing.

In some embodiments, the applicator 401 provides one or more tactile, auditory, or visual indications that the transmitter 501 has been properly inserted into the applicator 401. For example, the transmitter 501 being drawn in indicates that the applicator 401 has received the transmitter 501 to the extent permitted by the transmitter standoff 461. In addition, because the transmitter standoff 461 prevents further forward movement of the transmitter, the transmitter 501 cannot be further advanced. In some embodiments, the drawing in of the transmitter 501 causes an audible click. In some embodiments, the applicator 401 has an opening so that the inserted transmitter 501 is visible through the opening once inserted. The transmitter 501 may have a mark, which, when visible through the opening indicates that the transmitter 501 is properly inserted into the applicator 401. Similarly, the position of the drawing mechanism may be visually indicated so as to indicate proper insertion.

In certain embodiments, contours of the transmitter 501 and the spring arms 468 are tailored to provide a constant insertion force. That is, as the user is inserting the transmitter 501, the amount of force applied to the transmitter 501 is constant from the beginning of the process to the end. This aspect provides a smooth insertion process that aids in preventing misalignment or breakage.

Further, contours of the transmitter 501 and the spring arms 468 may be tailored to reduce the insertion force that the user must apply to partially seat the transmitter while at the same time increase the sealing force between the seal 476 and the sensor 200. In one embodiment, the insertion force necessary to partially seat the transmitter may be about 0.25 lbs. to about 3 lbs., such as about 0.5 lb. or 1 lb., while the sealing force may be up to 20 times greater than the insertion force, such as 2-3 times greater.

In some embodiments, the spring arms 468 may be pre-loaded with stored energy, and partially seating the electronics unit within the housing releases the stored energy. Also in some embodiments, the spring arms 468 may be pre-loaded with stored energy, and activating the trigger 406 releases the stored energy.

Figure 5D:
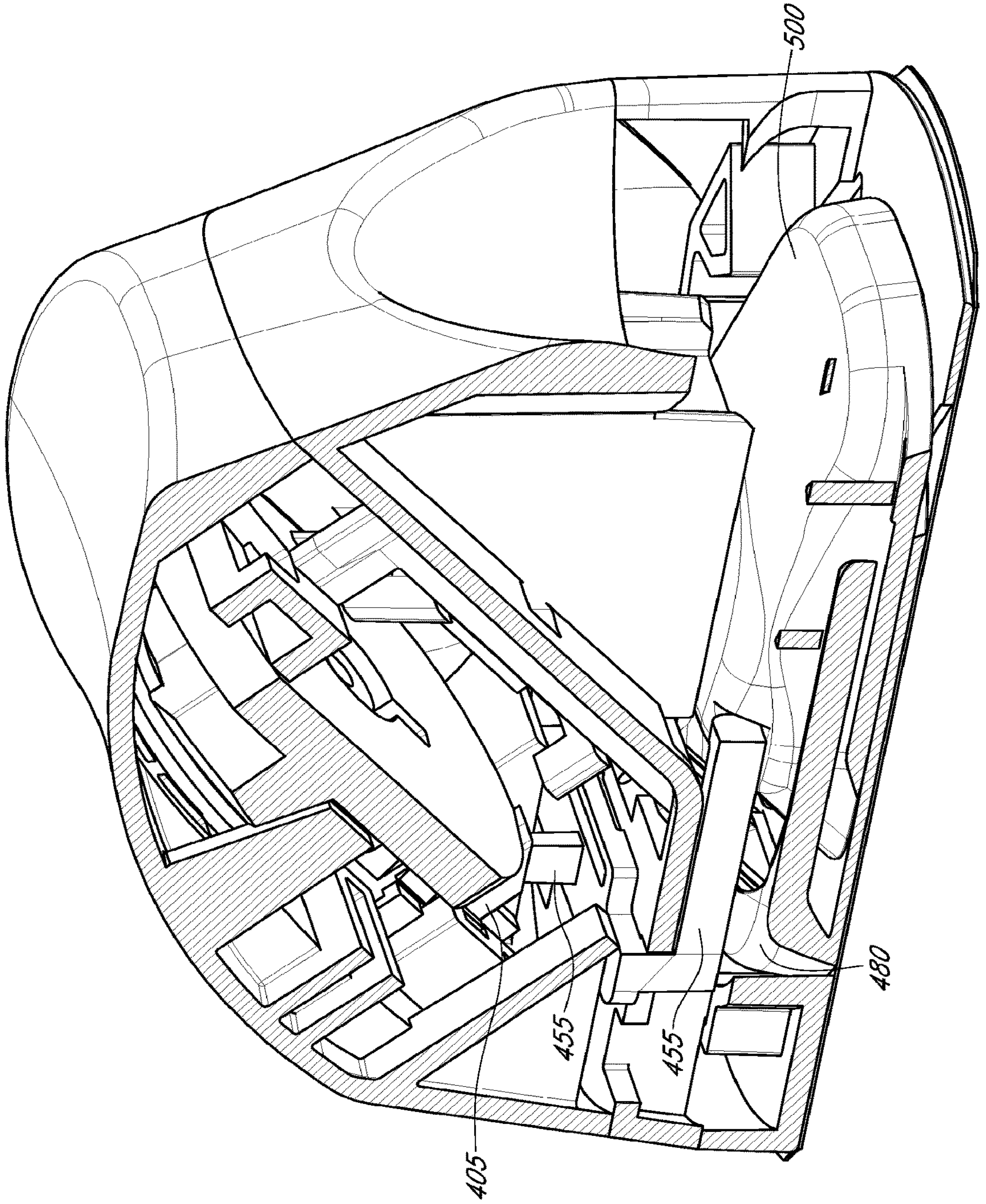
FIGS. 5D and 5E are rear cross-sectional perspective views of the applicator of FIG. 3A during insertion of the transmitter.
Figure 5E:
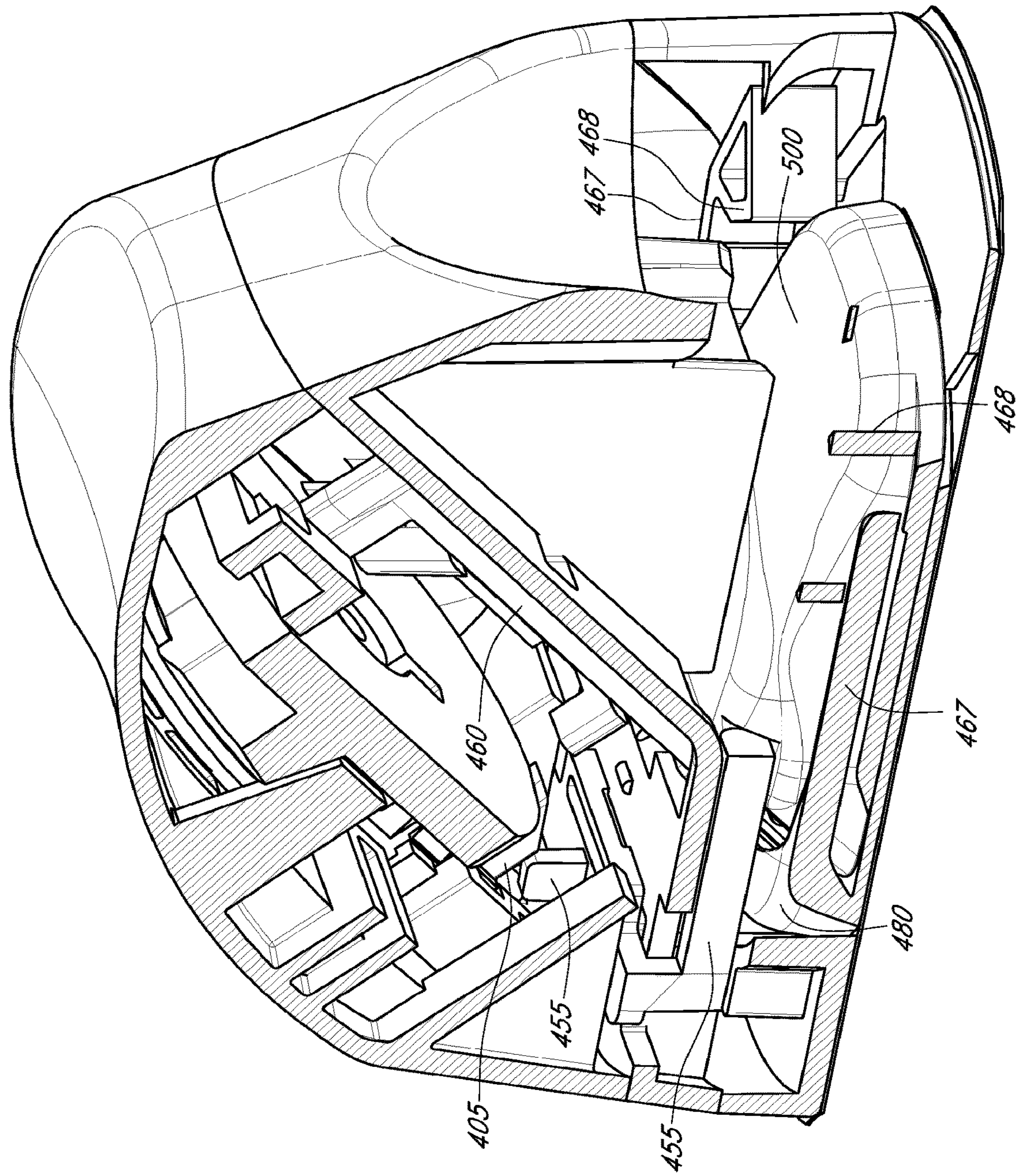

FIGS. 5D and 5E are rear cross-sectional perspective views of the applicator 400 of FIG. 3A during insertion of the transmitter 500, and illustrate a generally applicable embodiment, which is combinable, partly or wholly, with other embodiments described herein. These views show an embodiment of the trigger lock 455 movement as a result of inserting the transmitter 500 into the applicator 400. As the transmitter 500 is drawn into the applicator 400, prior to engaging the transmitter standoff 460, the transmitter 500 engages the trigger lock 455. Further movement of the transmitter 500 until engaging the transmitter standoff 460 causes the trigger lock 455 to change positions. In the new position, the trigger lock 455 no longer prevents the trigger 405 from being activated. Accordingly, once the transmitter 500 is inserted into the applicator, the applicator 400 may be actuated by the trigger 405.

FIG. 5D shows the applicator 400 with the transmitter 500 partially inserted therein (but not partially seated). The transmitter 500 has engaged the trigger lock 455, but has not yet engaged the transmitter standoff 460. The trigger lock 455 has not been moved and engages the trigger 405 so as to prevent the trigger 405 from moving. Accordingly, the trigger 405 cannot be activated.

FIG. 5E shows the applicator 400 with the transmitter 500 partially seated within the housing 480. In this position, the transmitter 500 is pressed against the transmitter standoff 460 by the contact projections 468 on the spring arms 468. As shown, the trigger lock 455 has been moved by the transmitter 500, and no longer prevents the trigger 405 from being activated. It should be noted that although one embodiment of a sliding switch trigger is shown, a variety of mechanisms, including push buttons, rotating triggers, or the like, that can be configured to initiate the sensor insertion described herein, can be used with the embodiments herein.

Referring now to sensor insertion, following actuation of the trigger 406, an example embodiment of a sensor insertion mechanism is described below. The sensor insertion mechanism is a scotch yoke that converts rotational motion of the wheel 421 into linear motion of the needle hub 431 suitable to insert the needle 436 and the sensor through the skin of the host, and to subsequently retract the needle 436 back into the applicator 401, leaving the sensor under the skin, all in one continuous motion. This design is particularly advantageous in reducing the number of complex parts often seen with prior art devices, and further provides a smooth and controlled sensor insertion and needle removal process. However, other sensor insertion mechanism designs can be used instead of or combined with other aspects of the system described herein.

FIGS. 6A-6D are front perspective views of select components of the applicator 401 of FIG. 3B at progressive stages in a method of activating the trigger 406 and inserting the needle 436 and the sensor into the host. For clarity, and with reference to FIG. 6A, only the following components are shown: the wheel 421, the pushrod 426, the needle hub 431, the trigger lock 456, the transmitter standoff 461, and portions of the base 466.

Figure 6A:
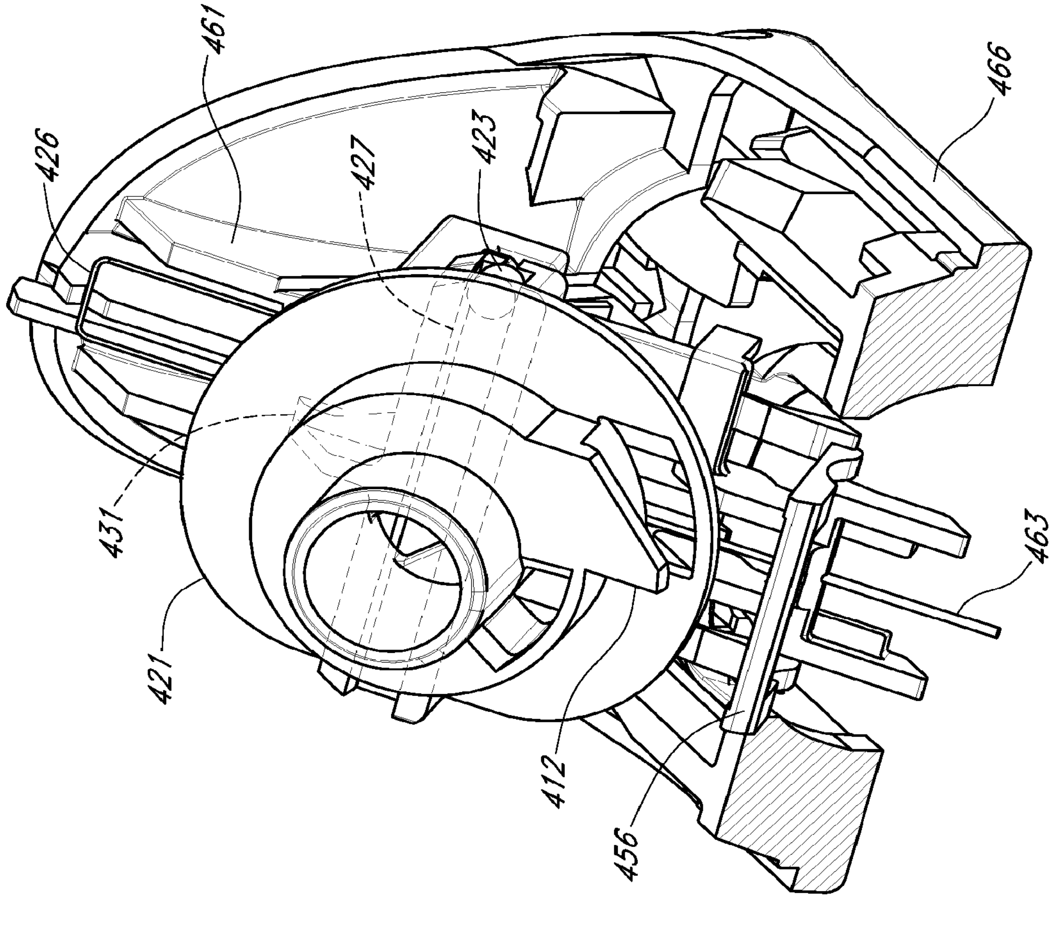
FIGS. 6A-6D are front perspective views of selected components of the applicator of FIG. 3B, showing a process for inserting the sensor into the host.

FIG. 6A shows the applicator 401 as it appears with the transmitter 501 partially seated in the housing 481 prior to the trigger 406 being activated. For clarity, the housing 481 is not shown in FIGS. 6A-6D. As shown in FIG. 6A, the trigger lock 456 is pivoted upward by contact with the transmitter 501 so that it does not prevent activation of the trigger 406. In this position, the torsion spring 415 (not shown in FIGS. 6A-6D) applies a torque to the wheel 421, which applies a linear force to the needle hub 431 because a tab 423 on the backside of the wheel 421 resides in a channel 427 of the needle hub 431. However, the trigger 406, having not been activated, prevents the wheel 421 from rotating. With reference to back to FIG. 3B, an underside of the trigger 406 includes a tab 408 that bears against a flange 412 on the wheel 421, thereby preventing rotation of the wheel 421 until the trigger 406 is activated. A surface of the tab 408 that bears against the flange 412 has a predetermined angle that causes the spring-loaded wheel 421 to apply an outwardly directed preload to the button 406. The preload reduces play in the button 406 that might result from manufacturing tolerances, and also reduces the chances of the applicator 401 misfiring. In one embodiment the preload force may be about 0.5-5 lbs., such as about 2-3 lbs.

Figure 6B:
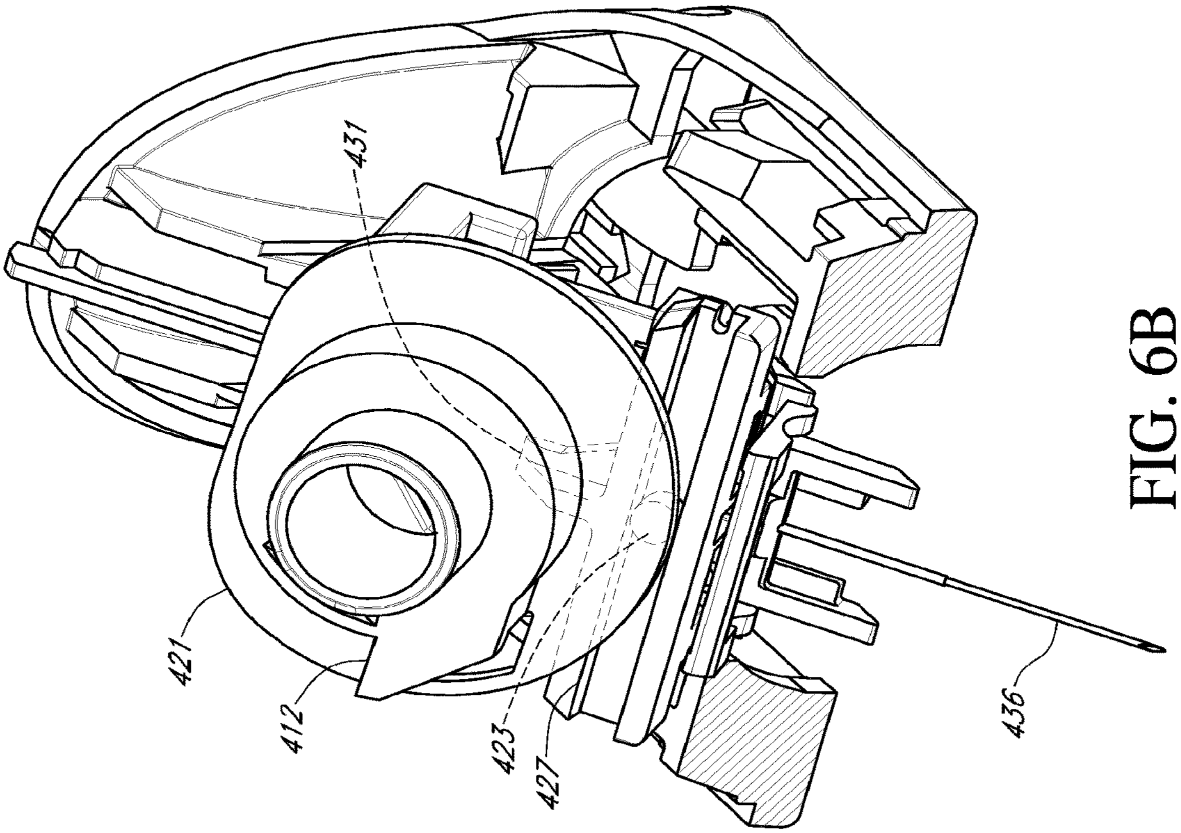

FIG. 6B shows the applicator 401 and the sensor insertion mechanism after the trigger 406 has been activated and while the wheel 421 is rotating. The host activates the trigger 406 by pushing it inwardly with respect to the front cover 411 (FIG. 3B). This motion is in contrast to the embodiment of FIG. 3A, in which the trigger 405 is activated by sliding it parallel to a front surface of the front cover 410. Once the trigger 406 is pushed, the tab 408 on the underside of the trigger 406 moves to a position below a plane of the flange 412 so that the wheel 421 is free to rotate in response to the torque applied by the torsion spring 415. As the wheel 421 rotates, the tab 412 applies a downward linear force to the needle hub 431 via the channel 427. As shown, the needle hub 431 and the needle 435, which is connected to the needle hub 431, have changed positions as a result of the wheel 421 rotating about 90°. During this rotation, the tab 412 slides across the channel 427 as the needle hub 431 moves downward. As shown, the needle 435, containing the sensor, is extended. The position of the needle hub 431 and the needle 435 in FIG. 6B represents the maximum extension of the needle 435. If the housing 481 were attached to a host, the needle 435 would be penetrating the skin of the host to insert the sensor into the host.

In order to ensure successful insertion despite different tissue types and manufacturing variability, the torsion spring 416 preferably provides enough torque to cause the needle 435 to accelerate to a velocity higher than desired for some hosts. However, under some circumstances, excessive velocity can cause unnecessary tissue damage. Thus, in some embodiments a speed regulator may be included.

For example, in some embodiments the velocity of the needle can be reduced by determining an appropriate mass of the needle hub, or another element that moves with the needle. In other embodiments, a flywheel may be used. In still other embodiments, movement of the sensor insertion mechanism may include a piston slidably engaged in a chamber, where the chamber has an aperture allowing a fluid, such as air, to enter or exit the chamber to facilitate movement of the piston. The relative sizes of the piston, chamber, and aperture can be selected to cause the needle to have a desired maximum velocity for the torque of the spring and the mass of the load. In some embodiments, a speed governor with feedback control may be used. For example, an air paddle or propeller may be connected to the needle hub such that as insertion velocity increases, air resistance increases. A centrifugal brake may be used, where weights are attached to an axle rotating at a speed proportional to the velocity of the needle by a flexible tether. As the velocity increases the weights are forced farther away from the axle and closer to a frictional surface. With sufficient velocity, the weights rub against the frictional surface, limiting the rotational velocity of the axle and also the velocity of the needle.

Figure 6C:
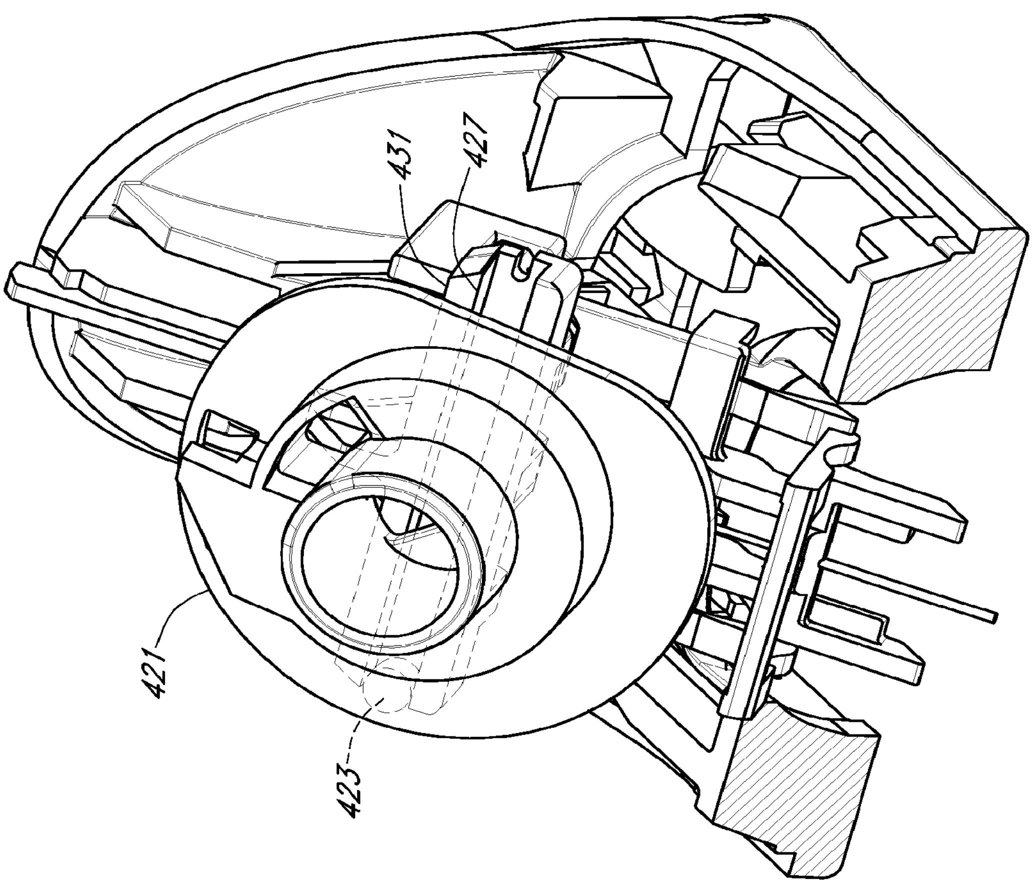

FIG. 6C shows the applicator 401 with the wheel 421 having rotated about 180° after the trigger 406 has been activated. In this position, the needle hub 431 has moved back up and away from the host's skin as the tab 423 moves further to the left in the channel 427 and continues to impart linear motion to the needle hub 431 as the wheel 421 rotates. In FIG. 6C, the wheel 421 is still rotating, but the needle 435, still attached to the needle hub 431, has been retracted and is within the applicator 401. The sensor 200, however, remains in the host because of the pushrod 425. The function of the pushrod 425 is explained in more detail below.

Figure 6D:
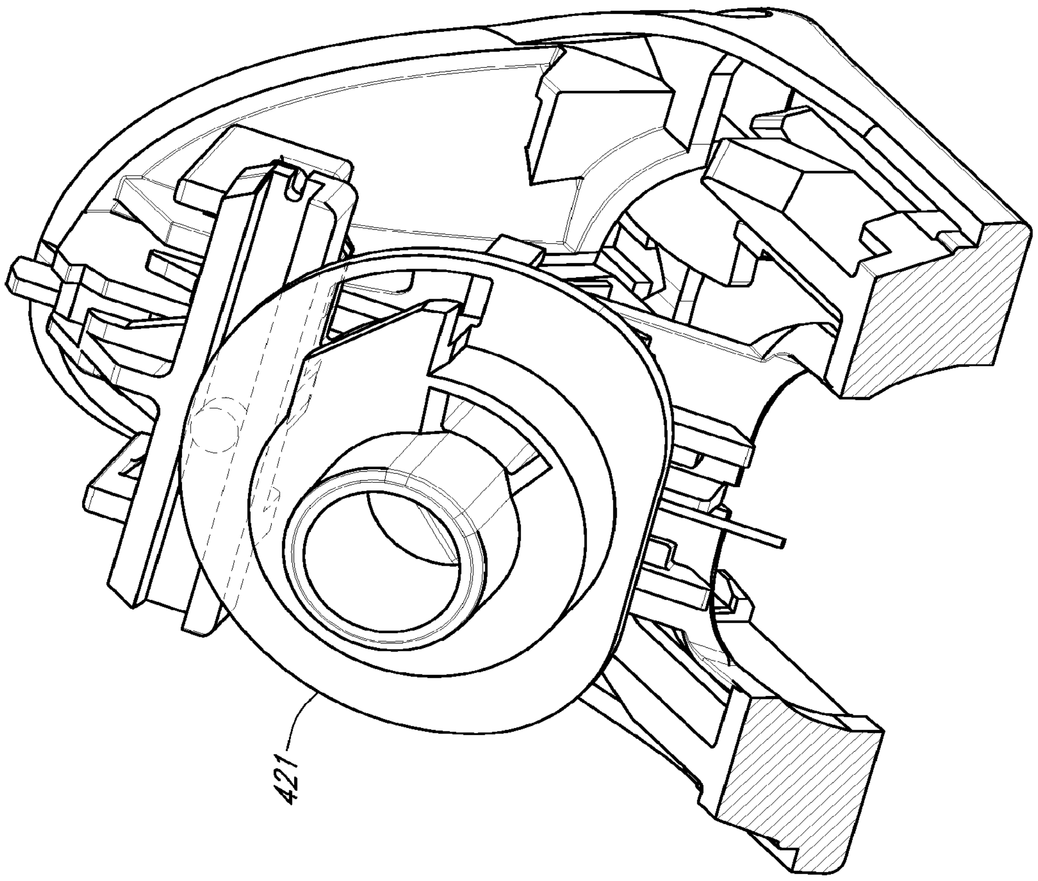

FIG. 6D shows the applicator 401 with the wheel 421 having rotated about 270° after the trigger 406 has been activated. This is the final resting position of the wheel 421. For example, there may be a hard stop that the wheel contacts to interrupt its rotation. Further, as described in more detail below, during this step, the transmitter standoff 461 moves to allow the transmitter 501 to advance into the housing 481.

In the above embodiment, full seating of the transmitter 501 within the housing 481 occurs as part of the sensor insertion process. In some embodiments, the transmitter 501 may be engaged with the housing 481 after the sensor has been implanted within the host. For example, the applicator may not include a provision for receiving the transmitter 501. After the sensor has been inserted and the housing attached to the host, the host may engage the transmitter with the housing to complete the application process.

Figure 7:
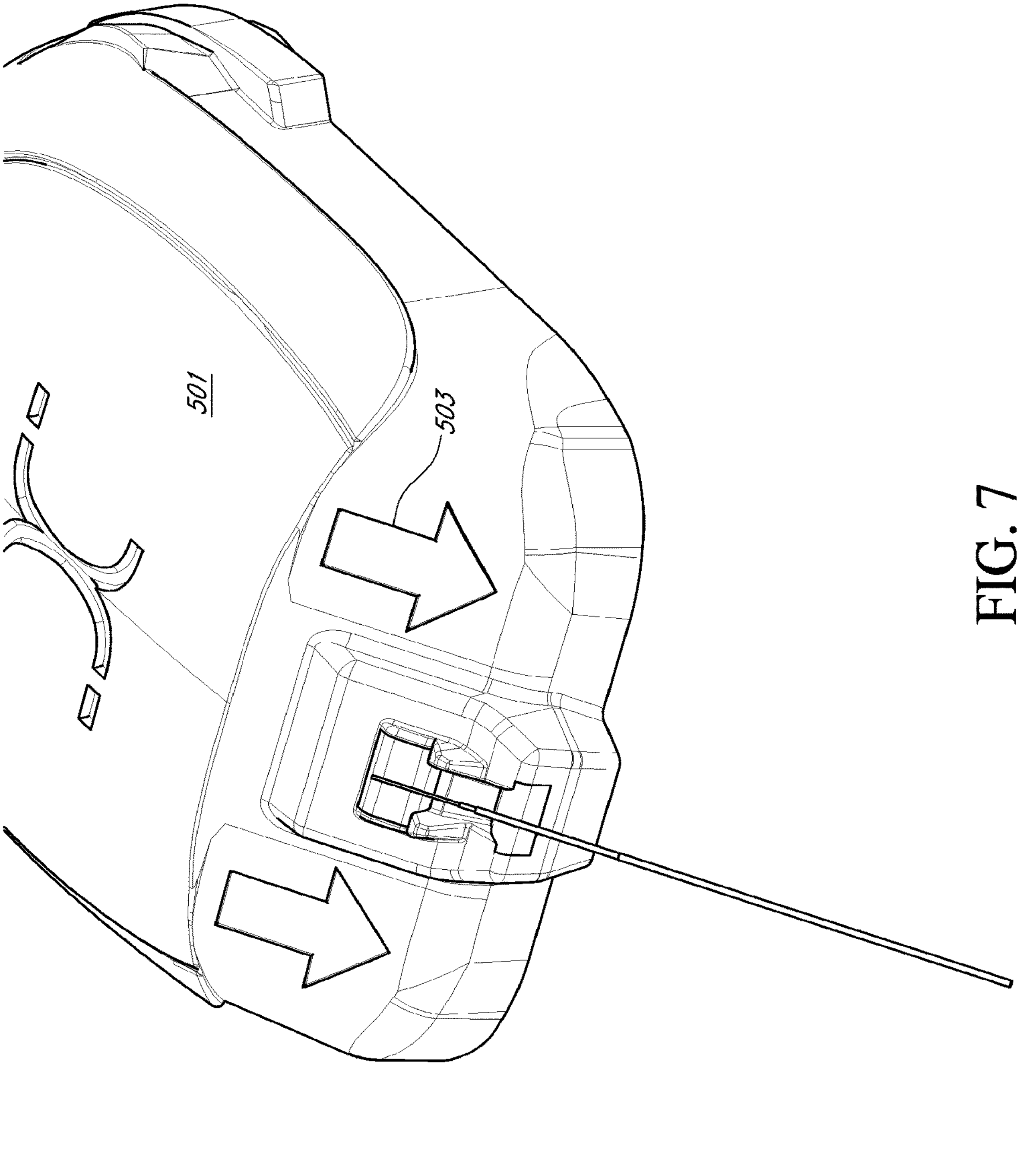
FIG. 7 is a front perspective view of components of the sensor system of FIG. 3B, including the transmitter.

FIG. 7 is a front perspective view of components of the sensor system of FIG. 3B, including the transmitter 501, which is generally combinable, partly or wholly, with other embodiments described herein. In one form, a leading end of the transmitter 501 includes arrows 503 whose orientation corresponds to the proper direction of insertion into the housing 481. The arrows 503 thus aid the user in properly orienting the transmitter 501 for coupling with the housing 481, thereby reducing the chance of an improper insertion. As shown in FIG. 5A, the housing 481 may include corresponding arrows 503' that further aid the user in properly inserting the transmitter 501 into the housing 481.

Figure 8A:
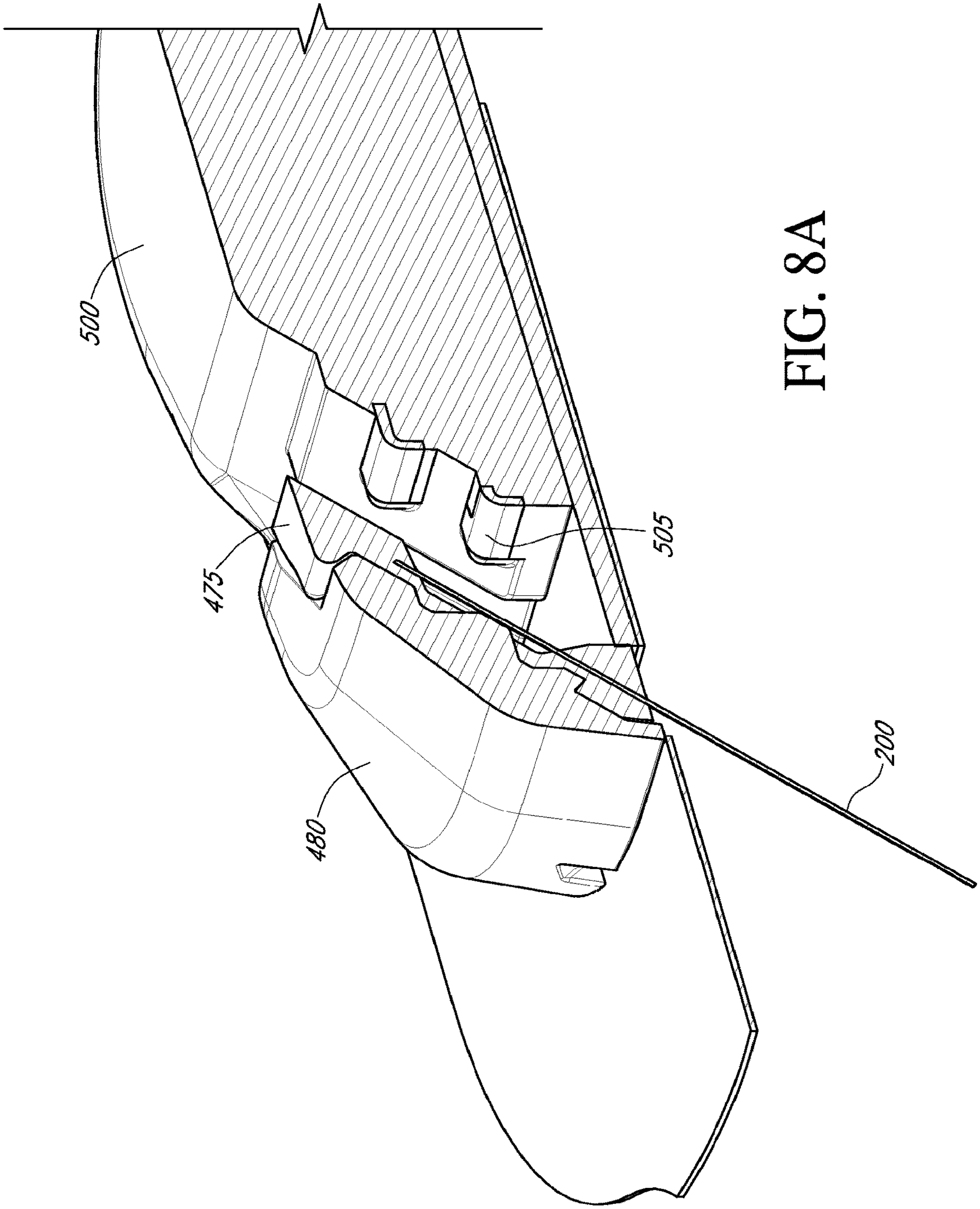
FIGS. 8A and 8B are front perspective cross-sectional views of portions of the applicator and sensor system of FIG. 3A at different stages in a method of applying the sensor system to the host, showing a mechanism for connecting the sensor to contacts on a transmitter of the sensor system during seating of the transmitter.
Figure 8B:
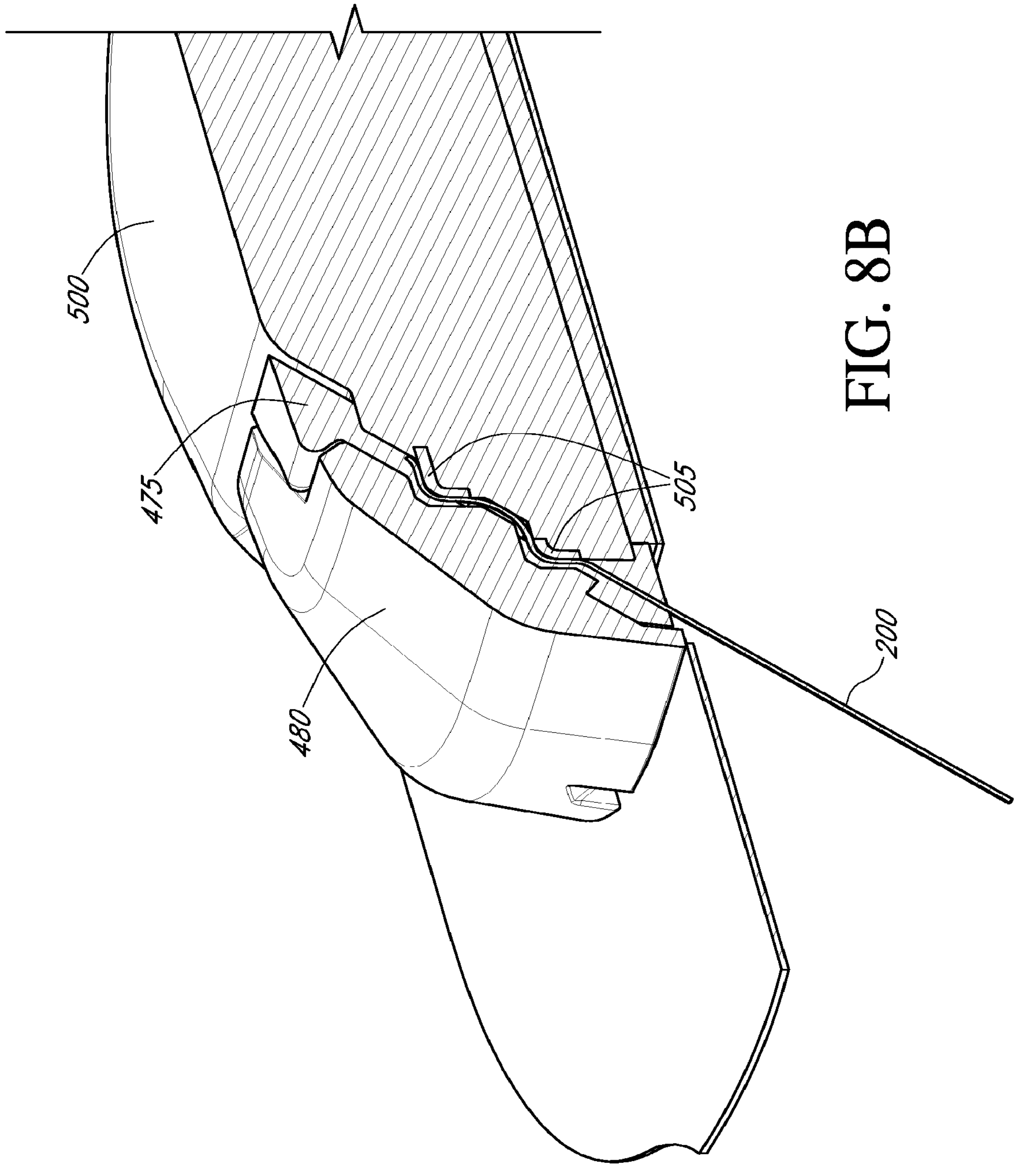

FIGS. 8A and 8B are front cross-sectional perspective views of the housing 480 and the transmitter 500 of FIG. 3A after the transmitter standoff 460 has been moved. FIGS. 8A and 8B show a mechanism for connecting the sensor to contacts 505 on the transmitter 500 as the transmitter 500 is fully seated into the housing 480. While not shown, in FIG. 8A the transmitter standoff 460 is no longer between the transmitter 500 and the elastomeric seal 475, and the transmitter 500 is free to move farther into the housing 480. Because of the force exerted on the transmitter 500 by the spring arms 468, the transmitter 500 is pushed farther into the housing 480 and is fully seated therein. The illustrated embodiment shows the sensor 200 piercing through the seal 475, however the sensor can be next to or behind the seal in some embodiments. It is noted that the internal workings of the transmitter have been omitted for simplicity.

As shown in FIG. 8B, the transmitter 500 is pressed against the elastomeric seal 475 with the sensor 200 pressed between the contacts 505 of the transmitter 500 and the elastomeric seal 475. As a result, as a consequence of the needle hub retracting, the transmitter standoff 460 is moved, and the transmitter 500 is seated into the housing 480 such that the transmitter 500 secures the sensor 200 and the contacts 505 of the transmitter 500 engage the sensor 200. In some embodiments, the time between the sensor 200 being inserted into the host and the transmitter 500 securing the sensor is less than about 1 s, about 0.5 s, or about 1 ms. Advantageously, this provides for a quick and controlled seal to be formed around the electrical connections between the sensor and electrical contacts 505 of the transmitter 500, thereby reducing opportunity for the sensor to be disturbed by external influences. Further, this seal is advantageously performed by the user, not at the factory, which allows the device to use a needle not having a longitudinal channel, which further achieves a less painful insertion with a smaller gauge needle. Further, in systems where the sensor is pre-terminated (electrical contact) and sealed as part of a housing assembly, these steps are part of the manufacturing process, which adds to the cost. The user making the electrical contacts and seal eliminates those manufacturing steps and reduces manufacturing costs. However, in some embodiments wherein the sensor electronics are integral with (and disposable with) the sensor and housing, the electrical connection between the sensor and transmitter contacts can be formed at the factory. Similarly, in some embodiments wherein the needle stays on the sensor housing during the sensor session, the electrical connection between the sensor and transmitter contacts can also be formed at the factory. Accordingly, partial-seating of the transmitter may not be required in all embodiments.

In some embodiments, the contacts 505 are more rigid than the sensor 200, and the contacts 505 press the sensor 200 into the elastomeric seal 475. Also in some embodiments, the elastomeric seal 475 is compressed and conforms to the sensor 200 to form a high friction contact with the sensor 200 and to form a seal around the sensor 200.

In some embodiments, a high tack gel, a pressure sensitive adhesive (PSA), or a two part adhesive may be used. For example, some embodiments use an epoxy having two compounds that mix as part of the applicator 400 actuation and subsequently cure. In some embodiments, the PSA, the epoxy compounds, or other adhesive material may be enclosed in a flexible container. When the transmitter 500 is seated into the housing 480 the container may be compressed so as to release the material. The released material then secures and seals the sensor 200. Holes in the container through which the material escapes may be either formed during manufacturing or as a result of the compression, or both.

In some embodiments, additional or alternative mechanisms may be used to secure the sensor 200 in place and to form a seal around the sensor 200. For example, mechanical structures, such as a clamp attached to either the housing 480 or the transmitter 500 and grasping a portion of the sensor 200 may be used. Alternative examples of mechanical structures include a wedge applying pressure to the sensor 200, a barb, a one-way valve, or a tension lock, for example. In the embodiment illustrated, the sensor 200 is bent by the compression force of the transmitter 500 against the housing 480. In this way, the sensor is secured or retained within the assembly with a retention force of at least about 0.1, 0.2, 0.3, 0.4, 0.5, 1 or 2 pounds when subjected to a standard pull test or push test (after insertion of the sensor through the housing). In some embodiments, such as the embodiment wherein the sensor is kinked, it will tend to bind by compression against the contacts of the transmitter, making the sensor particularly resistant to pushing (for example from the body if, for example, the sensor were to be inserted at a site of dense tissue, such as muscle). The sensor may even exhibit a resistance to pushing that is greater than its resistance to pulling. This resistance is such that the sensor remains attached to the assembly (and not in the skin of the patient), when the sensor session has ended and a user removes the system from the skin by peeling back the adhesive.

Figure 39:
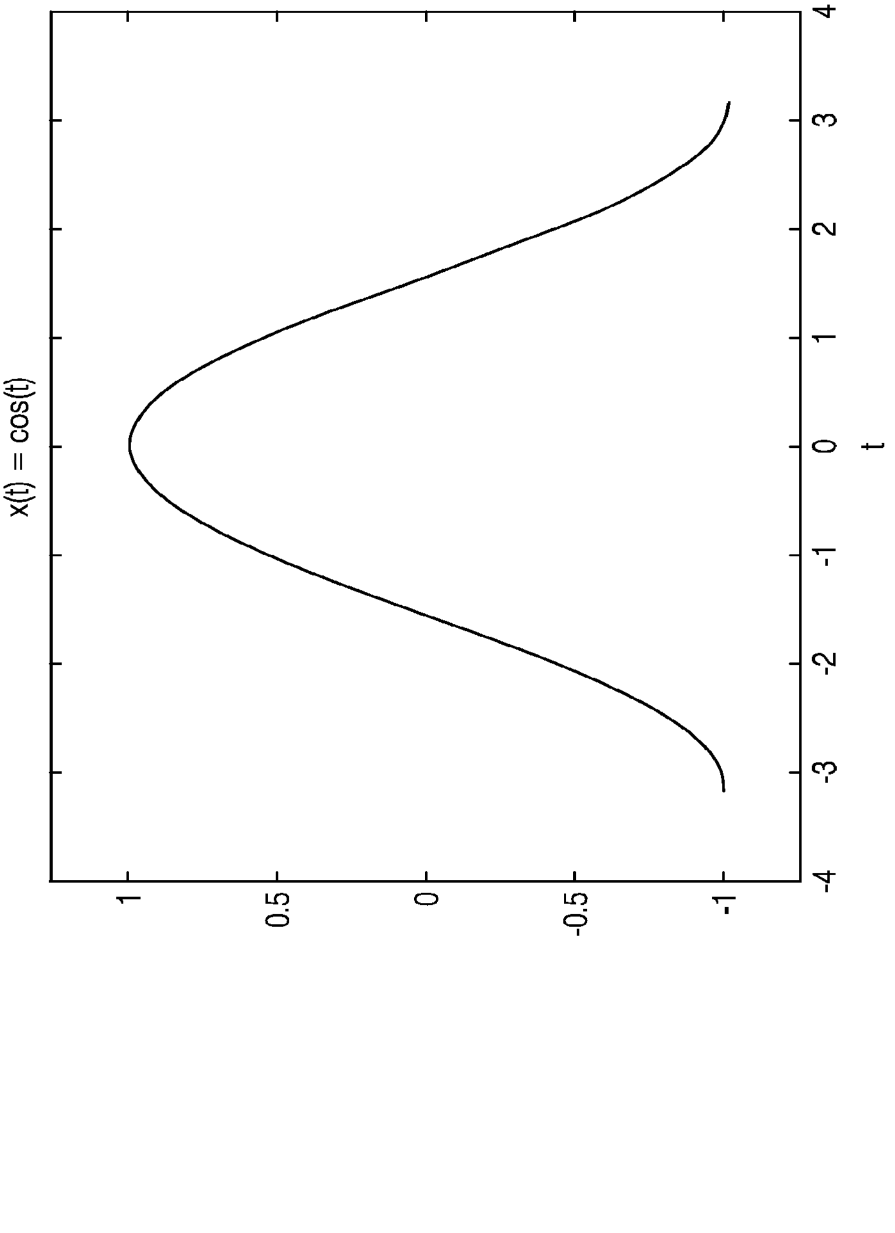
FIG. 39 is a schematic view of a rounded kink feature for sensor retention, according to a generally applicable embodiment.
Figure 40:
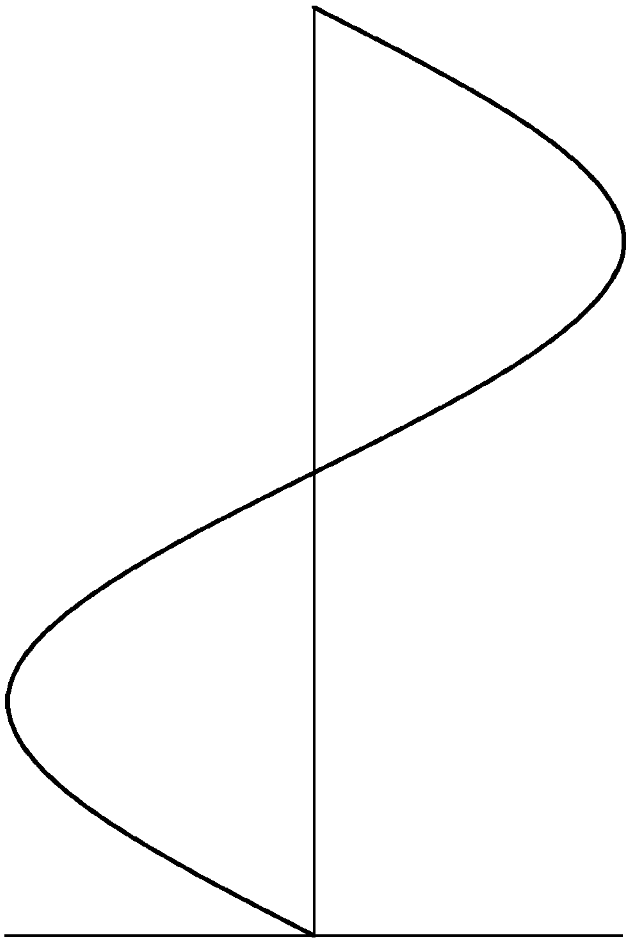
FIG. 40 is a schematic view of a S-bend kink feature for sensor retention, according to a generally applicable embodiment.
Figure 41:
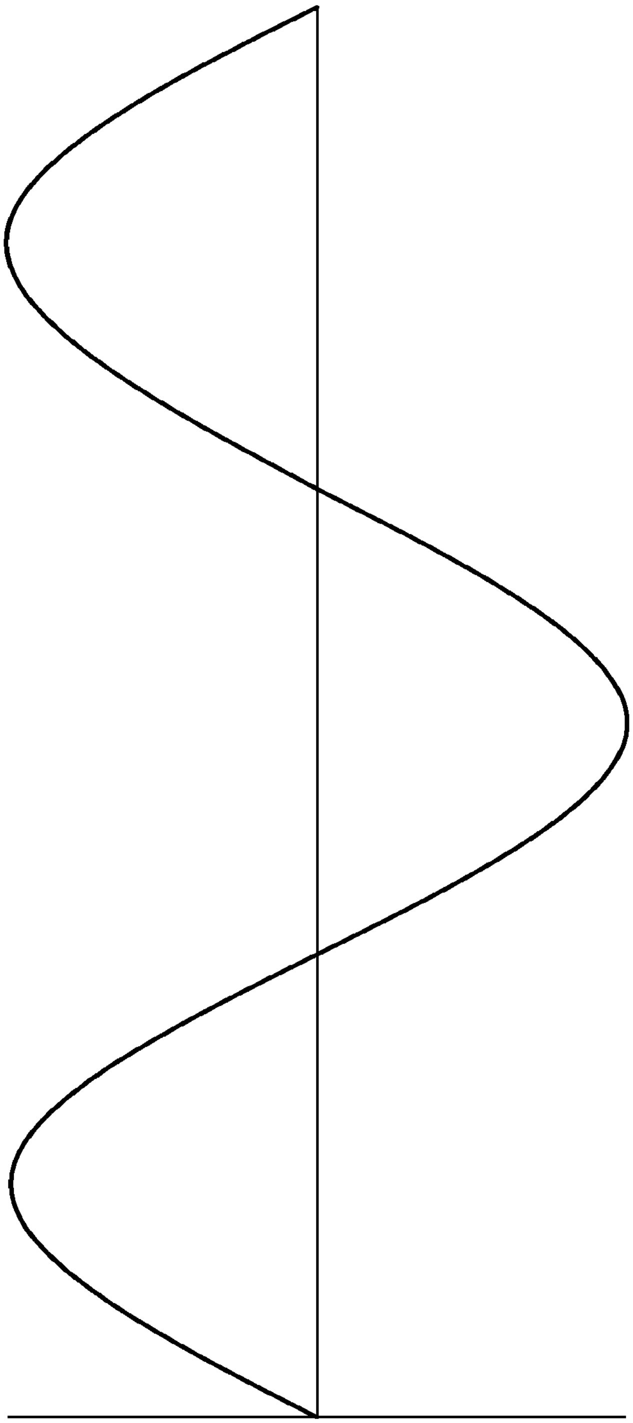
FIG. 41 is a schematic view of a triple-bump kink feature for sensor retention, according to a generally applicable embodiment.

FIGS. 39-41 illustrate various geometries for how the upper end of the sensor may be bent in order to create a retention force to hold it inside the lumen of the deployment needle, as discussed above, which geometries are combinable, partly or wholly, with other embodiments described herein. Example bend geometries include a cosine function (FIG. 39), a sine function with two inflections (FIG. 40), or a sine function with three inflections (FIG. 41). Other geometries are possible, and the foregoing three are just examples. With the present embodiments, the sensor wire can be front-loaded (or back-loaded) without fear of scraping the wire against the bevel of the needle. The bend geometry also provides sensor retention within the needle and a larger surface area for the pushrod to contact. Further, the rounded bend geometries allow the sensor wire to be in-line with the exception of the bent portion such that the wire is essentially straight throughout and centered throughout the needle lumen. Another advantage is that the rounded bend is a form of sensor retention through a pierced seal as it increases the pull resistance of the sensor, or the force necessary to pull the sensor out from the pierced seal.

In some embodiments, once the sensor 200 is inserted into the host, the sensor 200 is surrounded by an elastomeric seal to secure the sensor 200 in place. For example, as part of the sensor insertion, the needle 435 may insert the sensor 200 into the host through the elastomeric seal 475 or through another elastomeric seal, such as a septum seal (not shown). Subsequently, when the transmitter 500 is seated in the housing 480, the transmitter 500 compresses the elastomeric seal to secure the sensor 200 and to form a seal around the sensor 200.

In some embodiments, the sensor 200 is held in place by multiple elastomeric seals. For example, five seals may be used, wherein in a first set comprising the first, third and fifth seals is aligned, and a second set comprising the second and fourth seals is aligned, but the first and second sets are offset from each other. When the transmitter 500 compresses the seals, the misalignment of the sets causes different forces to be applied to the sensor 200 by the seals of each set. Accordingly, the sensor 200 does not maintain a linear state, despite having been threaded through the seals with a linearly moving needle. The nonlinear configuration increases the securing and sealing force of the seals.

In some embodiments, the offset sets of seals may be compressed when the sensor 200 is threaded therethrough, and subsequently uncompressed. When uncompressed, the offset configuration of the sets causes different forces to be applied to the sensor 200 by the seals of each set. In some embodiments, the sensor 200 is inserted all the way through one of the seals, such that once the needle retracts, the end of the sensor is closer to the host than the one seal. The one seal is compressed either during insertion of the sensor 200, or after, or both, so that after the retraction of the needle, the slit formed in the one seal by the needle travelling therethrough moves away from the end of the sensor 200 such that if the sensor were to be forced back to the one seal, the sensor would push against the one seal instead of moving back through the slit. Similarly other seals may be compressed during and/or after sensor 200 insertion in such a way that the sensor 200 is not aligned with the slit in the one seal.

In some embodiments, once the sensor 200 has been inserted into the host, the sensor 200 has a ferrule around it to form a seal. For example, the sensor 200 may extend through an elastomeric tapered ferrule that is set in a rigid sleeve conforming to the same taper as the ferrule. Either during the insertion process, or as a result of the transmitter 500 being seated, or both, the ferrule receives pressure, which causes it to compress against the sleeve and against the sensor 200 to secure the sensor 200 and to form a seal around the sensor 200.

FIGS. 9A-9E are front cross-sectional perspective views of the sensor insertion mechanism at various stages in a method of actuating the applicator 401 with the trigger 406, which embodiment is combinable, partly or wholly, with other embodiments described herein. FIGS. 9A-9D show an embodiment of pushrod actuation, and substantially correspond to the actuation timing of FIGS. 6A-6D, respectively. In some embodiments, wherein the sensor is not attached to the sensor insertion mechanism, and because the sensor is "handed off" from the applicator to the on-skin sensor assembly, the independent movement of the sensor relative to other portions of the applicator and on-skin assembly is controlled at least partially by the pushrod 426. In general, the pushrod is positioned within the needle 436 prior to sensor insertion, and is configured to move with the needle as the needle is inserted into the host, and to remain fixed as the needle is removed from the host, whereby the pushrod is configured to prevent the sensor from being retracted from the host with the needle. In this example embodiment, the pushrod 426 initially (FIG. 9A, 9A') is latched onto the needle hub 431 to cause the pushrod to move with the needle during insertion of the needle into the host. When the needle is in its farthest extended position (FIG. 9B, 9B'), the pushrod becomes unlatched from the needle hub and engages the back cover of the applicator, thereby immobilizing the pushrod as the needle hub retracts into the applicator, as described further below.

FIGS. 9A and 9A' show the configuration of the pushrod 426 and the needle hub 431 when the transmitter 501 is partially seated within the housing 481 and prior to the trigger 406 being activated. It is noted that the internal workings of the transmitter have been omitted for simplicity. The wheel 421 has not rotated, and the needle 436 and needle hub 431 are within the applicator 401. As shown in FIG. 9A', the end 426'of the pushrod 426 opposite the needle is coupled to the needle hub 431. The opposite end of the pushrod extends into the back end of the needle 436 and is adjacent to the sensor 200, which is inside the needle 436.

Figure 9B:
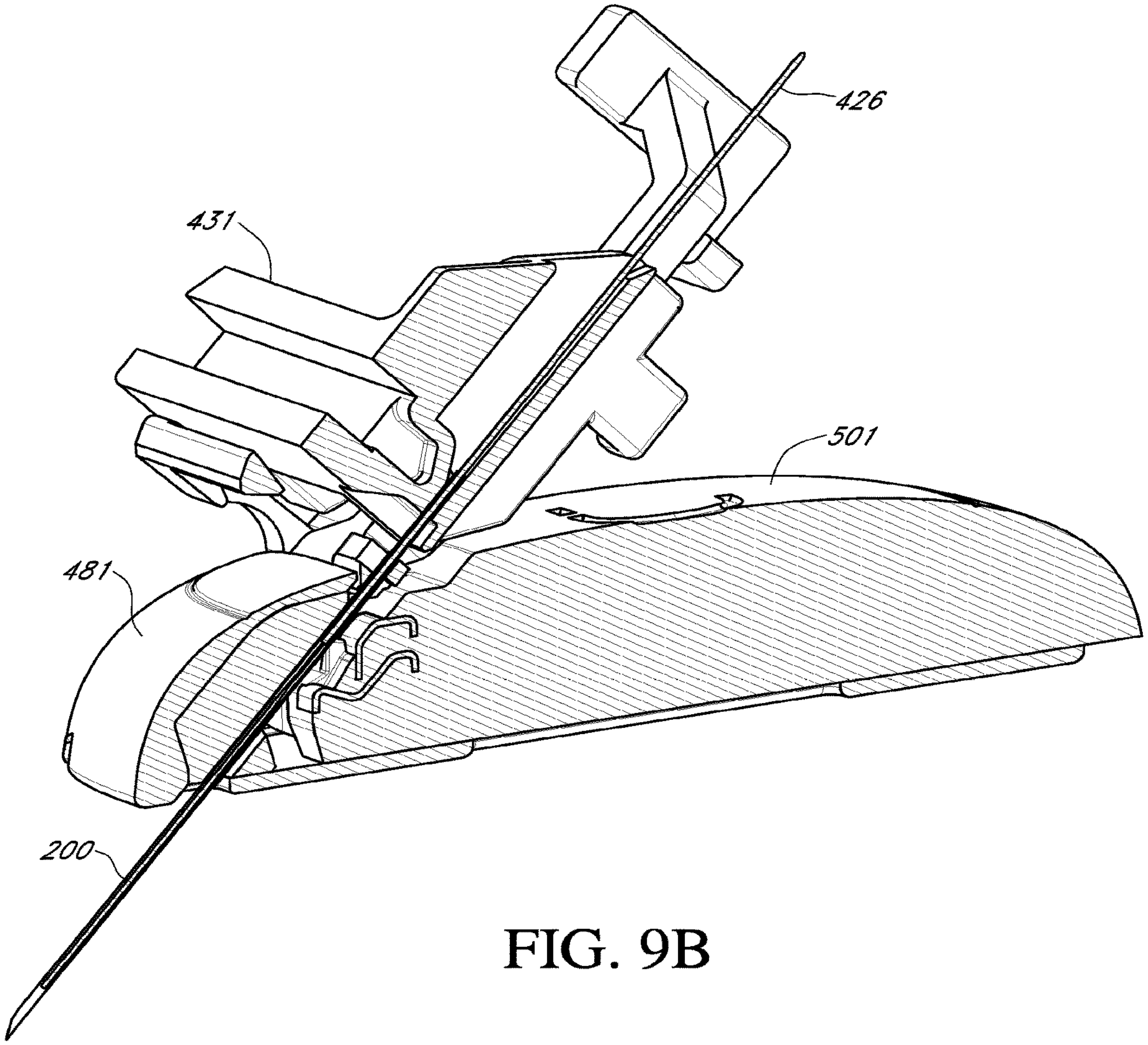
Figure 9B:
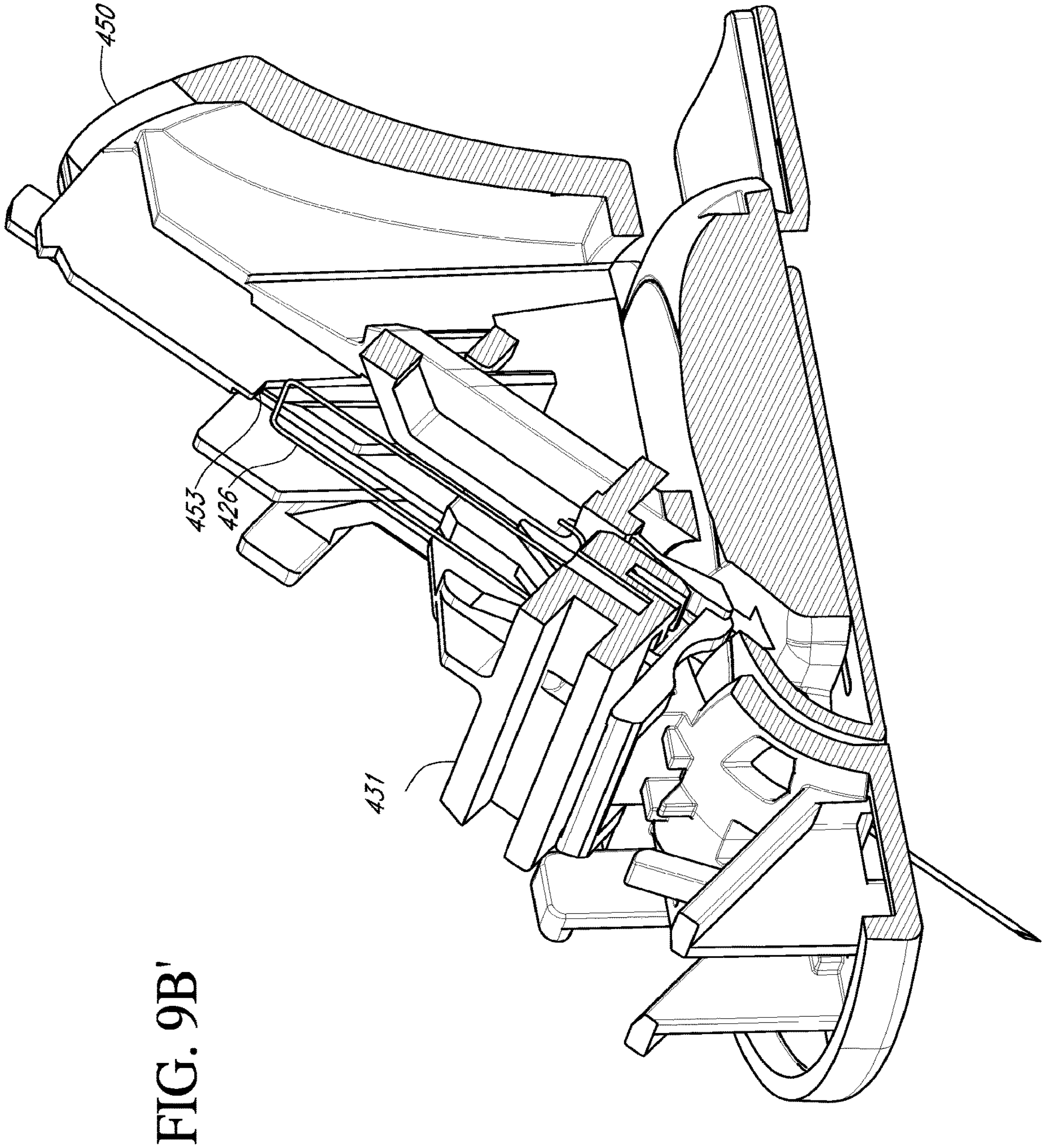

FIGS. 9B and 9B' show the pushrod 426 and the needle hub 431 after the wheel has rotated about 90 degrees in response to the trigger 406 being activated. As shown, the pushrod 426 has traveled with the needle hub 431 during the extension of the needle 435. Accordingly, the opposite end of the pushrod still extends into the needle 435. The top end of the pushrod 426 engages a notch 453 in the back cover 450 as the needle hub 431 moves upward. The notch 453 prevents the pushrod 426 from further movement. The pushrod 426 thus disengages the needle hub 431, pushing the sensor 200 out of the needle 436 as the needle hub 431 retracts.

Figure 9C:
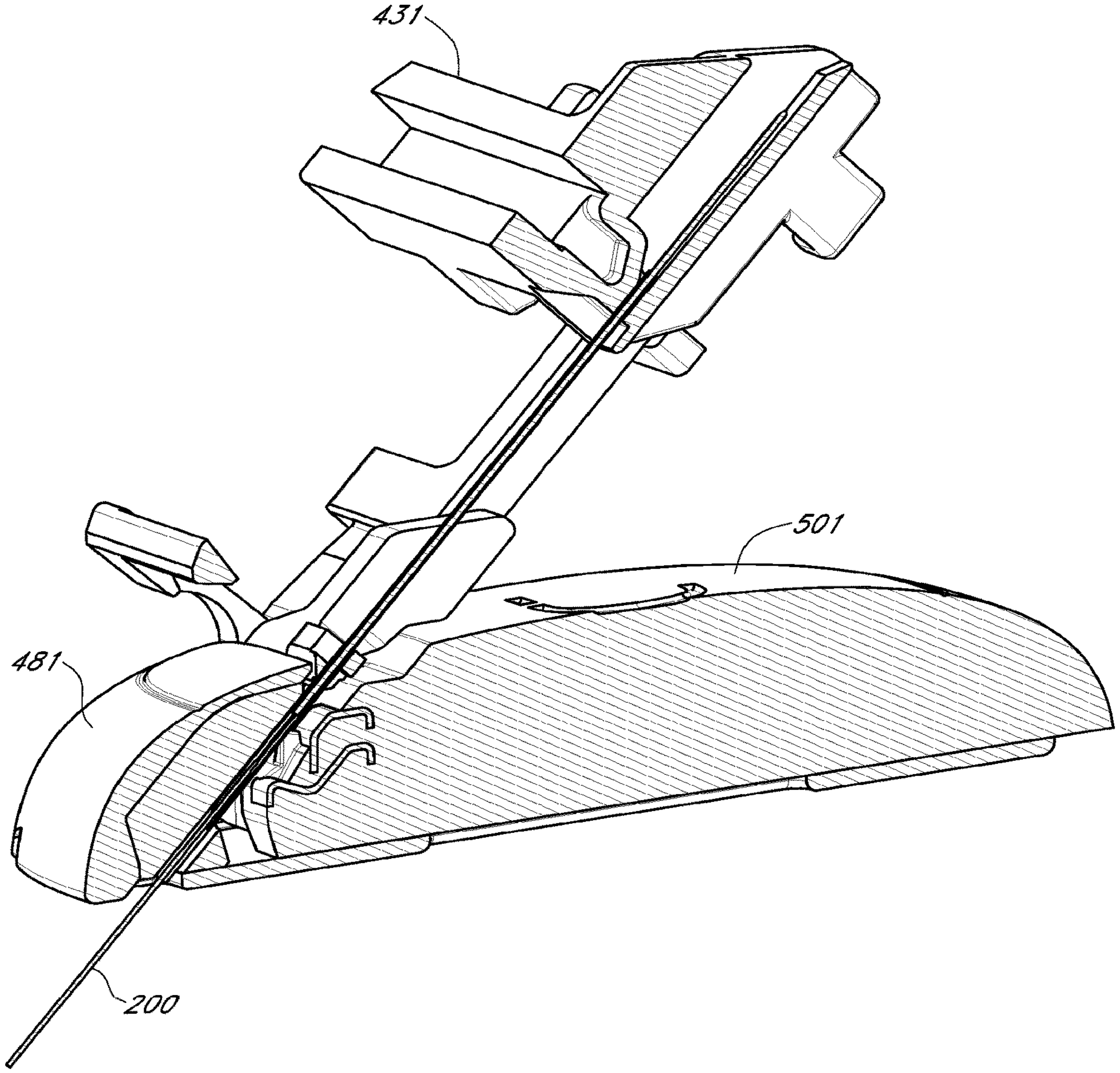

FIG. 9C shows the pushrod 426 and the needle hub 431 with the wheel 421 having rotated about 180 degrees after the trigger 406 has been activated. As shown, the needle hub 431 has moved so as to retract the needle 435 from the host. The top end of the pushrod has not moved and continues to be engaged with the notch 453 in the back cover 450. The opposite end of the pushrod has remained in the needle 435 as the needle 435 has been removed from the host. Therefore, the pushrod has pushed against the sensor 200 within the needle 435 to prevent the sensor 200 from exiting the host with the needle 435. In some embodiments, the pushrod 426 may be further retracted by a mechanism that removes the pushrod 426 from the notch 453 and reconnects the pushrod 426 to a holder (not shown) on the needle hub 431 prior to the full retraction of the needle.

Figure 9D:
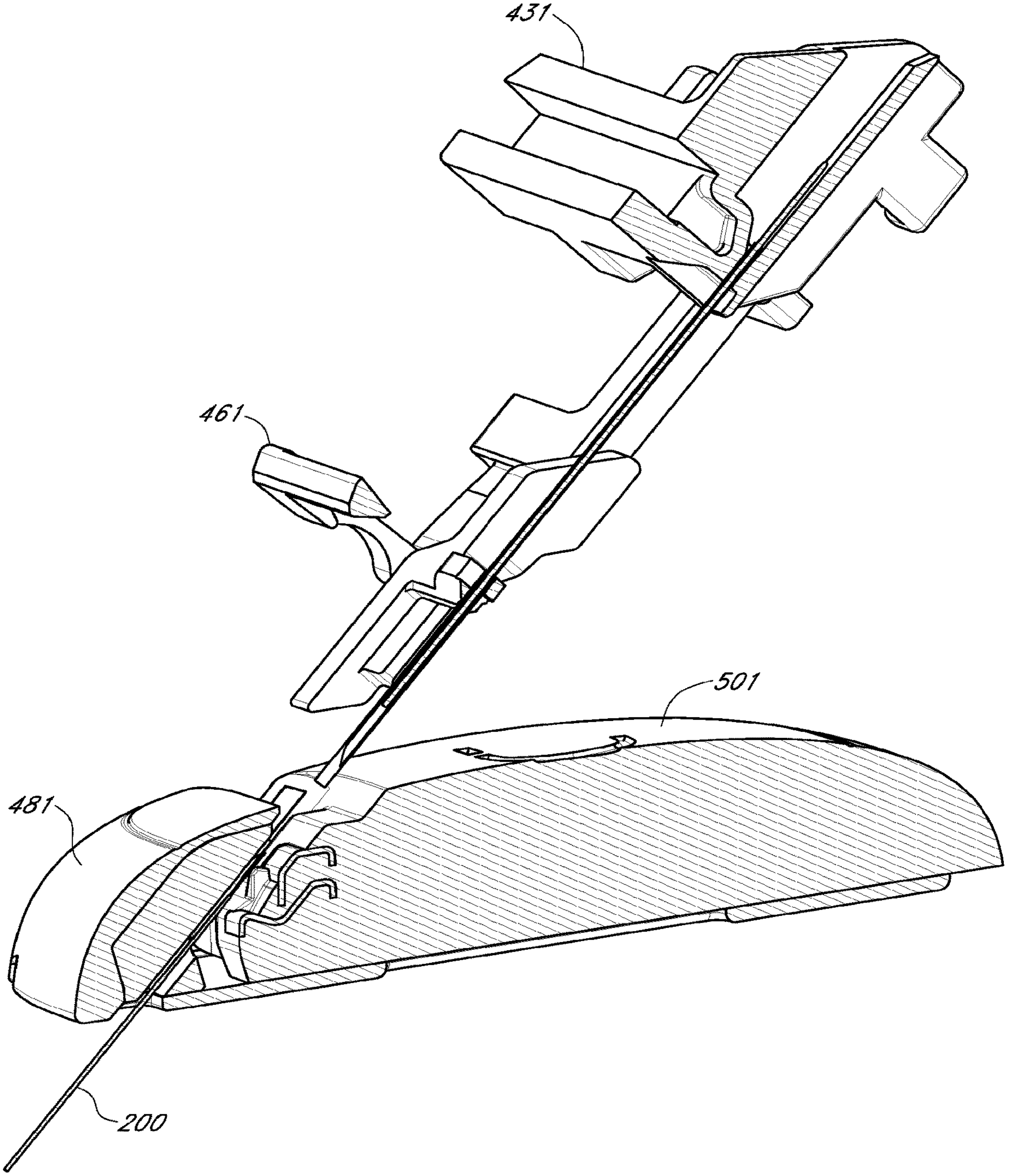
Figure 9E:
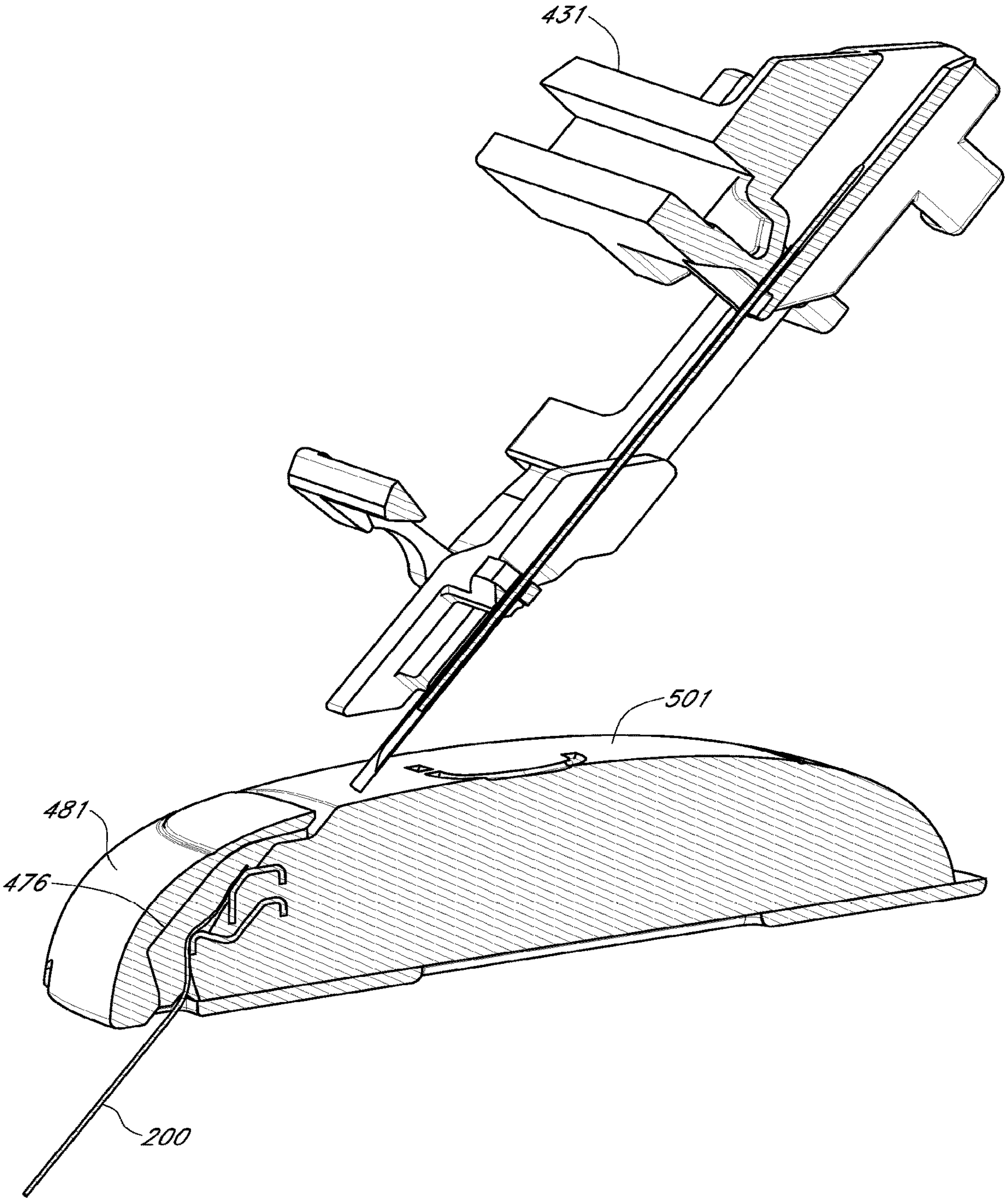

FIGS. 9D and 9E show the needle hub 431 after the wheel has rotated about 270 degrees in response to the trigger 406 being activated, as discussed above. The sensor 200 has been inserted into the host and the needle hub 431 has been moved by the wheel projection 422. The needle hub 431 has engaged the transmitter standoff 461 and lifted the transmitter standoff 461 out of the path of the transmitter 501. As a result, the transmitter standoff 461 no longer prevents the transmitter 501 from moving in response to the spring arms 468. With the transmitter standoff 461 lifted, the applicator spring arms 468 fully seat the transmitter 501 and compress the seal 476.

Figure 9F:
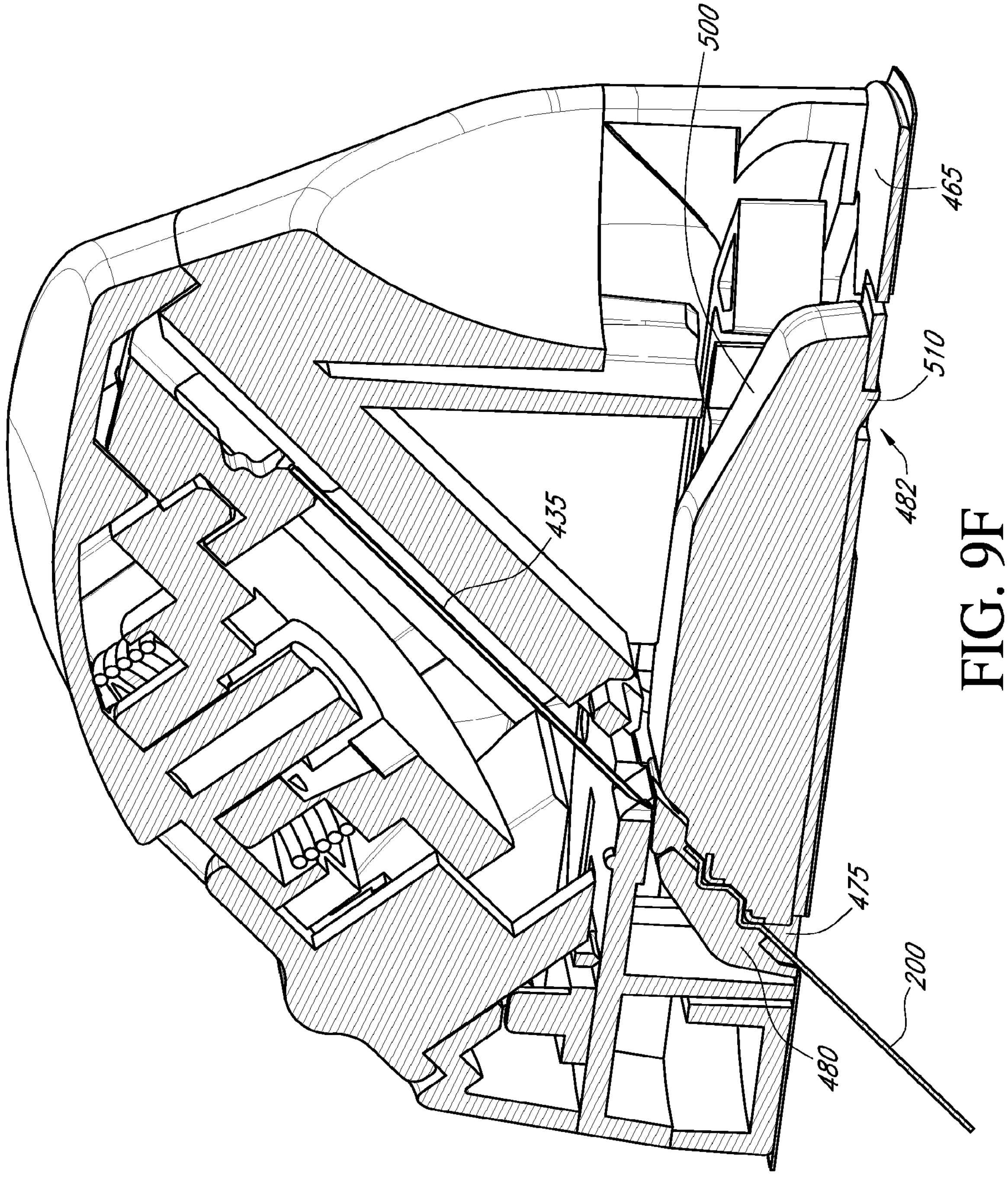
FIG. 9F is a rear perspective cross-sectional view of the applicator of FIG. 3A with the transmitter seated.

FIG. 9F shows that the transmitter 500 has traveled sufficiently that the trailing edge of the transmitter 500 no longer contacts the applicator base 465. Because the trailing edge of the transmitter 500 no longer contacts the applicator base 465 no longer contacts the housing 480. Accordingly, the housing 480 and the transmitter 500 are no longer connected to the remaining portions of the applicator 400, and the applicator 400 is detached from the housing 480. The transmitter 500 is secured to the housing 480 because of a protrusion 510 in the transmitter 500 extending into hole 482 in the housing 480. Other mechanisms may also be used to secure the transmitter 500 to the housing 480. In this way, the embodiment described herein allows for automatic sensor insertion, (including needle insertion and removal), transmitter seating (including electrical connection and seal compression), and release of the applicator from the housing, all without any user interaction other than actuating the trigger.

With further reference to FIG. 9E, engagement of the transmitter 501 with the elastomeric seal 476 deforms the elastomeric seal 476 to an extent that the upper end of the sensor 200 is kinked in at least one place. The kinking increases the force that would be necessary to pull the sensor 200 out from the space between the transmitter 501 and the elastomeric seal 476. The sensor 200 is thus less likely to be pulled out of that space when the user removes the sensor 200 from his or her skin, which would be undesirable because the sensor 200 may then be left stuck in the skin.

Material properties of the elastomeric seal preferably provide both good sealing and maintenance of contact between the sensor and the contacts on the transmitter. Materials having a low durometer may provide good sealing, but if the durometer is too low the sensor may tend to pull away from the contacts because of relaxation in the sealing material. One material that has been found to produce desired results is thermoplastic elastomer (TPE), particularly VERSAFLEX™ CL2003X TPE, available from Polyone Corporation. However, other materials may be used.

In a generally applicable embodiment, portions of the seal configured to contact at the sensor contact points are reinforced and/or conductive particles are provided in the sealing material, which embodiment is combinable, partly or wholly, with other embodiments described herein. In one form, pucks formed from a sealing material (e.g., with a higher durometer than other portions of the seal) are formed or inserted into the seal, and include conductive particles. In practice the conductive pucks align with the sensor (contact points) after sensor insertion, pressing the sensor against the contacts of the transmitter and ensuring good electrical connection without sacrificing sealing properties.

With reference to FIGS. 8A and 9A, there are numerous potential configurations for the elastomeric seal 475, 476 with respect to the sensor 200. For example, with reference to FIG. 8A, the sensor 200 may pierce the elastomeric seal 475 in one or more places, and be held in the elastomeric seal 475 by friction. While FIG. 8A illustrates the sensor 200 piercing the elastomeric seal 475 in two locations, any number of locations could be provided.

With reference to FIG. 9A, the elastomeric seal 476 may include a bore 900 that receives the cannula 463, and the sensor 200 may extend partially into the bore 900 or be spaced from the bore 900 as in FIG. 9A. When the applicator 401 is activated by pushing the button 406, the sensor will pass through the bore 900 and into the patient's skin, while engagement of the transmitter 501 with the elastomeric seal 476 deforms the bore 900 to hold the sensor 200 in the bore 900 with a squeezing force. In this embodiment, the mating of the sensor 200 with the elastomeric seal 476 is performed by the user rather than the manufacturer. This aspect provides at least one advantage. The sensor 200 can be loaded into the needle by passing it through the sharp distal tip of the needle at the time the applicator 401 is assembled. This feature enables the entirety of the applicator 401, minus the sensor 200, to be manufactured and assembled in one or more locations and then sent to another location where the sensor 200 is added. The benefit of this feature is that security for the sensors, which are often manufactured of precious metals such as platinum, can be tightly controlled to reduce the risk of theft.

With further reference to FIG. 9A, at least in part because the sensor 200 is not embedded in the elastomeric seal 476 at the time of manufacture and assembly, it is not actually attached to any portion of the applicator 401. Rather, it is held inside the needle 436 by friction. However, the diameter of the sensor 200 is less than the inside diameter of the needle 436. Thus, to produce the friction necessary to prevent the sensor 200 from falling out, a top end of the sensor 200 may include a bend or kink (not shown) to create a spring force in the sensor 200 when it is inserted into the needle 436, thereby causing various portions of the sensor 200 to bear with force against the inside of the needle 436.

Figure 10:
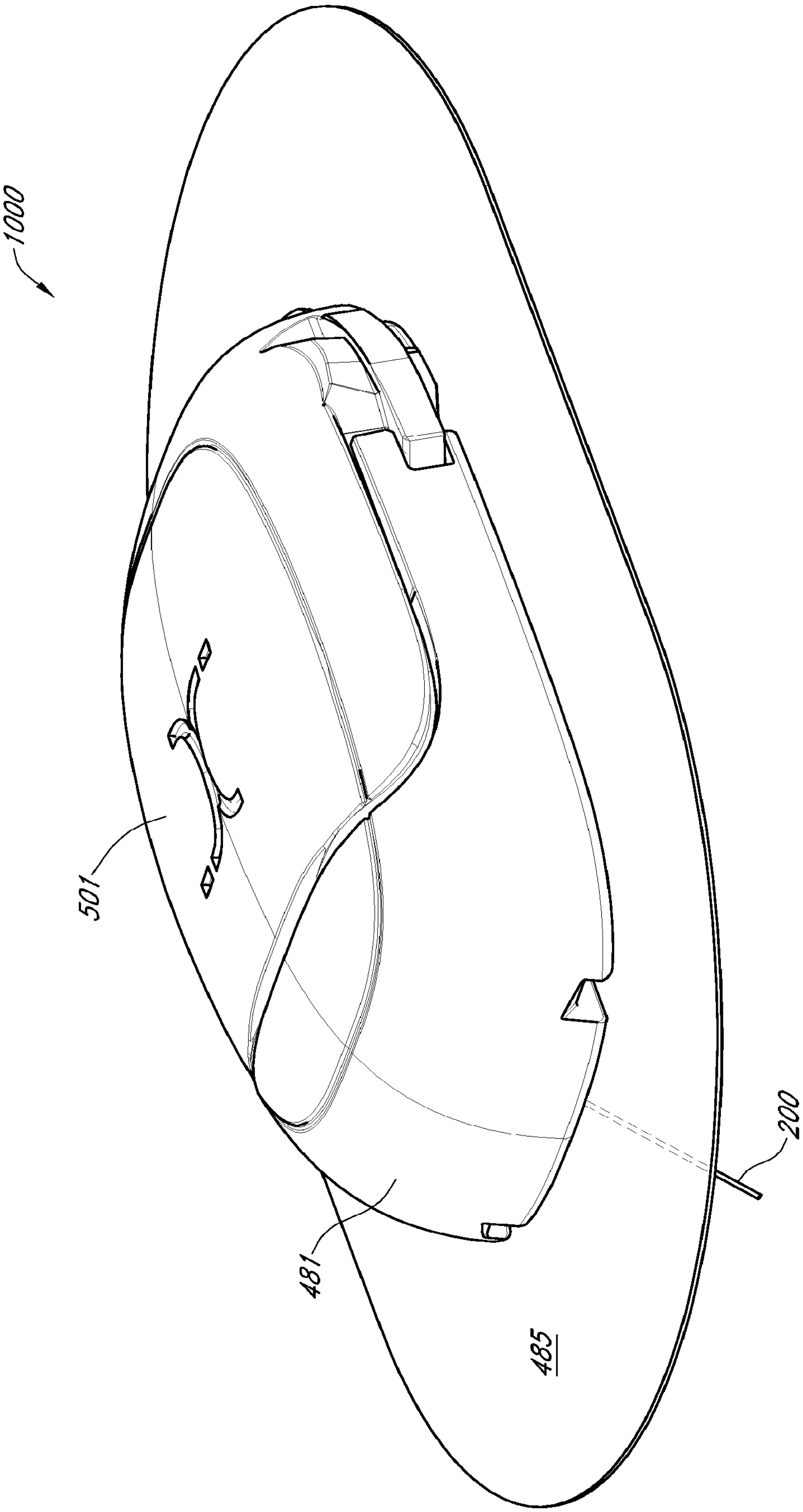
FIG. 10 is a front perspective view of the sensor system of FIG. 5A after application to the host.

FIG. 10 is a front perspective view of the on-skin sensor assembly 1000 after the applicator 401 has detached from the housing 481, which embodiment is combinable, partly or wholly, with other embodiments described herein. In one form, the assembly 1000 comprises at least the sensor 200 implanted in the skin, the housing 481, the adhesive 485, and the transmitter 501. In some embodiments, the adhesive patch 485 is removably attached to the applicator base 465. In such embodiments, activating the trigger 406 may additionally cause an adhesive release mechanism to actuate. The adhesive release mechanism may, for example, include one or more projections that, when actuated, extend from the applicator base 465 to the adhesive patch 485 in order to remove the adhesive patch 485 from the applicator base 465. The projections may, for example, be located along a peripheral portion of the applicator base 465. In some embodiments, the projections are located adjacent to the transmitter 501.

Figure 11A:
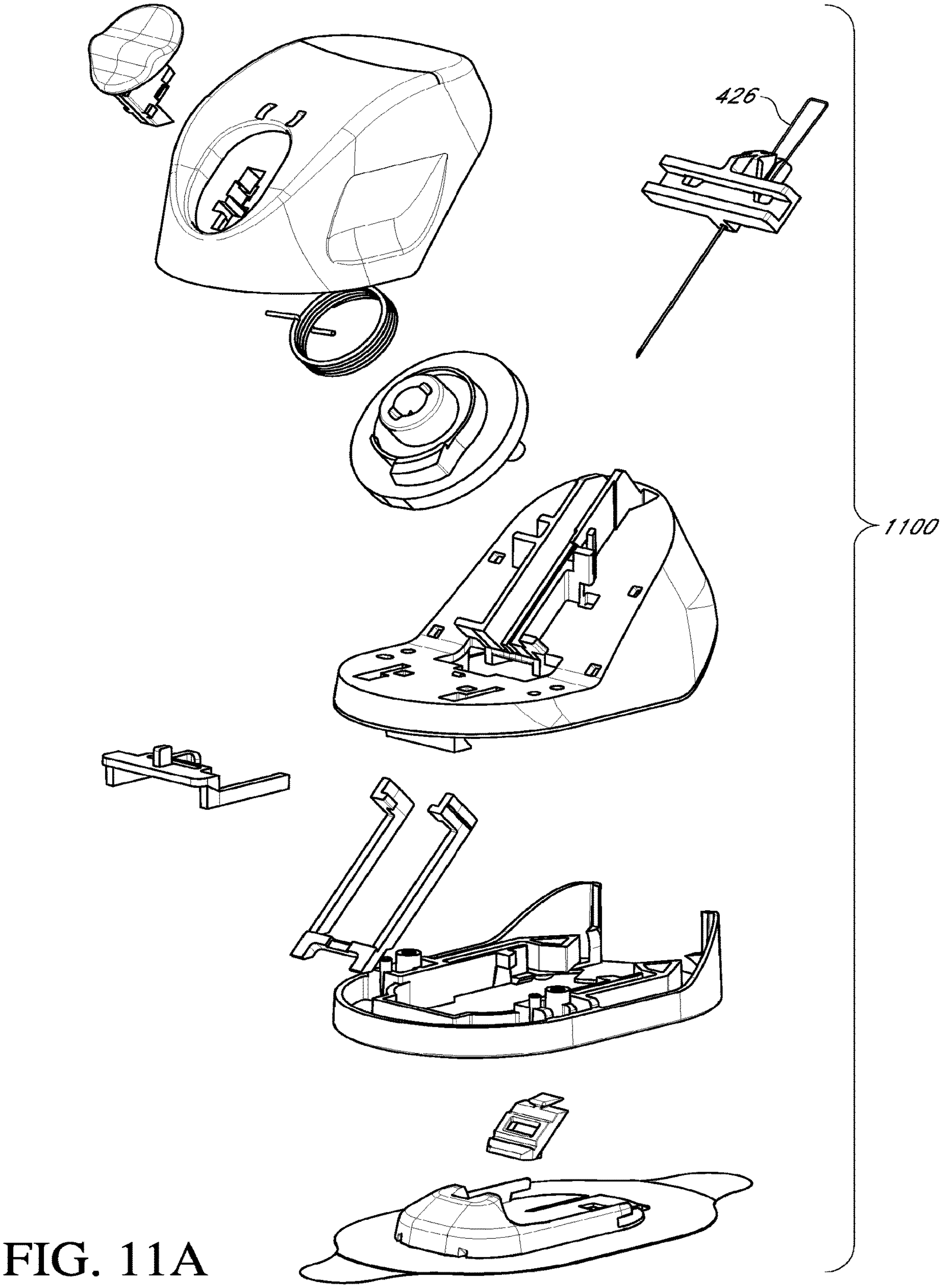
FIGS. 11A and 11B are exploded views of generally applicable embodiments of an applicator.
Figure 11B:
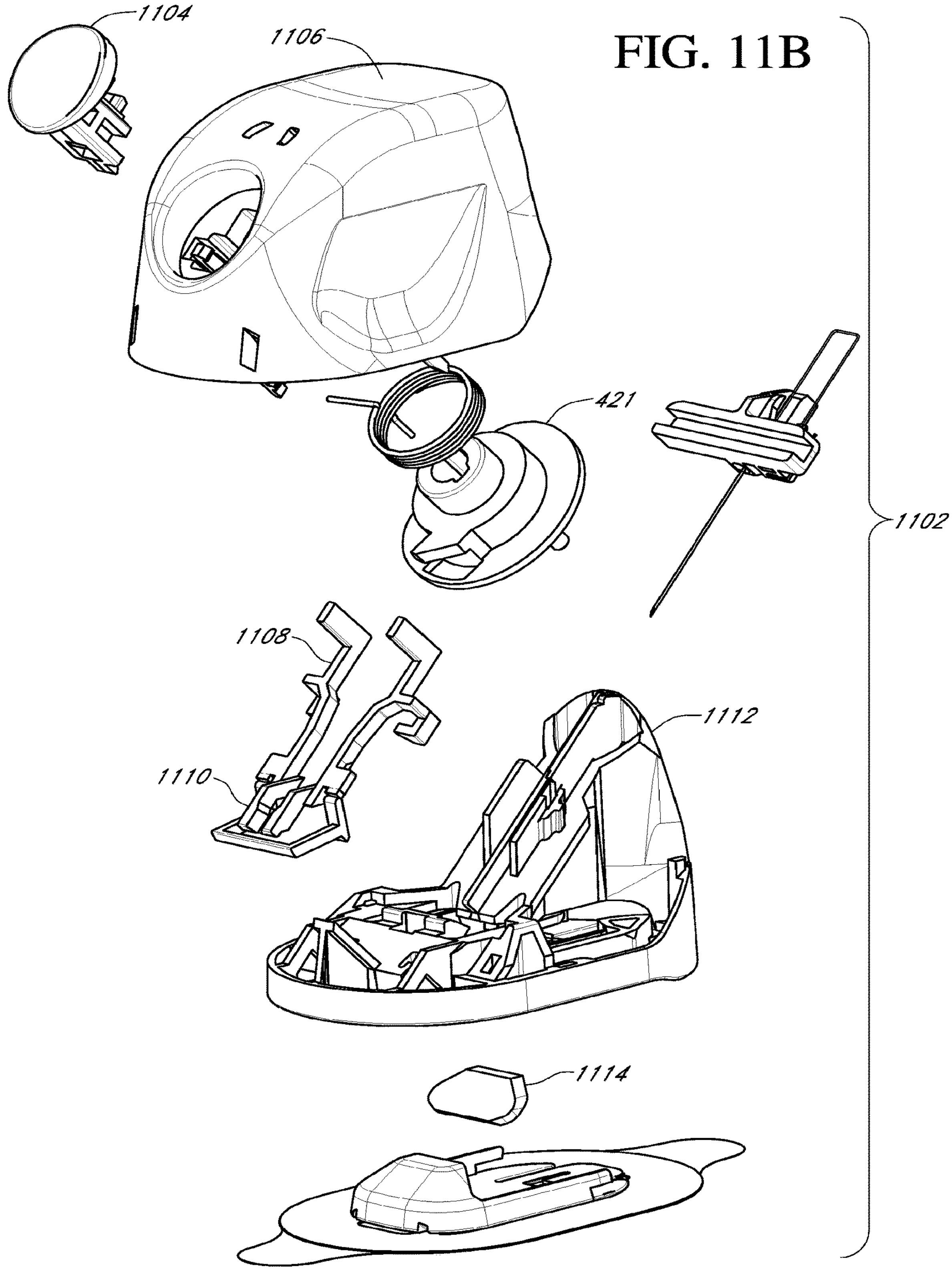

FIGS. 11A and 11B are exploded views of generally applicable embodiments of applicators used in the process shown in FIGS. 2A-2D, which embodiments are combinable, partly or wholly, with other embodiments described herein. In one form, with reference to FIG. 11A, the applicator 1100 is substantially the same to that of FIG. 3A, except that the pushrod 426 of FIG. 3B has been substituted for that of FIG. 3A. With reference to FIG. 11B, the applicator 1102 is substantially the same to that of FIG. 11A, except that the button 1104 is a pushbutton style, like that of FIG. 3B, rather than a sliding button, the front cover 1106 is shaped somewhat differently, the wheel 421 of FIG. 3B has been substituted, the needle hub 1108 and the trigger lock 1110 have been combined into a single piece, like that of FIG. 3B, the back cover 1112 is configured somewhat differently, and the shape of the elastomeric seal 1114 has been changed. One aspect of the elastomeric seal 1114 that differs from that of previous embodiments is that the relatively low durometer of the elastomeric seal 1114 seals only one side of the sensor 200, while opposite the sensor is the material of the transmitter and electrical contacts, which have a relatively high durometer.

FIGS. 12A-12D illustrate generally applicable embodiments of the housing 480, which embodiments are combinable, partly or wholly, with other embodiments described herein. Each of the embodiments of FIGS. 12A-12D have a mechanism for securing the transmitter 500 to the housing 480 by engaging protrusion 510 discussed above with reference to FIG. 10. In addition, each of the embodiments of FIGS. 12A-12D have a mechanism for securing the transmitter 500 to the housing 480 so that the transmitter 500 may not or may not easily be released from the housing 480 until the system 600 is removed from the host.

Figure 12A:
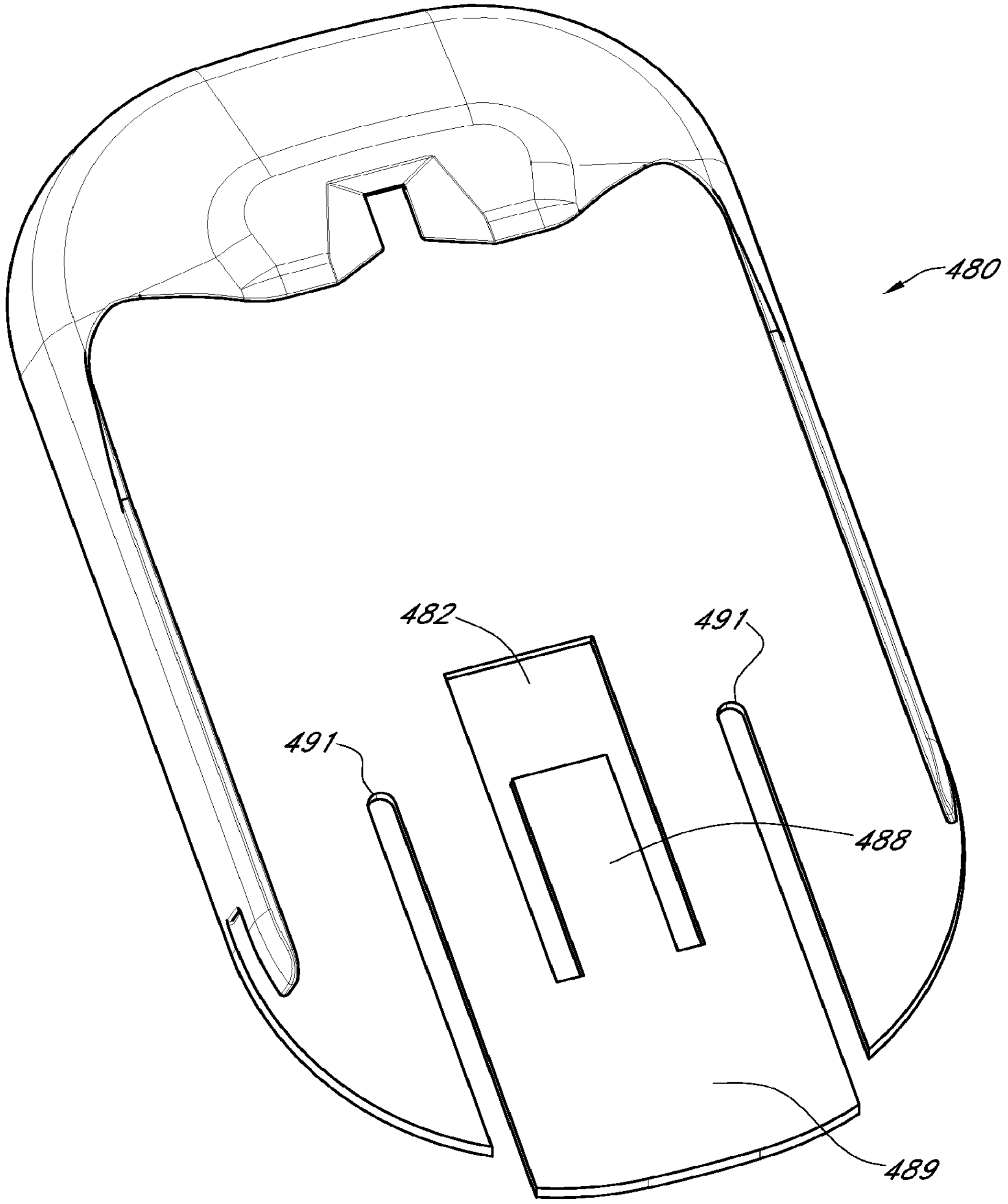
FIGS. 12A-12D are perspective/plan views of generally applicable embodiments of a housing.

FIG. 12A shows an embodiment of the housing 480 having hole 482, a first tab 488, and a second tab 489. As discussed with reference to FIG. 10, the protrusion 510 on the transmitter 500 engages the hole 482 so that the transmitter 500 is secured to the housing 480. The first tab 488 is flexible, so that when the transmitter is being fully seated into the housing 480, the first tab 488 flexes so as to provide only minimal resistance to the insertion. Once fully seated, the first tab 488 secures the transmitter 500 to the housing 480 until the second tab 489 is flexed sufficiently to disengage the first tab 488 from the protrusion 510. While being flexed, the second tab rotates about an axis which is near the end of the first tab 488 defining the hole 482. Once the rotation is sufficient, the protrusion 510 disengages from the first tab 488, releasing the transmitter 500. Because the rotation of the second tab 489 is in a direction which is into the page of the figure, away from the transmitter, the second tab 489 may not be substantially flexed while the housing 480 is attached to the user. Accordingly, the transmitter 500 may not be released from the housing 480 while the housing 480 is attached to the user. In some embodiments, sufficient rotation of the second tab 489 to cause the release also causes permanent damage to the housing 480. For example, the second tab 489 may break off.

Figure 12B:
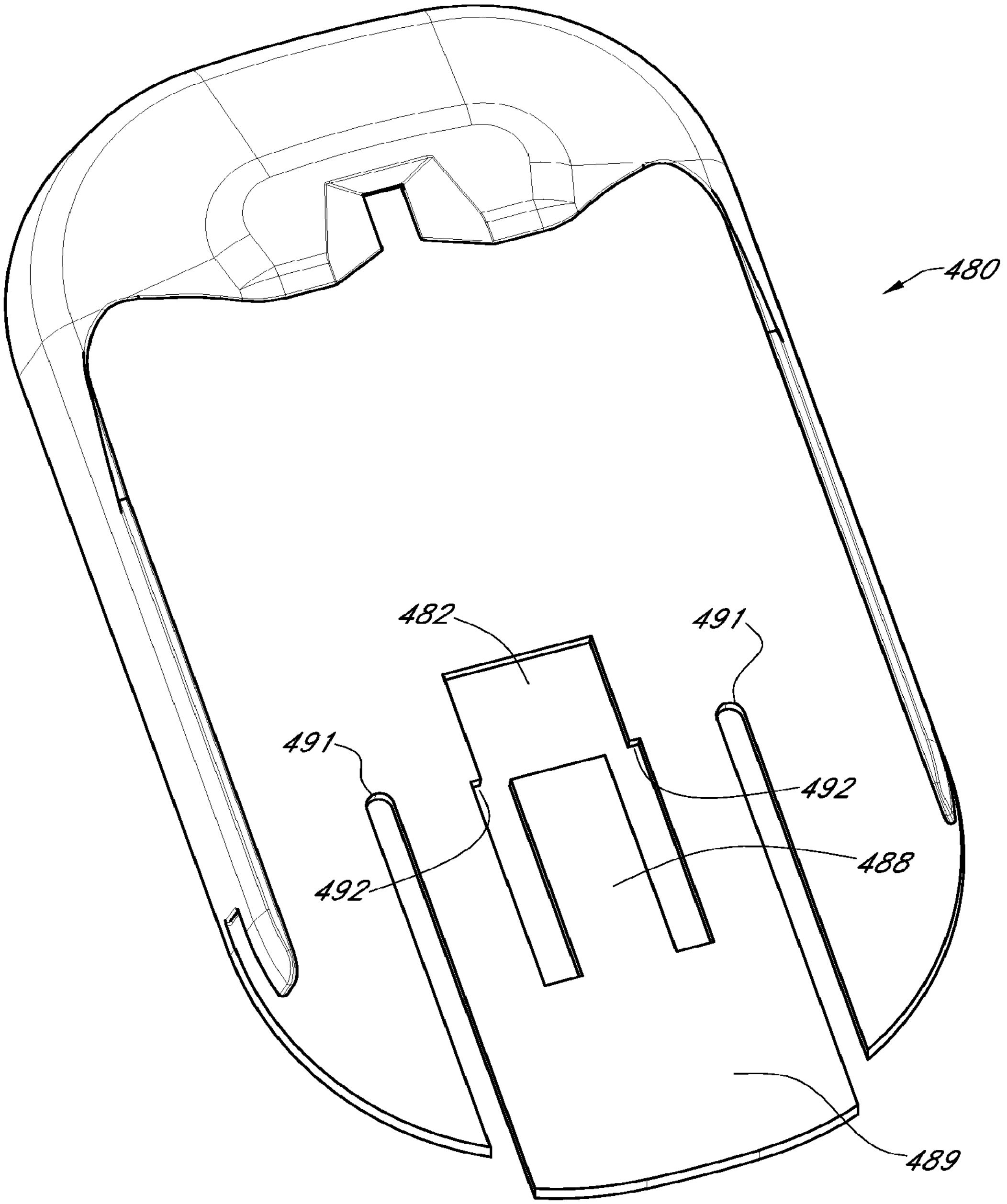

FIG. 12B shows an embodiment of the housing 480 having hole 482, a first tab 488, and a second tab 489 having features substantially the same as the corresponding structures discussed above with reference to FIG. 12A. In this embodiment, steps or notches 492 are formed in the housing 480 between the ends of slots 491 to help define the axis of rotation of the second tab 489.

Figure 12C:
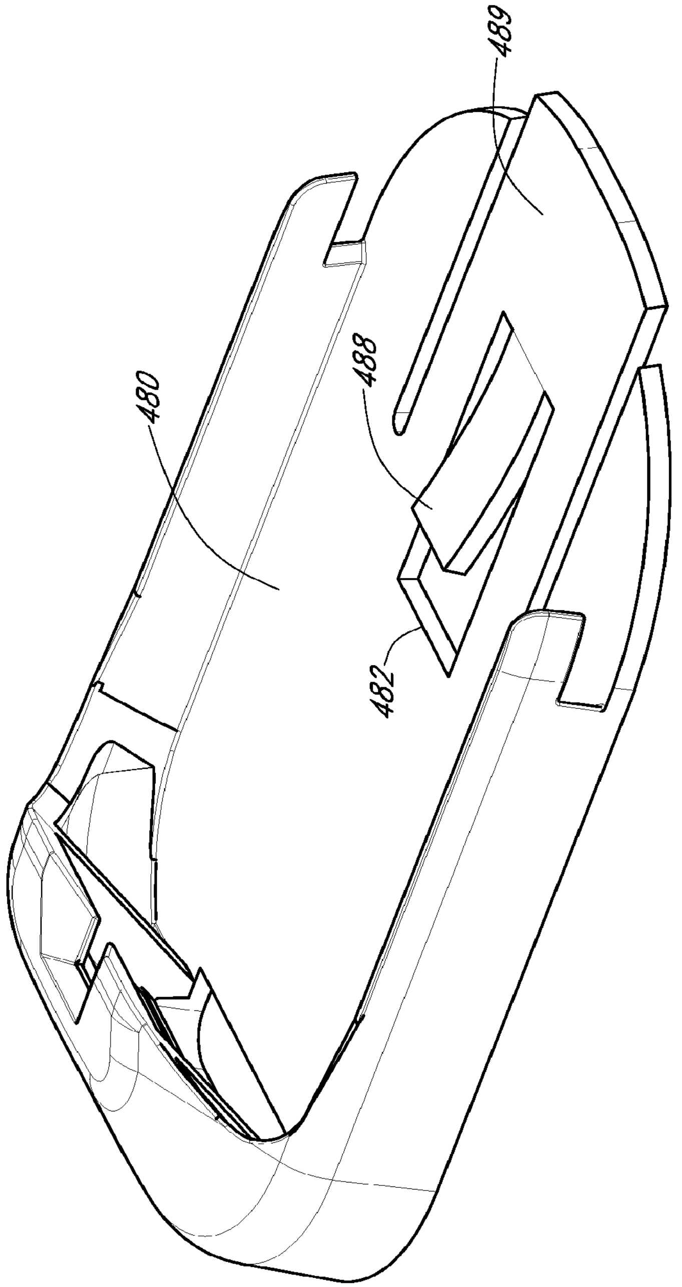

FIG. 12C shows an embodiment of the housing 480 having hole 482, a first tab 488, and a second tab 489 having features substantially the same as the corresponding structures discussed above. In this embodiment, the first tab 488 is bent so as to extend out of the general plane of the hole 482 and the second tab 489. The bent first tab 488 is advantageous because the first tab 488 is biased against the transmitter 500 to secure the transmitter 500 in the fully seated configuration.

Figure 12D:
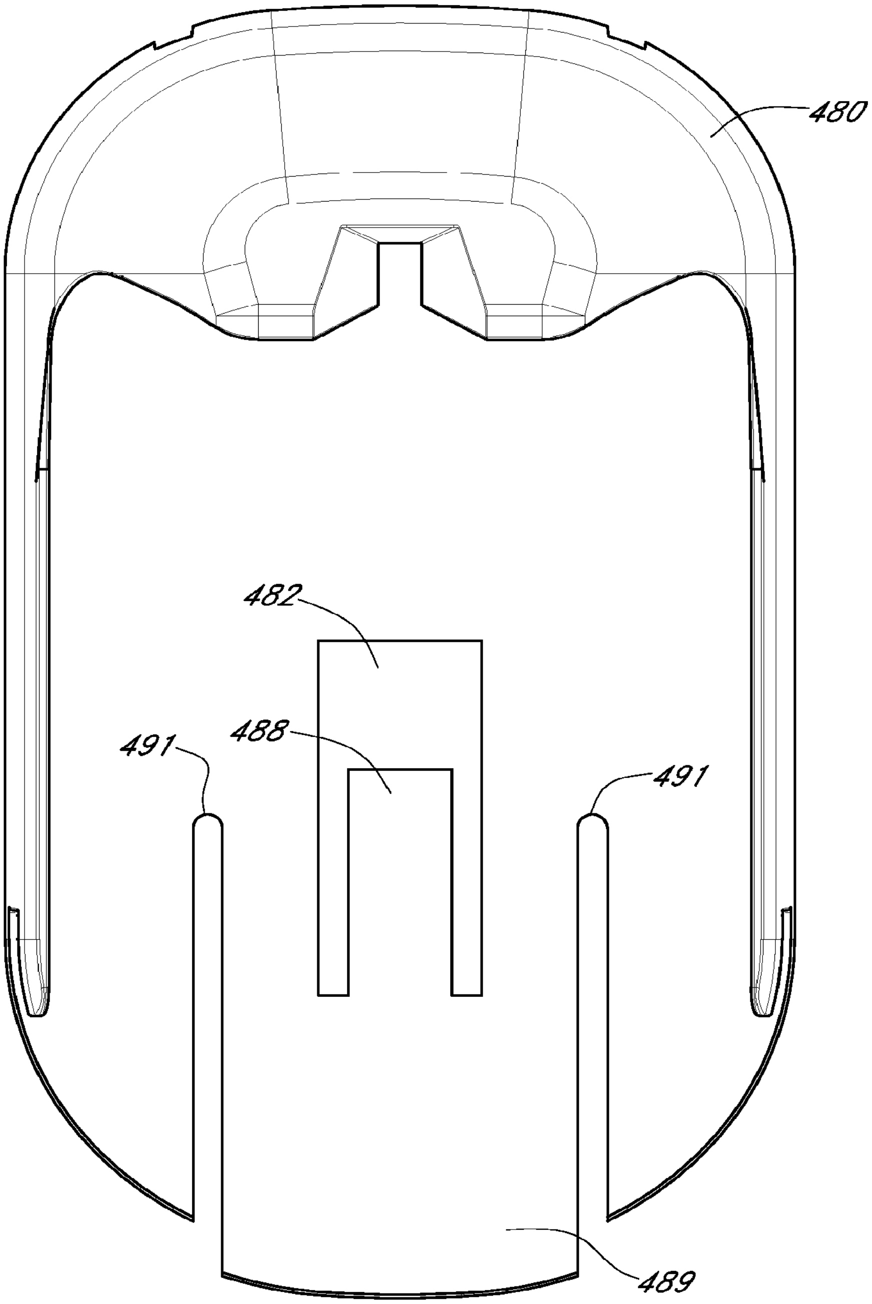

FIG. 12D shows an embodiment of the housing 480 having hole 482, a first tab 488, and a second tab 489 having features substantially the same as the corresponding structures discussed above. In this embodiment, the first tab 488 extends beyond the axis of rotation of the second tab 489 defined by a line intersecting the ends of slots 491. With this structure, as the second tab 489 is flexed and rotates, the end of the first tab 488 will press against the transmitter 500, presenting some resistance to the rotation. The resistance may be overcome by applying sufficient force to the second tab 489, and once the second tab 489 has rotated sufficiently, the transmitter will disengage from the housing 480 with an audible snap and sudden loss of resistance.

Figure 13A:
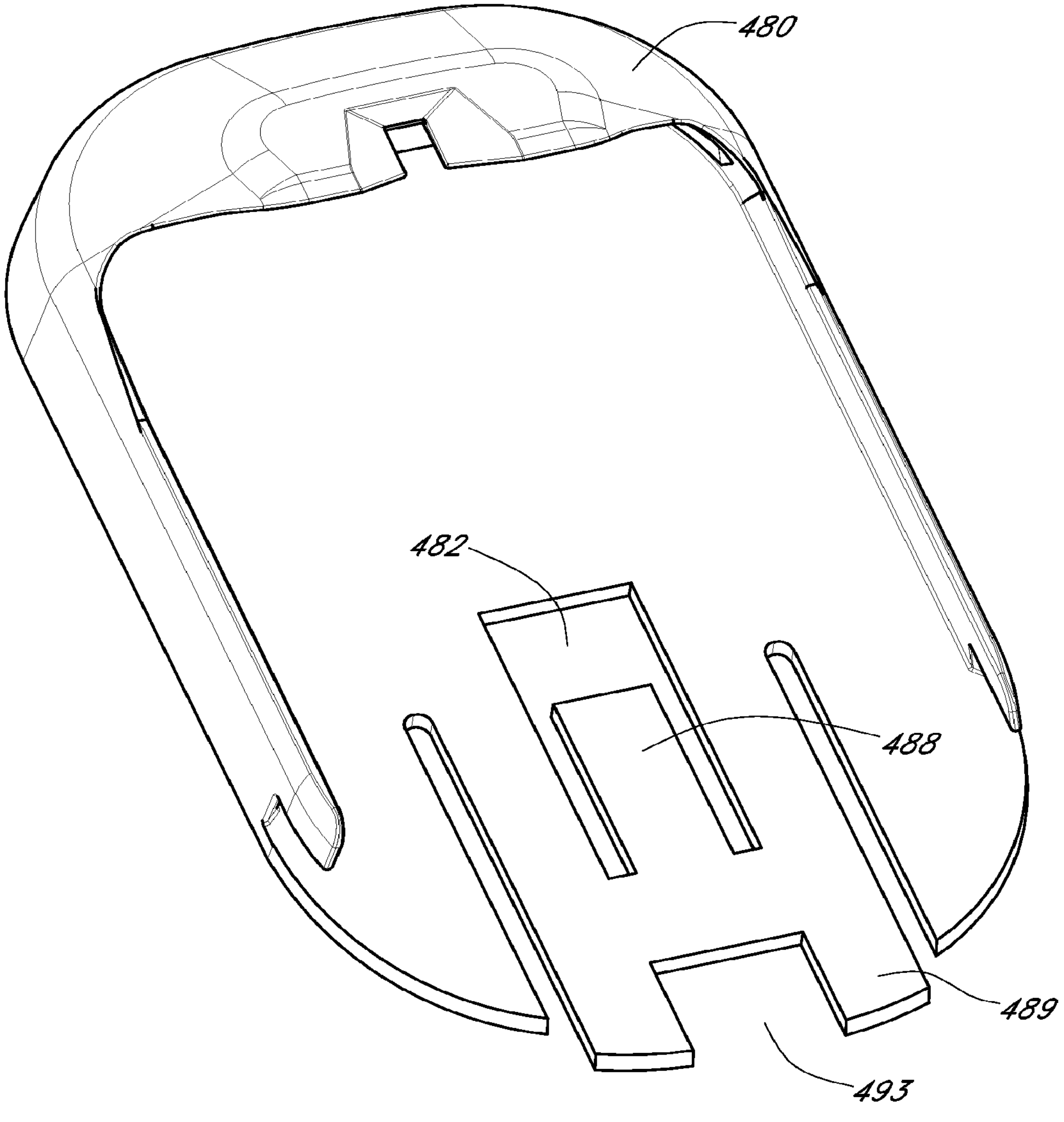
FIGS. 13A-13D are perspective views of a generally applicable embodiment of a housing.
Figure 13B:
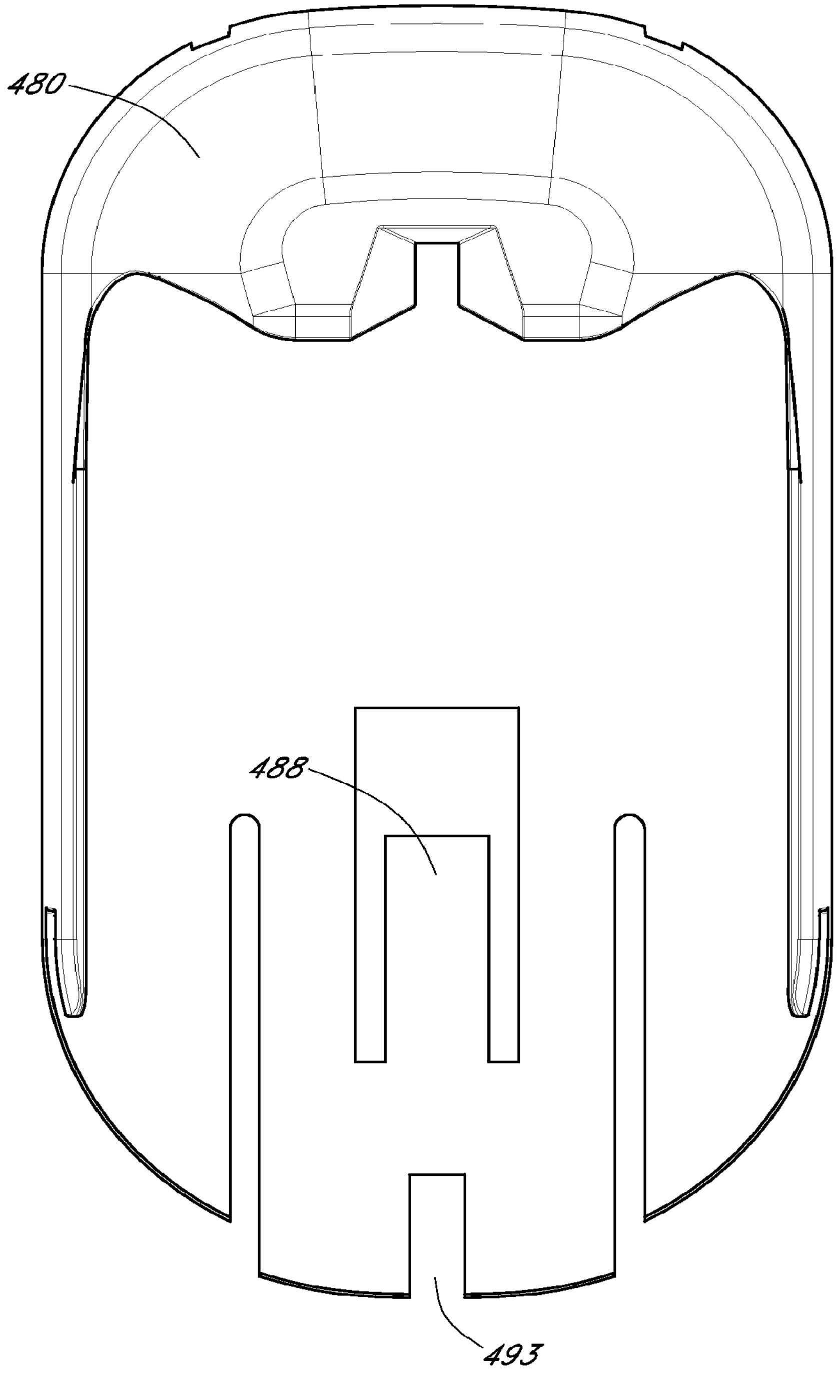
Figure 13C:
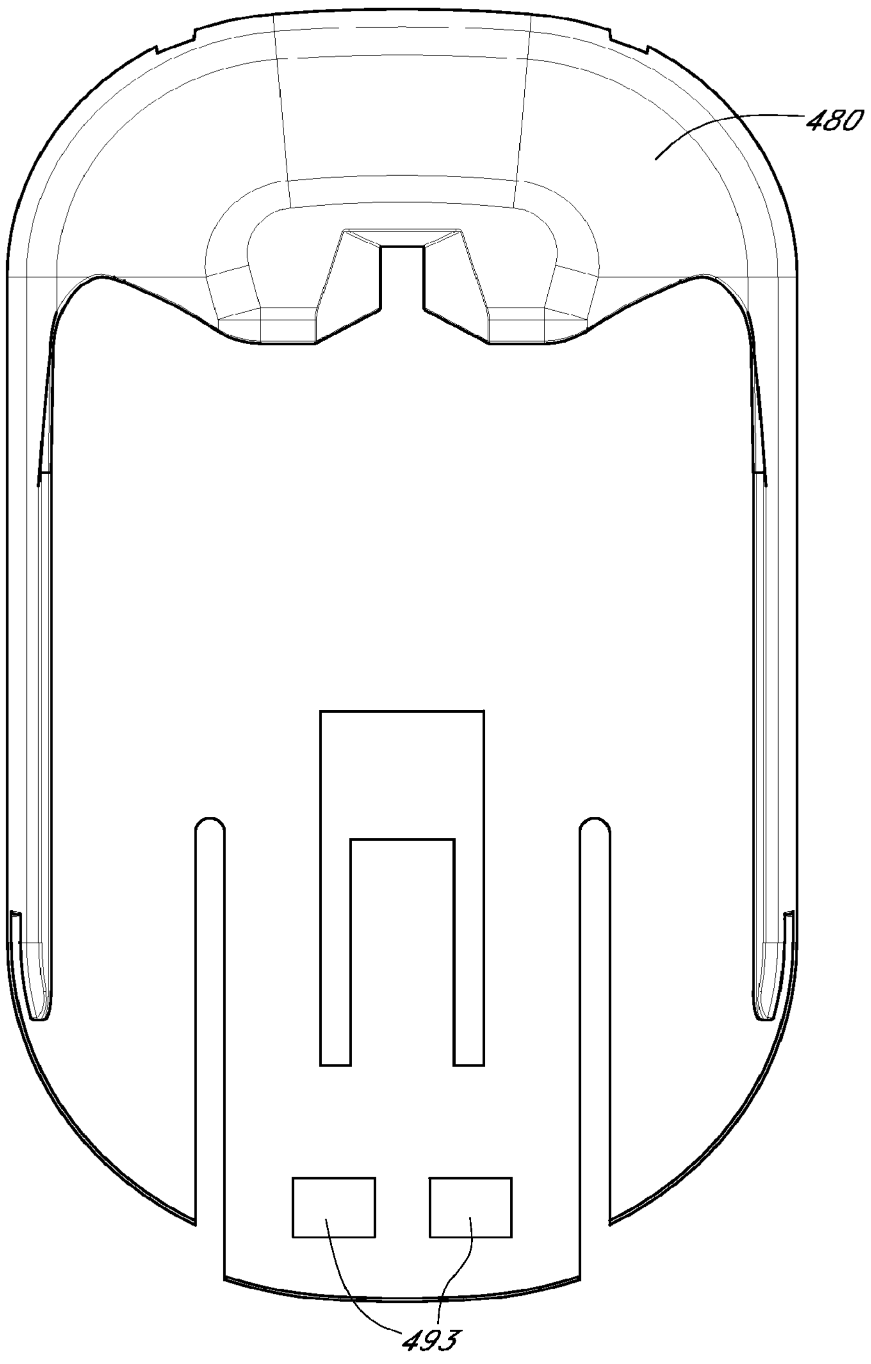
Figure 13D:
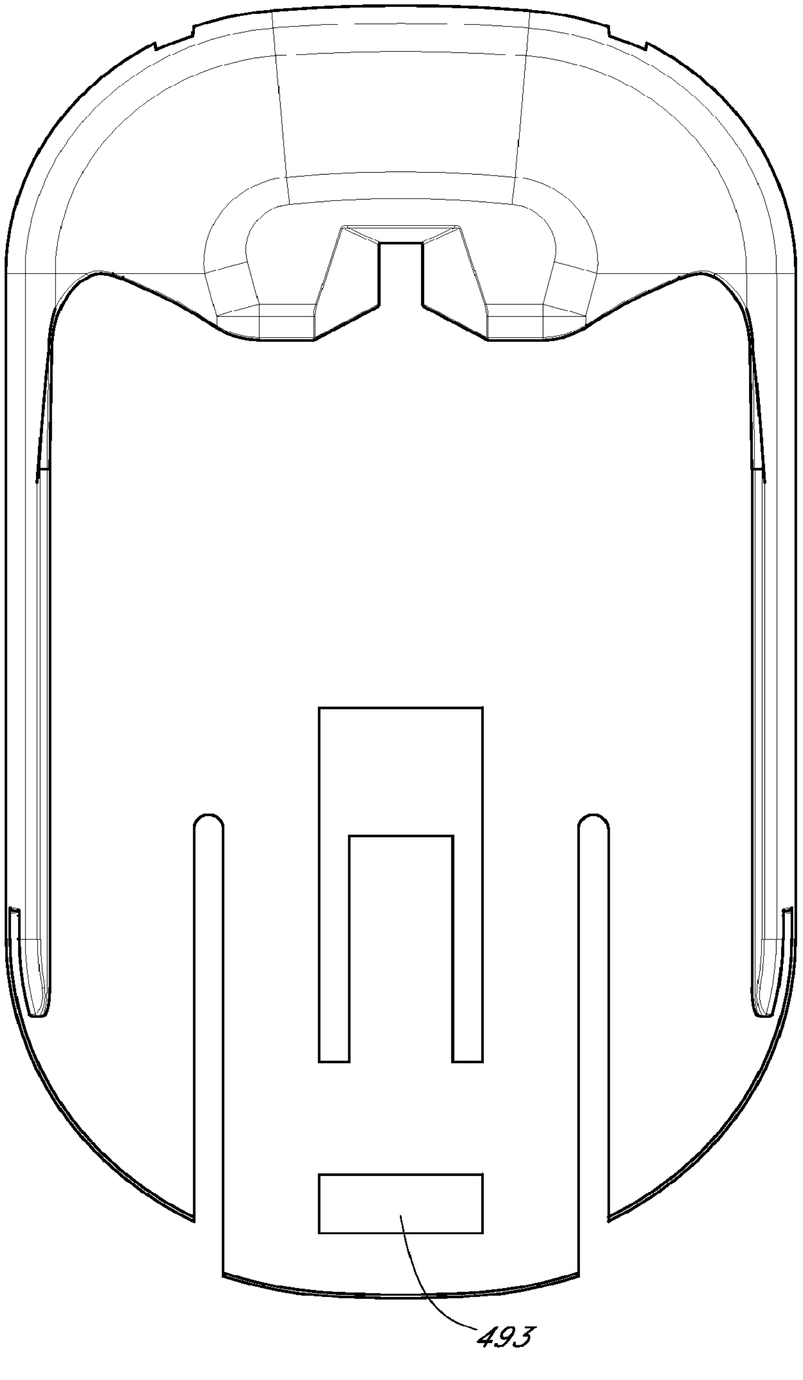

FIGS. 13A-13D show generally applicable embodiments of the housing 480 having a hole 482, a first tab 488, and a second tab 489 having features substantially the same as the corresponding structures discussed above with reference to FIGS. 12A-12D, and which features are applicable to all aspects and embodiments identified herein. Each of the embodiments of FIGS. 13A-13D also has a mechanism for securing the transmitter 500 to the housing 480 by engaging a second protrusion in the transmitter 500. The second protrusion engages the housing 480 at a cutout 493 so that the transmitter 500 may not or may not easily be released from the housing 480 until the system 600 is removed from the host even with the aid of a prying tool, such as a screwdriver. In the embodiments of FIGS. 13B and 13C the protrusion 510 does not engage the cutout 493 while the transmitter 500 is being fully seated in the housing 480.

Figure 14:
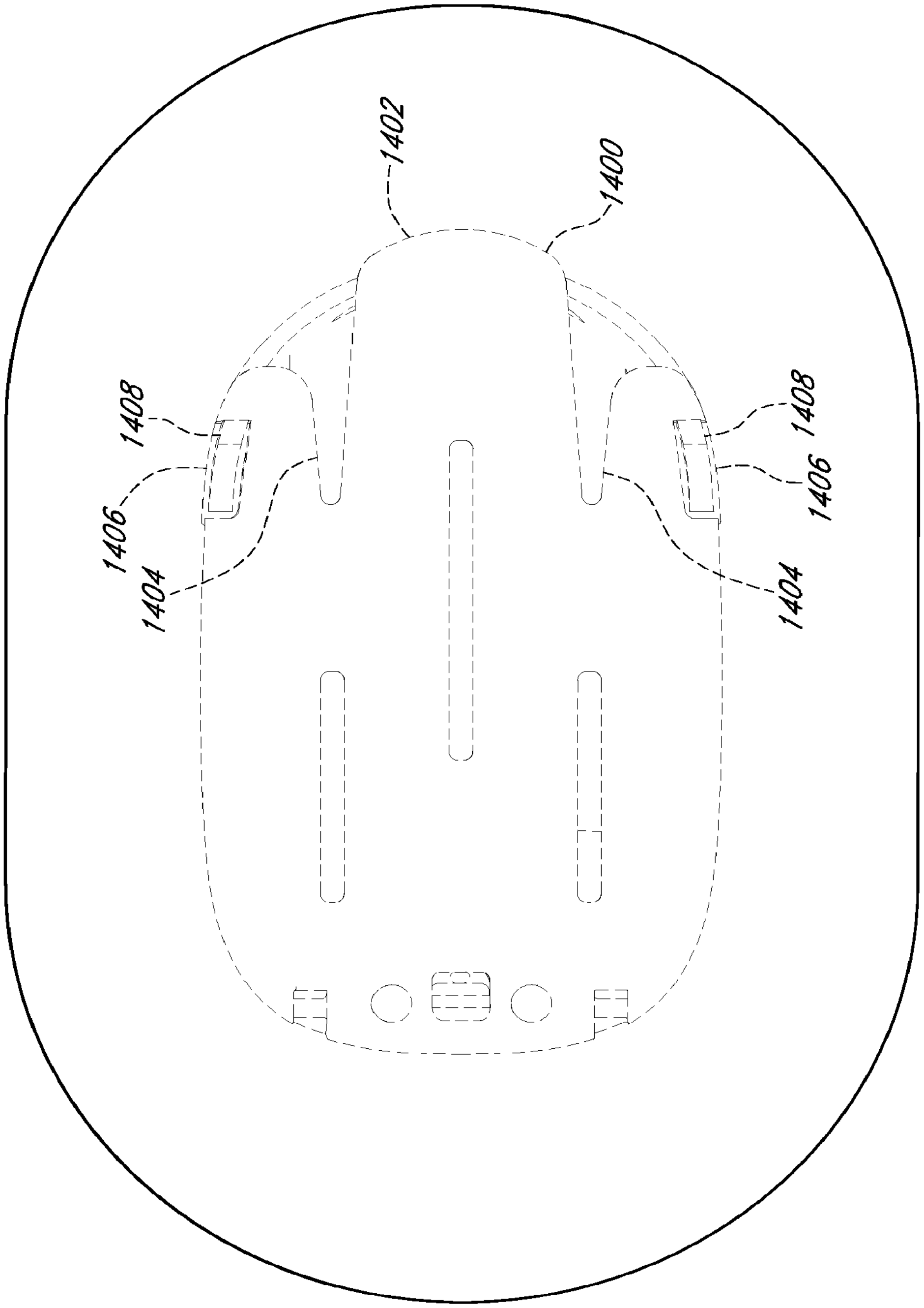
FIG. 14 is a lower plan view of a generally applicable embodiment of a housing.

FIG. 14 is a lower plan view of a generally applicable embodiment of a housing 1400, which embodiment is combinable, partly or wholly, with other embodiments described herein. The housing 1400 is substantially the same as the foregoing embodiments, except that the tab 1402 and the slots 1404 have more rounded contours, and the central hole 482 is replaced with a pair of apertures 1406 on opposite sides of the housing 1400. The apertures 1406 receive a pair of corresponding tabs 1408 on the transmitter 501 to secure the transmitter 501 to the housing 1400. The dual tab mechanism may provide a more secure hold for the transmitter 501 within the housing 1400. Further, to remove the device from the skin, the user pulls upward on the tab 1402. Thus, providing the slots on either side of the tab 1402 enables the tab 1402 to flex a certain amount without disengaging the tabs 1404 from the apertures 1406, thereby reducing the chance of accidentally removing the device from the skin.

The on-skin sensor assembly should be attached to a host for a limited period of time. Once the time expires, the assembly should be removed and possibly replaced. To prevent inappropriate reuse of the sensor, the applicator 400 and the on-skin sensor assembly have certain features. For example, in some embodiments, the transmitter 500 may not be removed from the housing 480 without destroying the housing 480. In some embodiments, the transmitter 500 may not be removed from the housing 480 without removing the adhesive patch from the housing 480 or from the host.

In some embodiments, when the system 600 is adhered to a user's skin, the skin blocks movement of a lever, which is used to remove the transmitter 500. The lever is clearly visible and easily accessible when the system has been removed for the user's skin, but it can't be used until the system 600 is removed. In this way, the transmitter can only be detached after the sensor is removed from the body (and is thereby rendered unusable).

In some embodiments, the sensor electronics within the transmitter 500 are programmed to analyze the signal, for a signal characteristic that indicates a sensor has been removed (or inserted) for example, near-zero signal (or characteristic break-in signature). When the sensor electronics detect that a sensor has been removed (or inserted) based on analysis of the signal, certain algorithms can be responsive thereto. For example, the sensor electronics can be programmed to turn off the system after the expiration and/or ensure removal of the expired sensor from the host.

In some embodiments, the applicator 400 is packaged for distribution with the housing 480 and seal 475 therein. In some embodiments, the packaging is at least partially integrated with the applicator 400.

For example, the packaging for the applicator 400 may include the front cover 410 and the back cover 450. In some embodiments, the port into which the transmitter 500 is inserted is covered, for example, by a door Likewise, the port through which the sensor is inserted into the host may be covered, for example, by a door. In some embodiments, one or more of the doors is removable, for example, with a pull tab.

In some embodiments, the packaging includes liner 490. Accordingly, to use the applicator 400, the applicator 400 is removed from the packaging liner 490 and applied to the host. In this embodiment, removing the applicator 400 from the packing liner 490 exposes the adhesive on the adhesive patch 485. In some embodiments, the packaging liner is only releasable when the transmitter 500 is pre-seated, or partially seated, for example the liner 490 may be covered by a shield which moves to expose the liner once the transmitter 500 is partially seated. In some embodiments, the packaging liner 490 includes instructions for use. In some embodiments, multiple applicators 400 are included on the same packaging liner. For example, 2, 4, 8, or 12 applicators may be included on the same packaging liner, for example, via perforated attachment, whereby a kit is provided.

In some embodiments, the applicator includes a protective cover that attaches to the housing. The protective cover may protect the electronics unit and the insertion point on the host from dirt, sand, water, etc. The internal portion of the protective cover may conform to the shape of the applied on-skin sensor assembly 600. In some embodiments, the cover includes multiple or composite layers, and may be waterproof or water resistant, and may further be air permeable. In some embodiments, the cover is decorative in its shape, color, and color patterns. For example, the cover may have an appearance of an animal or a character, e.g., a cartoon character or other animated character. The protective cover may have an adhesive that attaches the protective cover to the adhesive patch 485. In some embodiments, the cover is designed to shift the weight or volume off-center, to avoid "hot spots" associated with the pressing of the edges of the housing on the skin, thereby avoiding compression artifacts that may occur in the vicinity of the sensor insertion site.

In some embodiments, the applicator inserts the sensor into the host and detaches from the housing in response to the trigger being activated, but does not seat the transmitter. In such embodiments the transmitter is seated into the housing after the applicator has detached from the housing. A mechanism described herein may be used to seat the transmitter into the housing.

In some embodiments, the applicator has a size and shape so that it is configured to substantially fit within a palm of a hand, for example, like a computer mouse. Because of the ergonomic shaping, the applicator is held with a flat wrist, while allowing the trigger to be released. A user can fully insert the sensor, including transmitter attachment and optionally start of sensor session with a single hand at any location on the body reachable by hand, even locations that are awkward to reach.

In some embodiments, once applied, the housing 480 substantially fully encapsulates the transmitter 500 against the host. In such embodiments, the transmitter 500 is inserted into the housing 480 from the host side of the applicator 400. In some embodiments, the housing 480 forms a shell which encloses a drawing mechanism and includes a septum through which the needle inserts the sensor. As with the embodiments discussed above, activation of a trigger causes the needle to insert the sensor, and the transmitter to secure the sensor such that the sensor electrically contacts the transmitter.

In some embodiments, an alternative sensor insertion mechanism is used. The alternative sensor insertion mechanism is driven by an action from the user instead of using energy stored in a spring, which alternative sensor insertion mechanism is combinable, partly or wholly, with other embodiments described herein. Accordingly, energy for the insertion movements is provided by the user. For example, to cause a needle to insert a sensor, the user may squeeze the applicator or otherwise cause movement of a needle carrier. Movement of the needle carrier causes the needle to be inserted into the host and to be removed from the host. Movement of the needle carrier may also cause results as those discussed above, such as movement of a transmitter standoff and seating of the transmitter into the housing. At the end of the movement of the needle carrier, the needle carrier may press against a bumper so as to cause the deceleration of the needle carrier to be limited instead of generating a shock which would be translated throughout the applicator.

Figure 15:
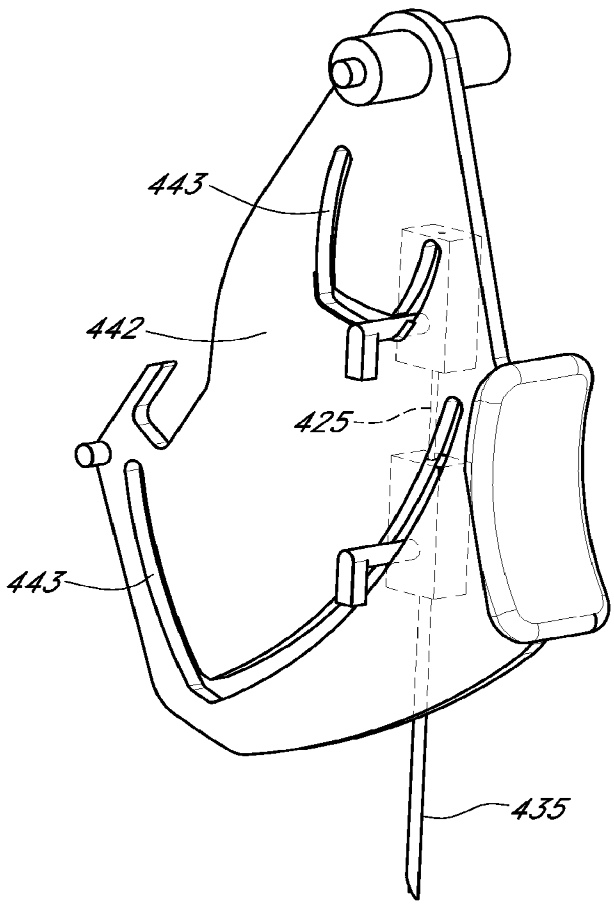
FIG. 15 is a front perspective view of a needle carrier for use in an applicator.
Figure 16A:
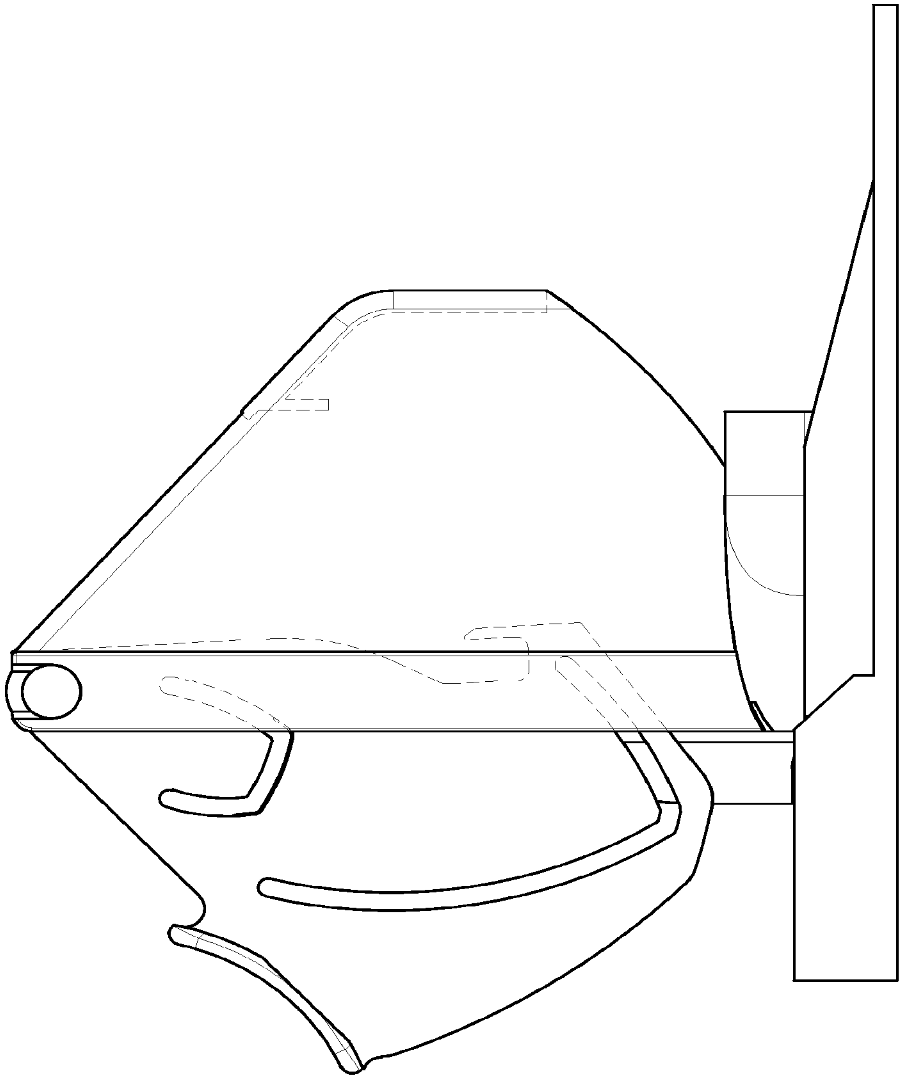
FIGS. 16A-16D are side elevation views showing use of the needle carrier of FIG. 15.
Figure 16B:
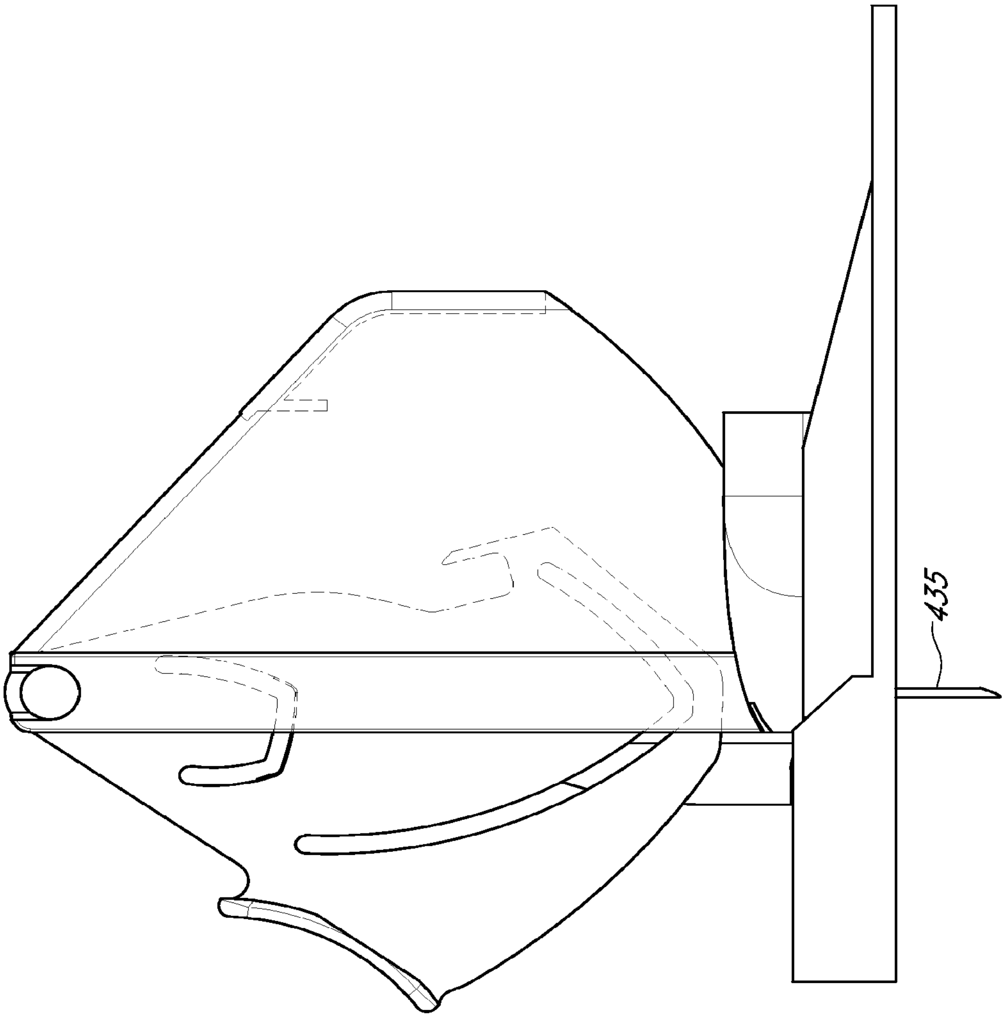
Figure 16C:
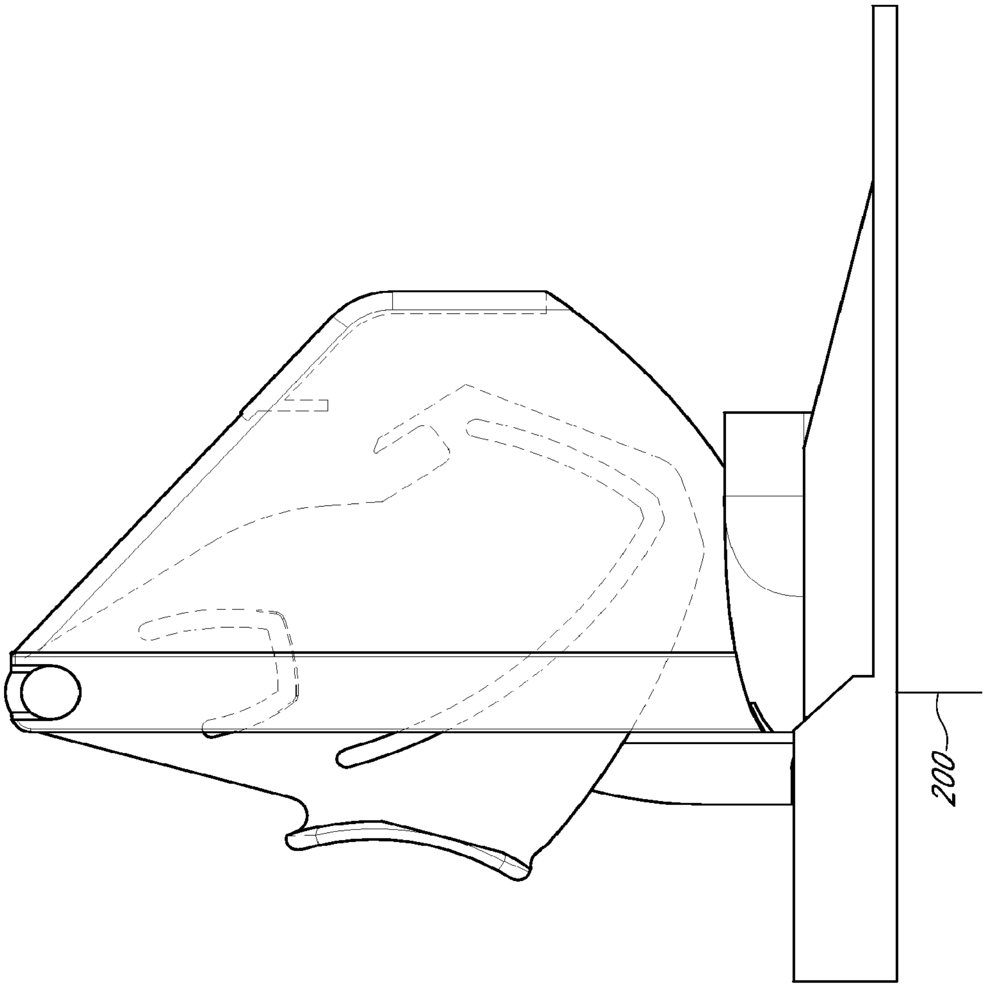
Figure 16D:
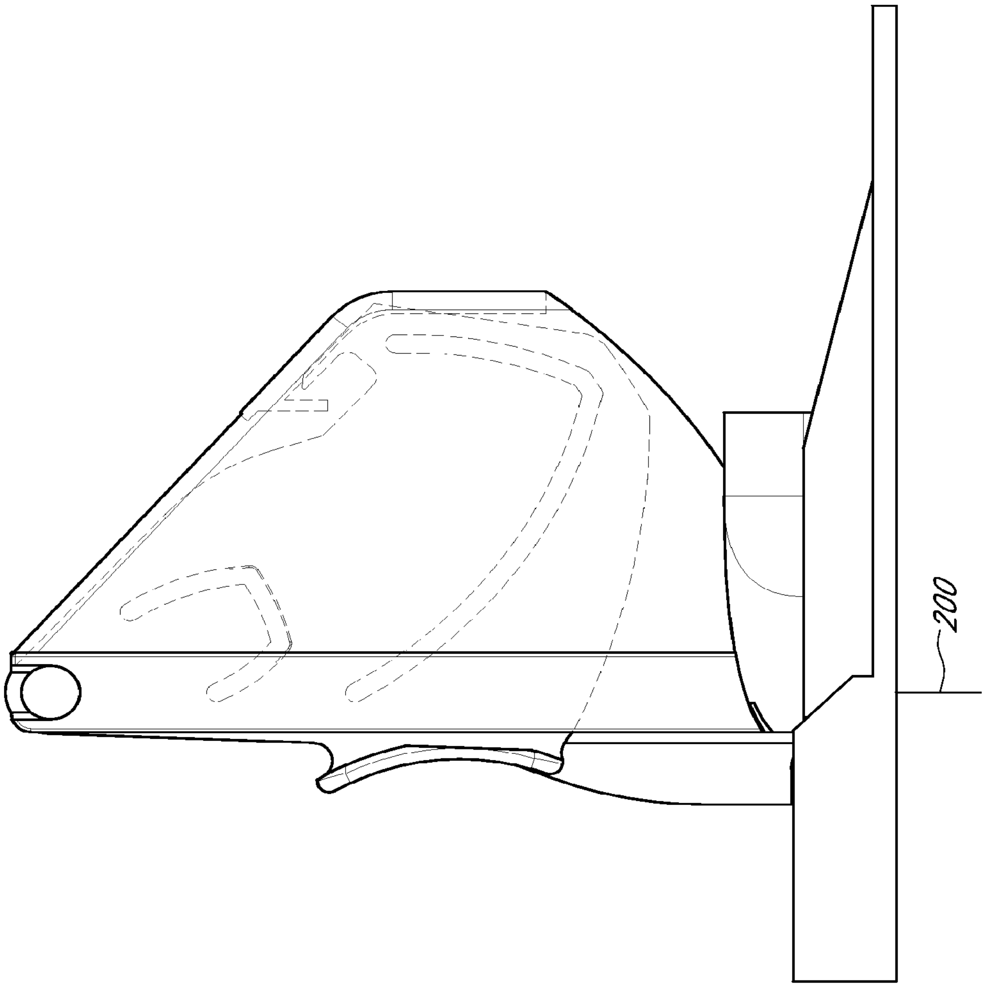

FIG. 15 is a perspective view of another sensor insertion mechanism, utilizing a cam path and cam follower to guide sensor and needle insertion with subsequent needle retraction, which embodiment includes features that are combinable, partly or wholly, with other embodiments described herein. FIG. 15 shows an example of a needle carrier 442, which is a cam with two slots 443. In embodiments using a cannula, a third slot may be formed. The slots 443 guide the motion of the needle 435 and pushrod 425 by engaging followers. This allows one squeezing motion to translate to complex in-and-out movements of the needle 435 and pushrod 425 without springs or locking mechanisms. FIGS. 16A-16D are perspective views of the needle carrier of FIG. 15 showing use of the needle carrier 442, which feature is combinable, partly or wholly, with other embodiments described herein. In FIG. 16A the applicator is ready for actuation. In FIG. 16B the needle 435 is inserted into the host. In FIG. 16C the needle 435 is retracted, leaving the sensor 200. In FIG. 16D the needle 435 is retracted so as to not be exposed once the applicator is removed. In some embodiments, the movement of the needle carrier 442 also causes the transmitter 500 to be fully seated and to be compressed against an elastomeric seal to seal and secure the sensor 200, such as described above.

Aside from cost and reliability advantages, a cam needle carrier results in a smoother feel. The slots allow nonlinear translation of squeezing to needle movement. For example, a greater mechanical advantage could be given for inserting the needle than for withdrawing the needle. In some embodiments, the needle relatively slowly punctures the skin of the host, and then quickly reaches its full depth to improve the perception of accuracy or reduce the perception of insertion depth.

As shown, the pivot point is at the top of the needle carrier 442. In some embodiments the pivot point is placed at the bottom or the middle. Mechanical advantage and speed of actuation can be tuned by varying the distance of the slots from the pivot point, by varying the distance of where the user pushes the needle carrier 442 from the pivot point, and by varying the angle of cam rotation for each movement, for example, by making the slots steeper or shallower. The pivot point is also shown in line with the followers, but in some embodiments, it is offset to adjust mechanical advantage.

Figure 17A:
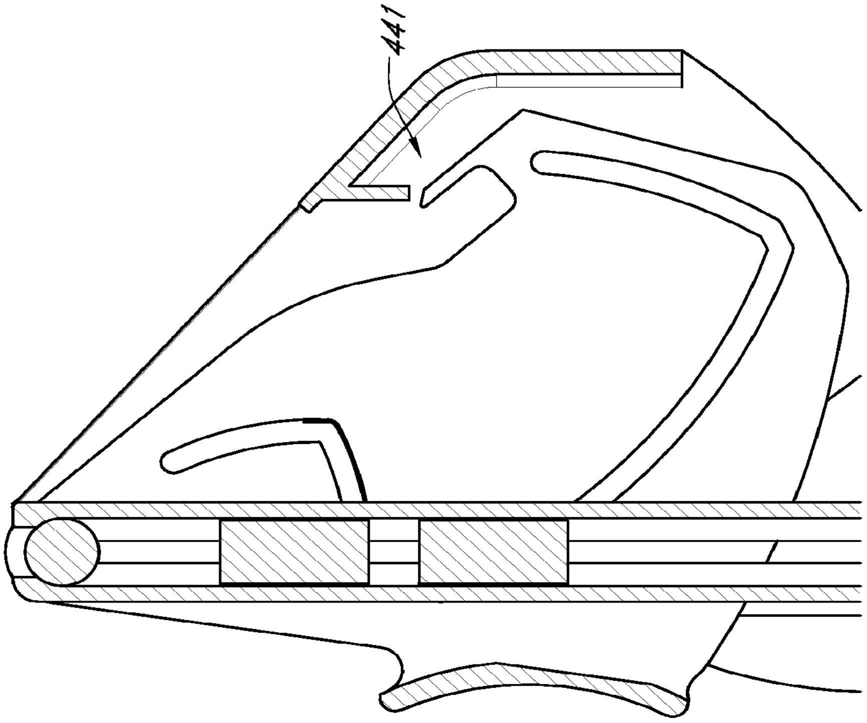
FIGS. 17A and 17B are cross-sectional side views of a generally applicable embodiment of an applicator showing a latching mechanism for the needle carrier.
Figure 17B:
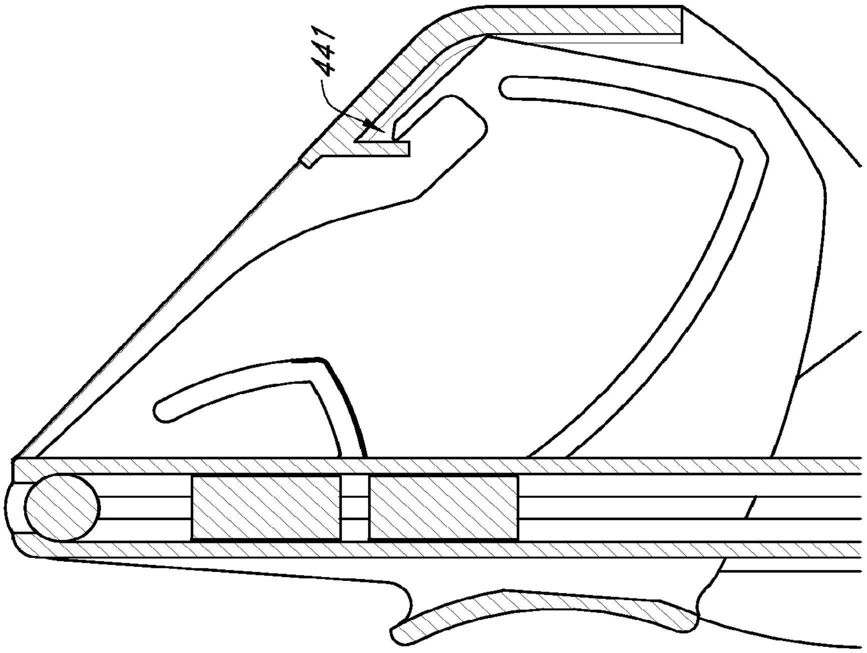
Figure 18:
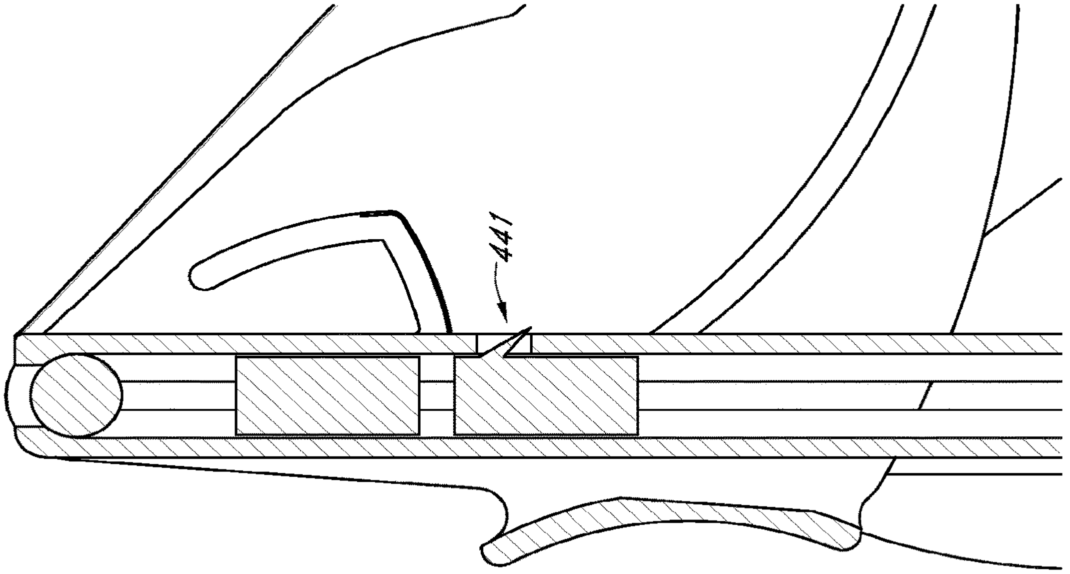
FIG. 18 is a cross-sectional side view of a generally applicable embodiment of an applicator showing a latch design.

FIGS. 17A and 17B are perspective views of the applicator showing a latching mechanism for the needle carrier, which feature is combinable, partly or wholly, with other embodiments described herein. The applicator may be made stick-proof by including a latch 441 at the end of the stroke to lock the cam in its final position. In some embodiments, the latch is flexible and built into the cam, such as that shown in FIGS. 17A and 17B. FIG. 18 is a perspective view of the applicator showing another embodiment of a latch 441, which embodiment is combinable, partly or wholly, with other embodiments described herein.

Figure 19A:
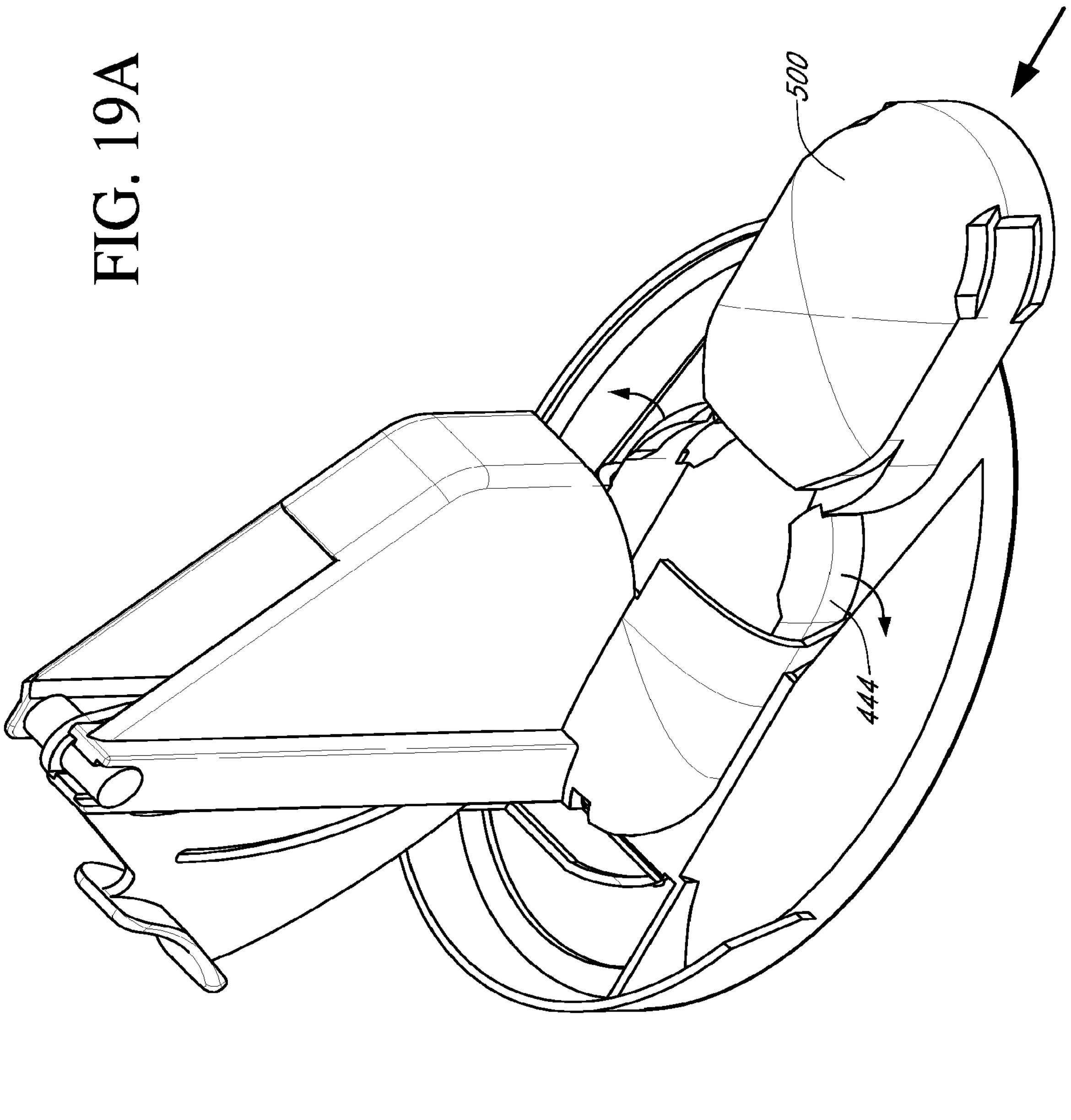
FIGS. 19A and 19B are rear perspective views of a generally applicable embodiment of an applicator and sensor system, illustrating a process for inserting the sensor system into the applicator.
Figure 19B:
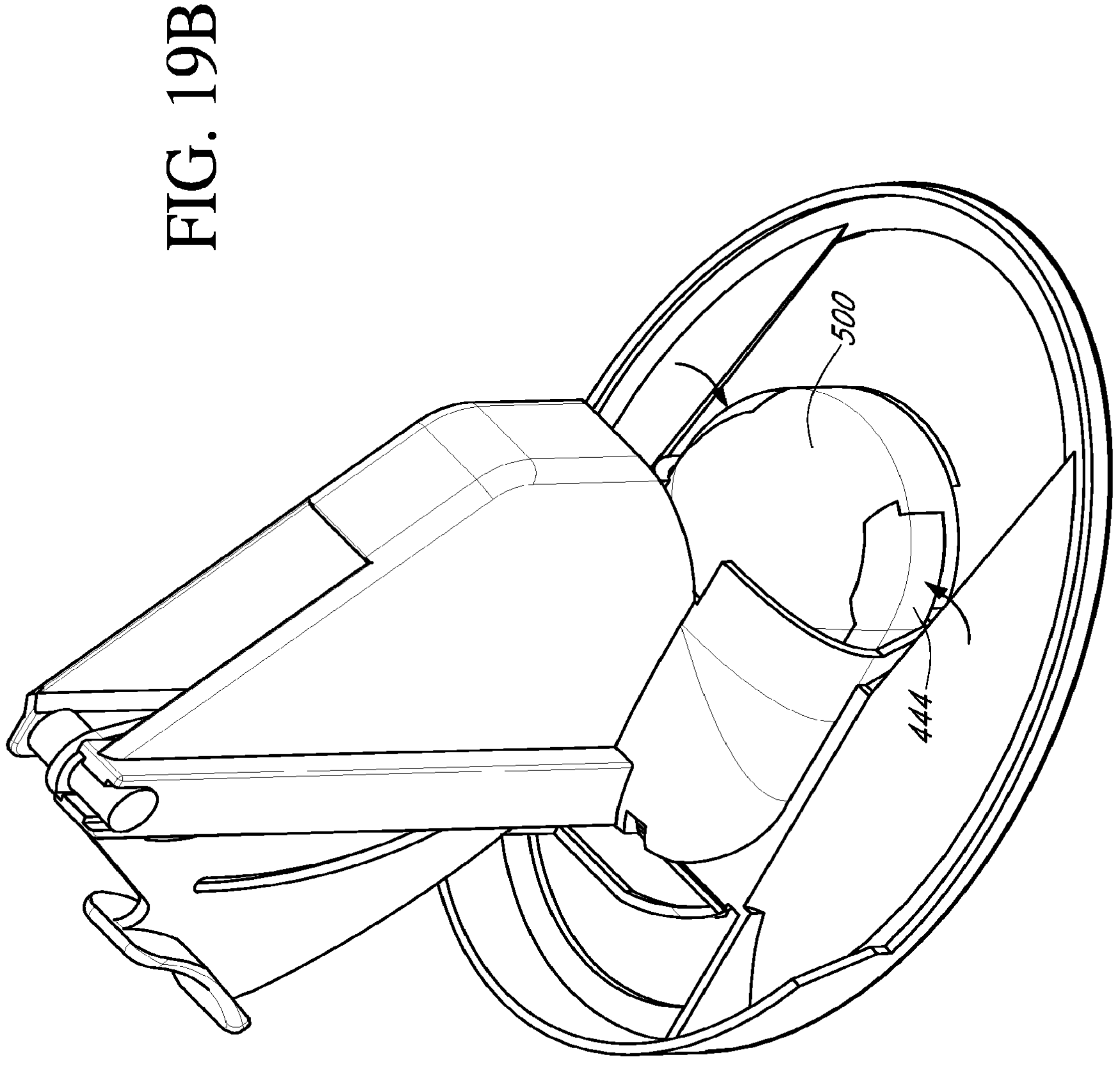
Figure 20A:
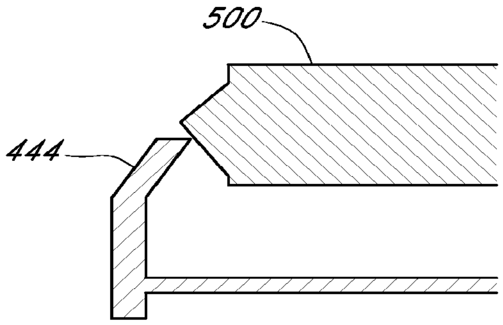
FIGS. 20A-20C are cross-sectional views of a mechanism for drawing a transmitter into a housing.
Figure 20B:
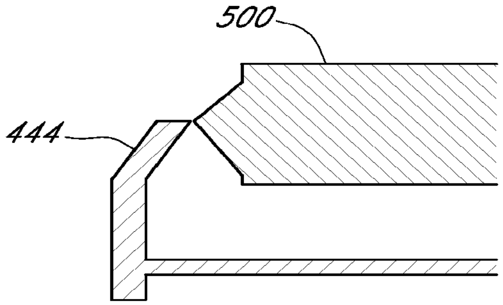
Figure 20C:
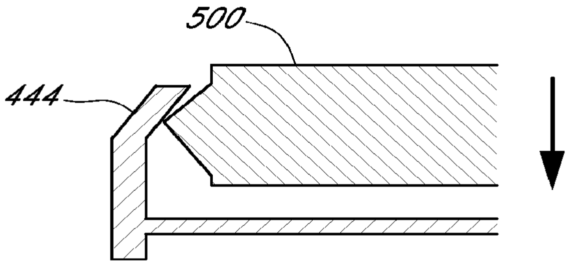

FIGS. 19A and 19B are perspective views of an embodiment of an applicator, which embodiment includes features that are combinable, partly or wholly, with other embodiments described herein. As shown, flexible arms 444 draw in and hold the transmitter 500. FIGS. 20A, 20B, and 20C are perspective views of a mechanism for drawing in the transmitter 500 into the housing. FIGS. 20A, 20B, and 20C show an embodiment of the arms 444 engaging the transmitter 500, which features is combinable, partly or wholly, with other embodiments described herein. In such an embodiment the transmitter 500 is not required to travel unnecessarily. In addition, the elastomeric seal can be thinner, and may not be compressed. Furthermore the arms can be formed to generate as much force as needed, so that the force applied to the device after insertion is not dependent on the user.

Figure 21A:
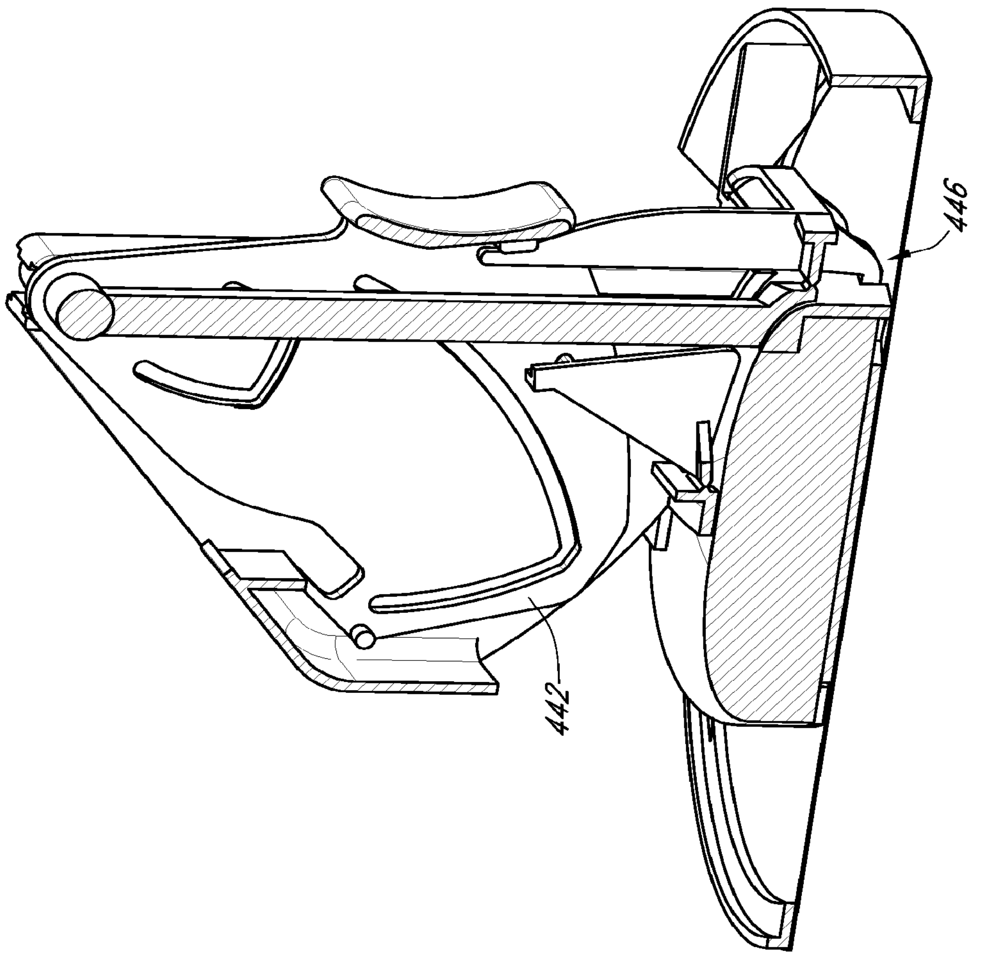
FIGS. 21A-21C are side perspective views of a generally applicable embodiment of a latch for an applicator.
Figure 21B:
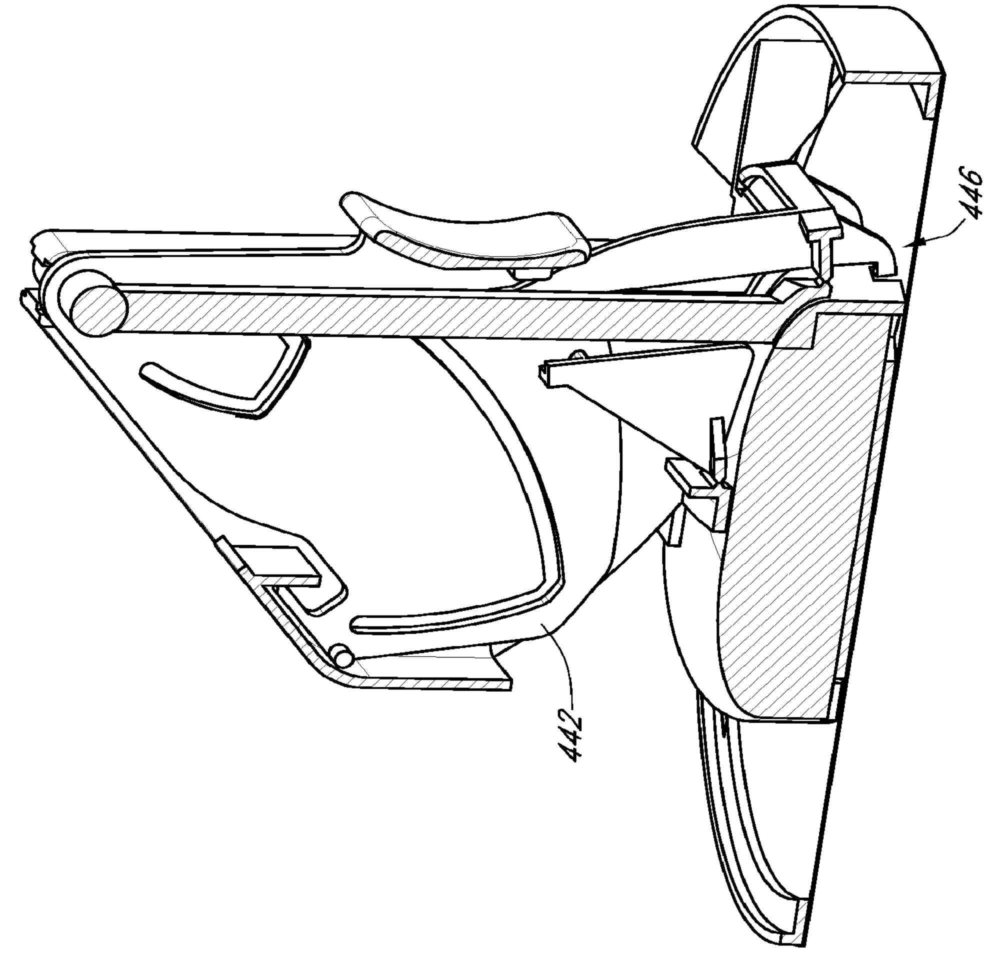
Figure 21C:
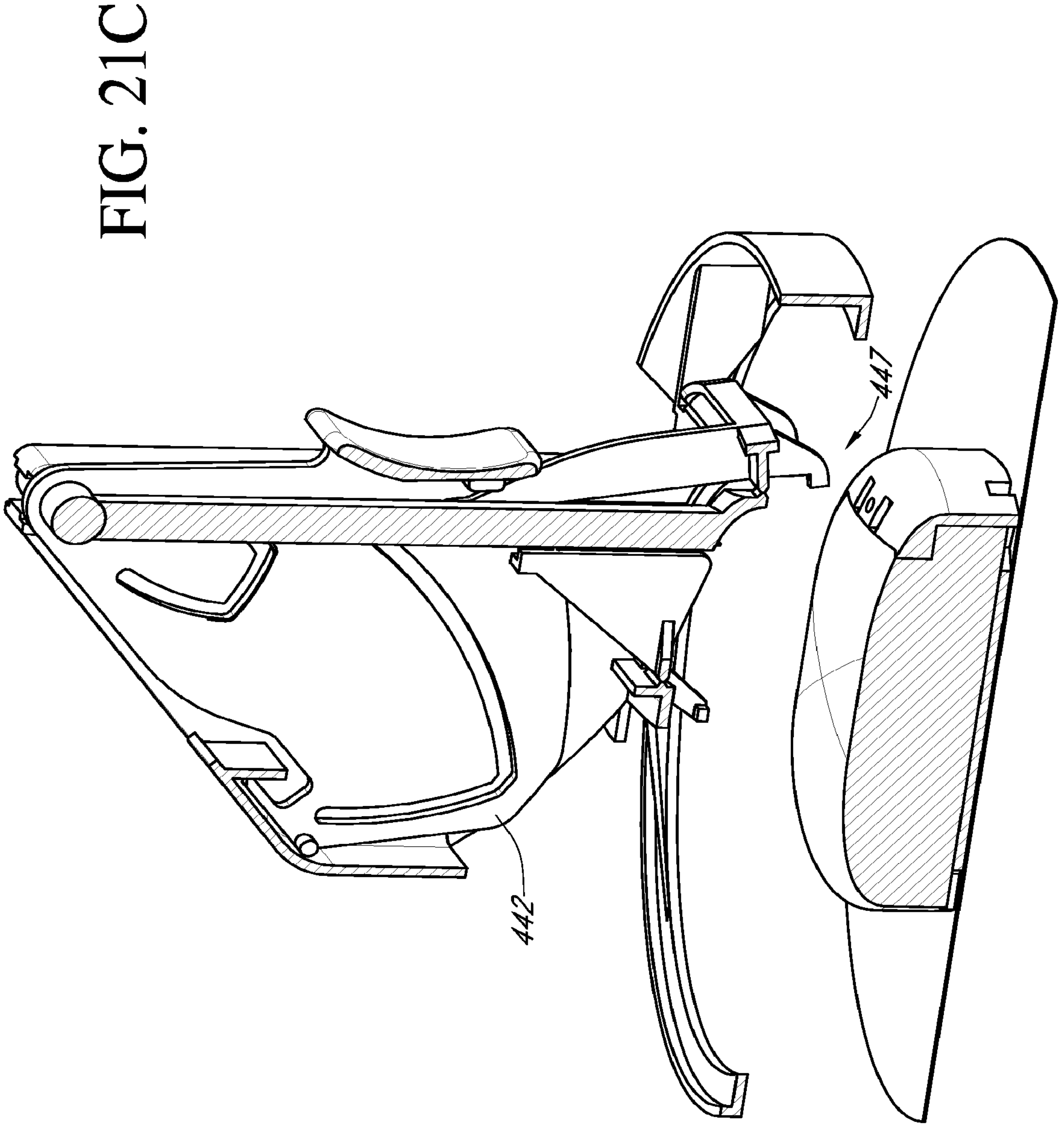

Detachment from the transmitter 500 and the housing 480 may be caused by the cam rotation. For example, at the end of the cam movement, a latch may be released to disengage the transmitter 500 and the housing 180. FIGS. 21A, 21B, and 21C are perspective views of an embodiment of a latch for a cam, which embodiment is combinable, partly or wholly, with other embodiments described herein. As shown in FIGS. 21A, 21B, and 21C, a front latch 446 is opened by the cam 442. In addition a rear latch 447 is manually unhooked by pivoting the cam 442 up. In some embodiments, a bump or ramp on the cam 442 causes the cam 442 to push up, giving a clear indication that it is released. Alternatively, the applicator could have an integral spring to push it up and away upon release. The front or rear latches could be modified accordingly. A spring interacting with the transmitter 500 would be advantageous because plastic would not be held under stress during sterilization and shelf life, which could cause the plastic to loose its spring force.

Figure 22A:
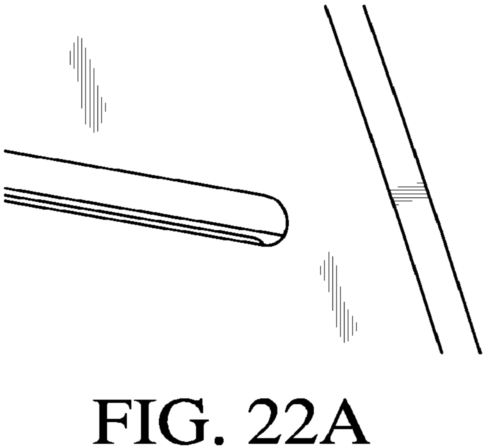
FIGS. 22A-22C are side perspective views of generally applicable embodiments of mechanisms for reducing play in the needle carrier of FIG. 24.
Figure 22B:
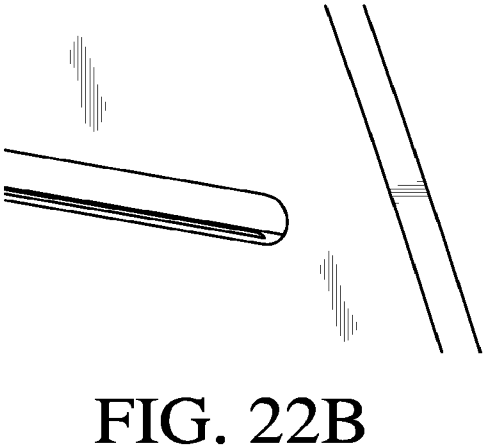
Figure 22C:
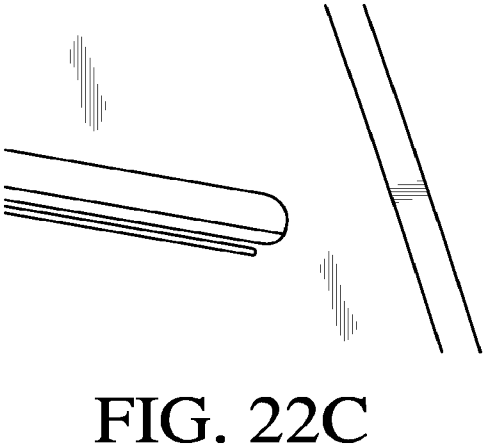

The cam followers slide freely in the slots responsive to manual (user-controlled) and/or automated (e.g., spring-controlled) force. FIGS. 22A, 22B, and 22C are perspective views of embodiments of mechanisms for reducing play without tight tolerance parts, the slots may include a deformable lip which applies a force against the followers, which mechanisms are combinable, partly or wholly, with other embodiments described herein. FIGS. 22A and 22B show embodiments of lips. In addition a relief cut, near each slot may allow for the slots to flex to reduce play. FIG. 22C shows an embodiment of a relief cut.

Figure 23A:
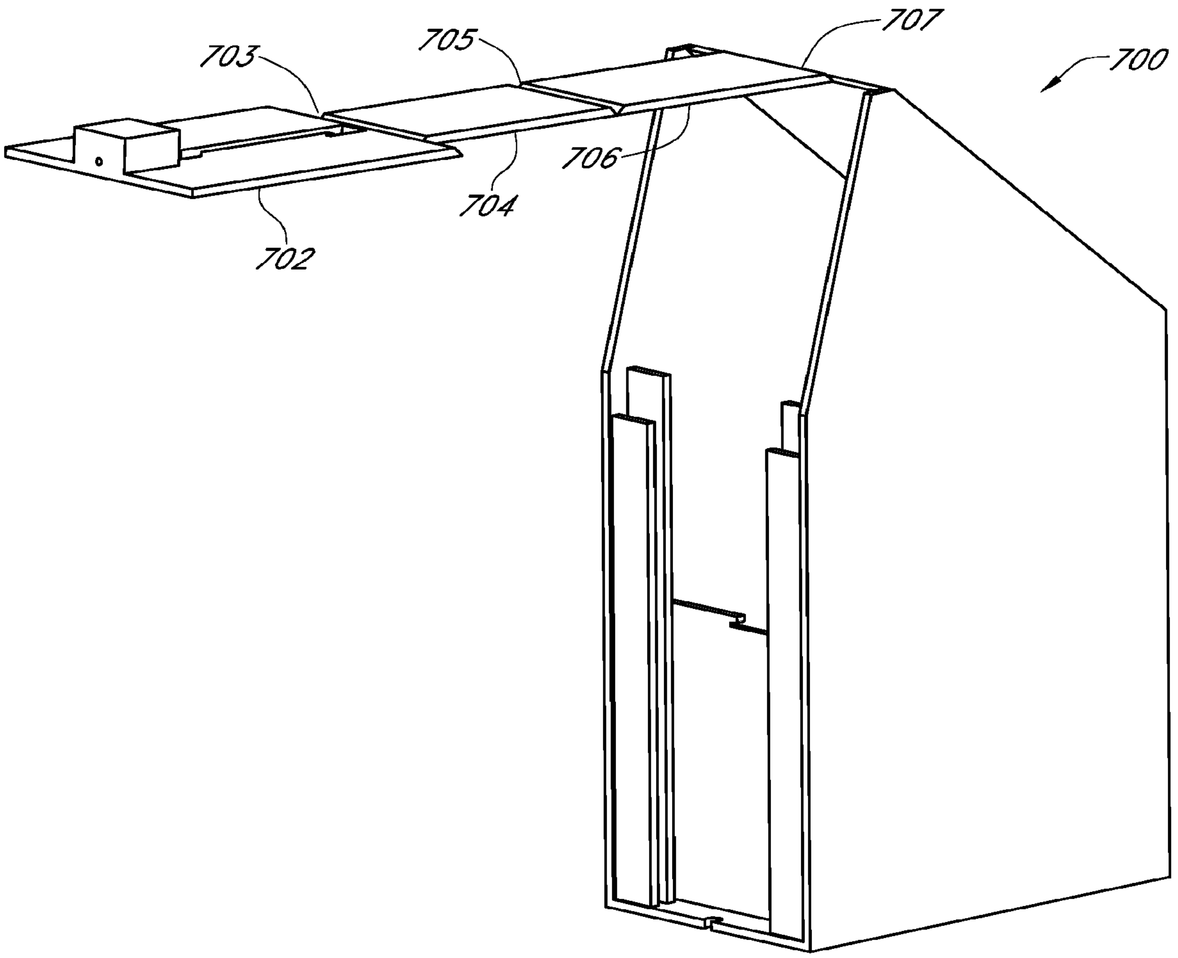
FIGS. 23A and 23B are front perspective views of a generally applicable embodiment of a sensor insertion mechanism.
Figure 23B:
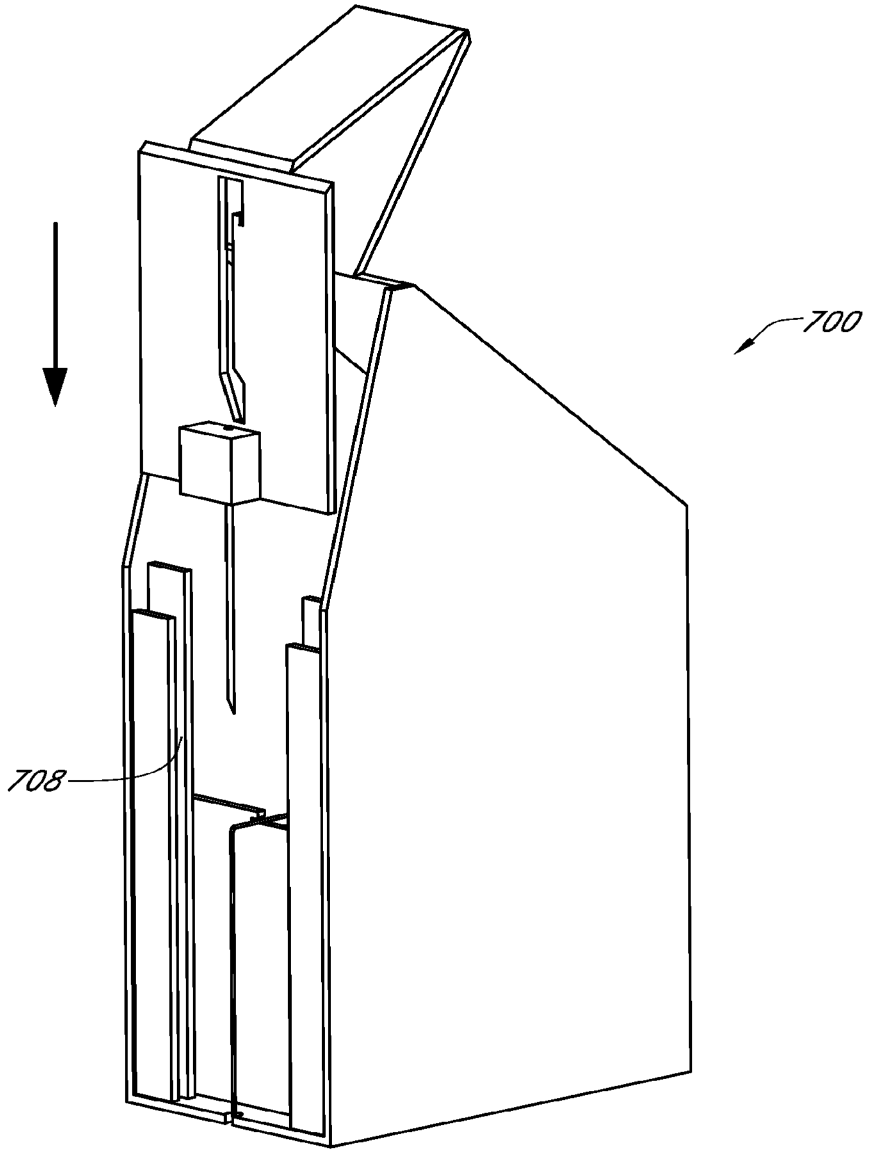
Figure 24A:
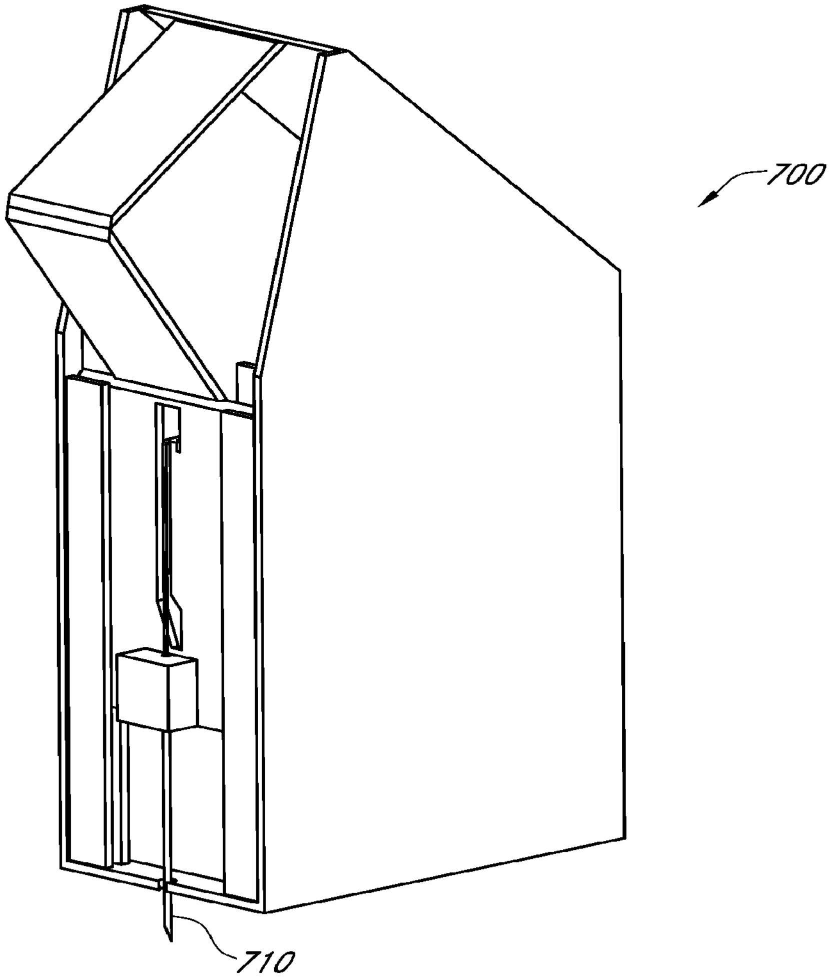
FIGS. 24A-24C are front perspective views showing actuation of the mechanism of FIGS. 23A and 23B.
Figure 24B:
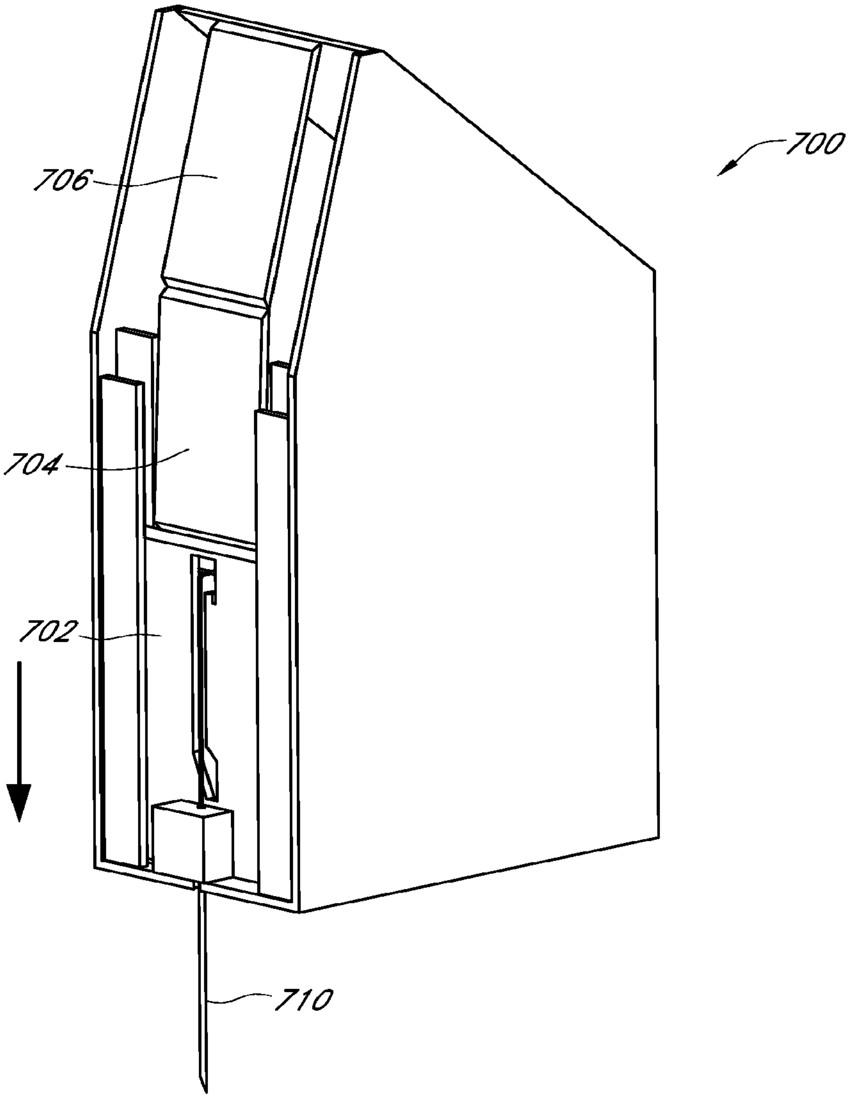
Figure 24C:
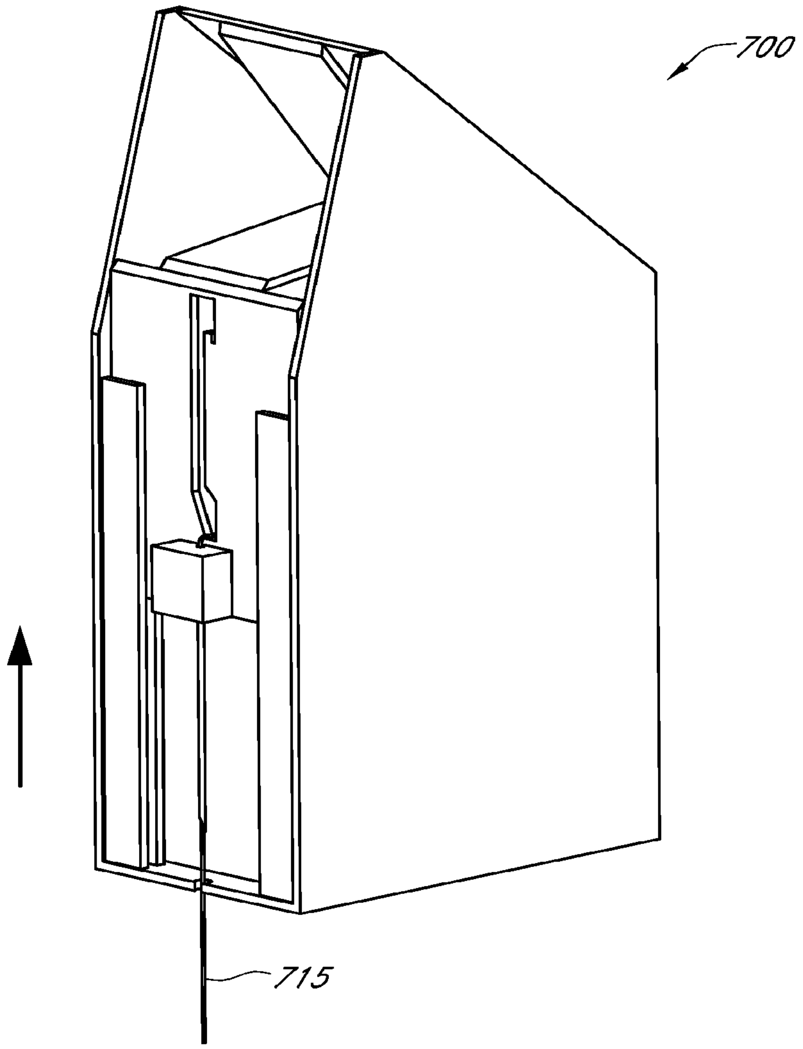

FIGS. 23A and 23B are perspective views of an embodiment of a sensor insertion mechanism 700, which embodiment includes features that are combinable, partly or wholly, with other embodiments described herein. The mechanism 700 is formed from a single plastic part to which a needle and a pushrod are attached. The mechanism 700 includes three movable sections 702, 704, and 706, separated by live hinges 703, 705, and 707. FIG. 23B shows the movable sections inserted into a vertical slot 708. FIGS. 24A, 24B, and 24C are perspective views showing actuation of the mechanism 700. In FIG. 24A, the mechanism 700 is ready for actuation and is placed on the host. In FIG. 24B, section 706 is rotated causing sections 704 and 702 to move toward the host, and causing the needle 710 to be inserted into the host. In FIG. 24C, section 706 is further rotated causing sections 704 and 702 to move away from the host, and causing the needle 710 to be retracted from the host, leaving the sensor 715 in the host.

Figure 25A:
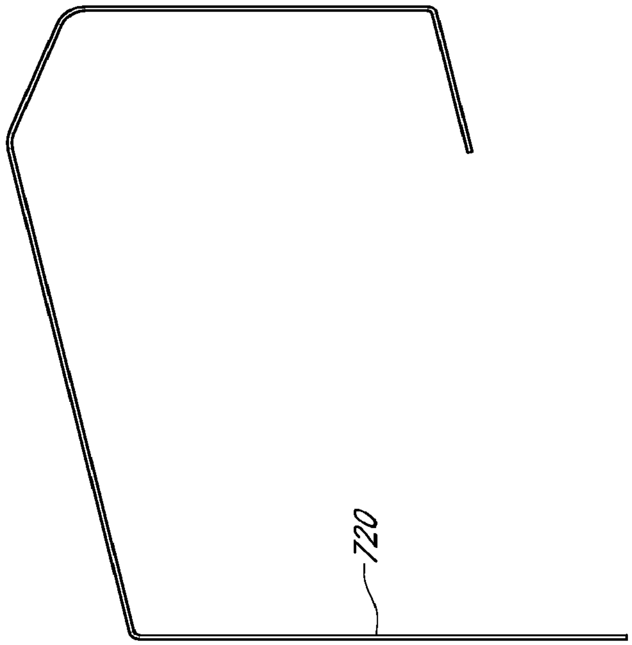
FIG. 25A is a side elevation view of a generally applicable embodiment of a pushrod.
Figure 25B:
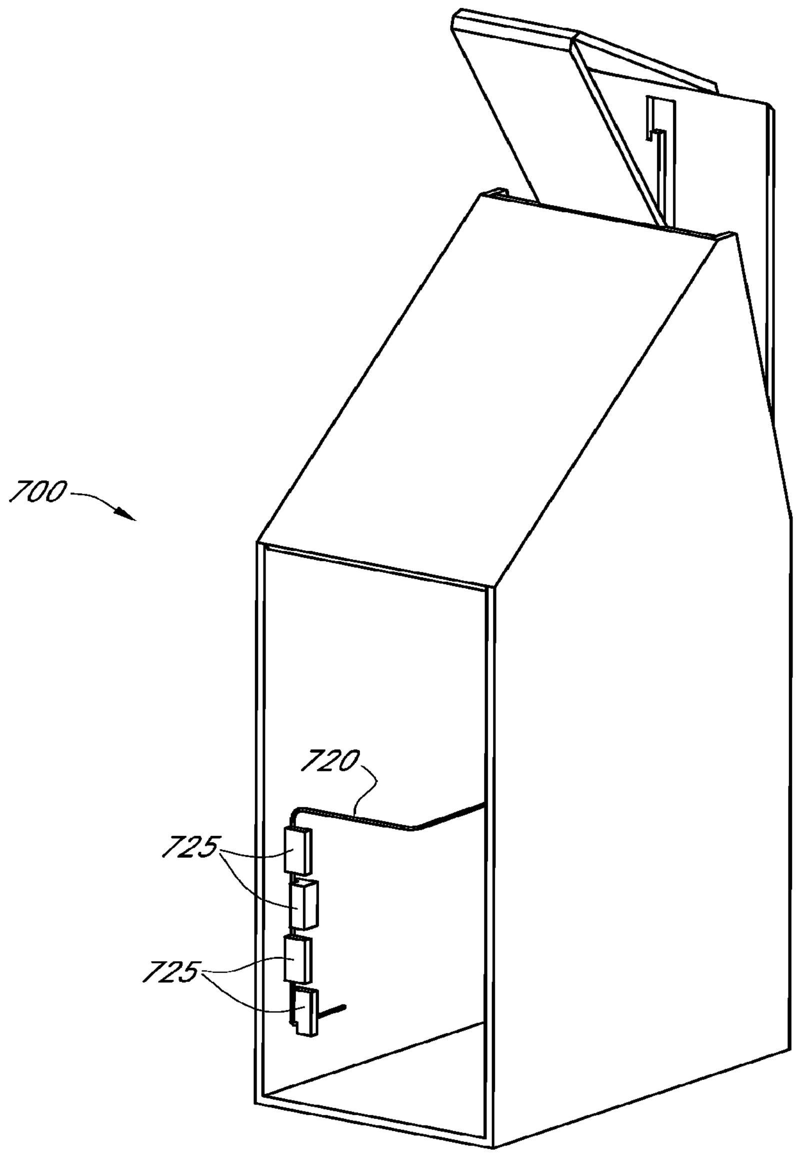
FIG. 25B is a front perspective view showing attachment of the pushrod of FIG. 25A to the mechanism of FIGS. 23A and 23B.

FIGS. 25A and 25B are perspective views showing an embodiment of a pushrod 720 and its attachment to the mechanism 700, which feature is combinable, partly or wholly, with other embodiments described herein. As shown, the pushrod 720 has no bonded carrier and is attached to the mechanism 700 by attachment elements 725 without adhesive. The pushrod 720 is flexible which allows it to stay aligned as it moves to deliver the sensor, even though the back end is attached to the mechanism 700.

Figure 26:
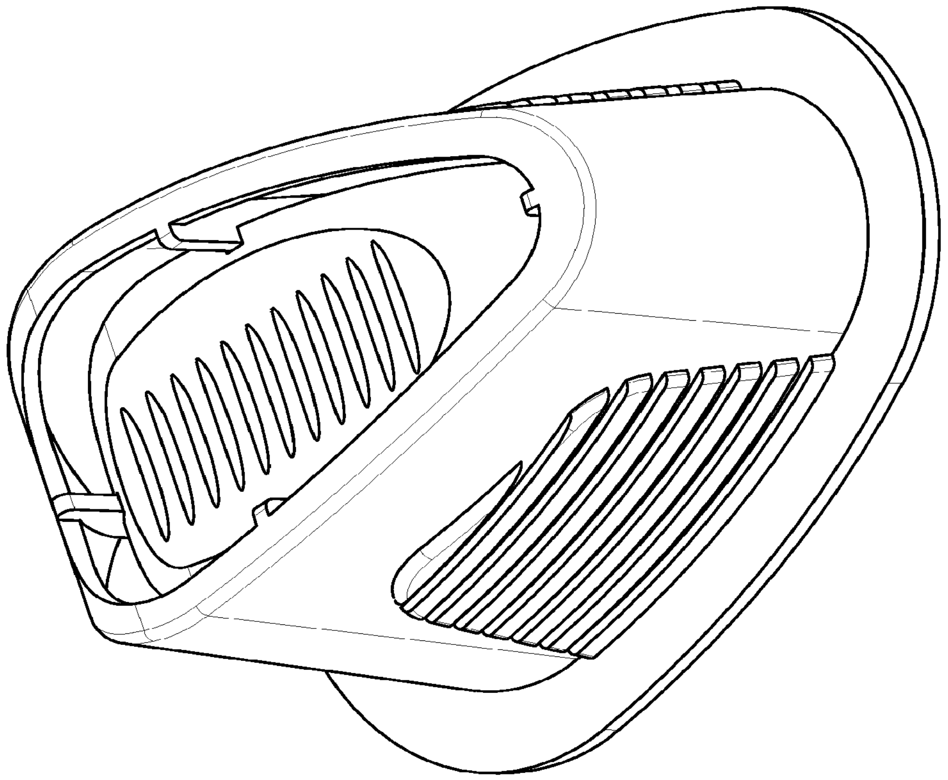
FIG. 26 is a front perspective view showing a generally applicable embodiment of an applicator.

FIG. 26 is a perspective view showing an embodiment of an applicator, which embodiment includes features that are combinable, partly or wholly, with other embodiments described herein. In some embodiments, such as that shown in FIG. 3A6, the applicator may be shaped such that a substantially oval base substantially perpendicularly extends from a substantially vertical substantially oval shaped wall. The wall surrounds a top portion on which the trigger is disposed. In some embodiments, the trigger forms substantially the entire top of the applicator. In some embodiments, the trigger is covered by a removable liner configured to prevent accidental activation of the trigger.

FIGS. 27A-27D are schematic views of the applicator of FIG. 26, illustrating a method of using the applicator. In some embodiments, such as that shown in FIGS. 27A-27D, pressing the trigger 105 causes a needle hub 430 to move so as to insert the sensor 200 into the host. The applicator pod 401 and trigger 405 are indicated in dotted lines. Within the applicator pod 401 a housing 180 with an adhesive 486 is positioned. The adhesive 486 is supported by the rim of the applicator pod 401. The housing 180 is held by ribs provided in the pod (not shown). The support of the rim and the rims allow the full surface area of the adhesive to be firmly pressed onto the host, enabling attachment of the housing 180 without the need to use a second hand or the chance of introducing wrinkles.

The applicator includes a needle 435 that is slidably mounted with a slider 440. The sensor 200 is permanently connected to the electrical contacts 445, e.g., pre-connected at the factory. The slider is slidably mounted in a hinged frame 455 connected to the housing with hinges 456. The top end of the slider 440 engages with the trigger 405 so that when the trigger 405 is depressed, the slider 440 moves downward and the needle hub 430 forces the needle 435 carrying the sensor 200 into the host.

In such embodiments, the needle hub may be connected to a slider which is locked, for example, by a springed latching lock once the sensor has been inserted. Actuation of the lock may provide an audible and/or tactile indication that the sensor is properly inserted.

Figure 27B:
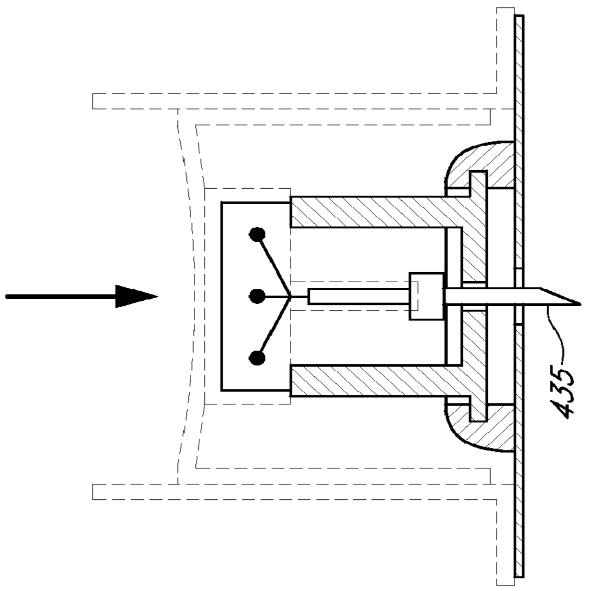
FIGS. 27A-27D are schematic cross-sectional views of the applicator of FIG. 26, illustrating a method of using the applicator to apply a sensor system to a host.
Figure 27A:
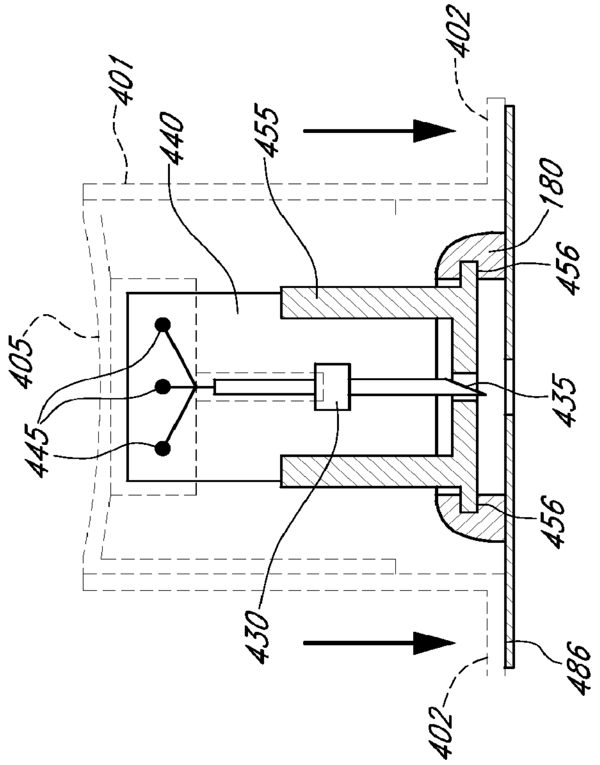

FIG. 27A shows the applicator as attached to the host. As shown, the rim 402 on the applicator pod 401 may be used to exert force on the adhesive while the applicator pod 401 is pressed against the host. FIG. 27B shows the needle 435 inserted into the host. With the depression of the trigger 405, the slider 440 moves down and the needle 435 is inserted into the host. Once the needle 435 has been inserted, a springed latching lock clicks in place, locking the slider 440 and providing an audible and tactile indication that the sensor has been inserted.

Figure 27D:
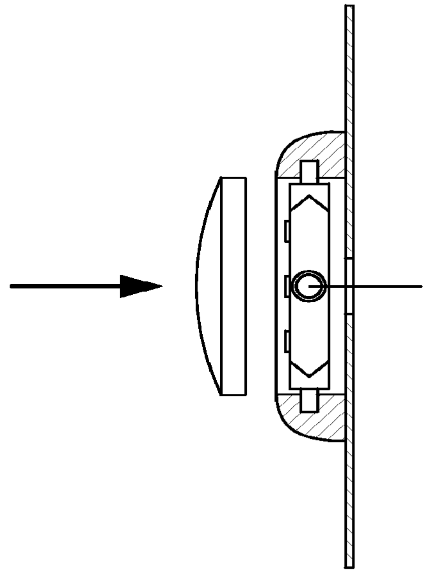
Figure 27C:
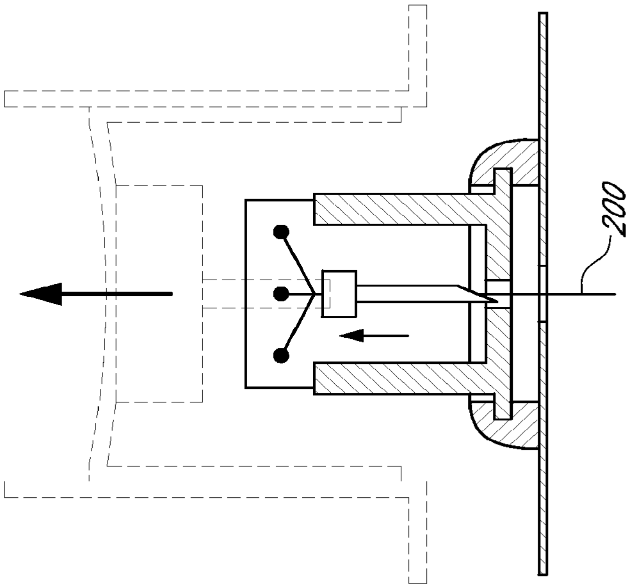

FIG. 27C shows the removal of the applicator pod 401 and the trigger 405. The slider 440 may be releasably engaged with the trigger 405 during depression of the trigger with a latch (not shown). Once the sensor 200 is inserted into the host the latch may be released to release the slider 440 from the trigger 405. Alternatively, the slider 440 may be connected to the trigger 405 by an adhesive. Once the sensor 200 has been inserted, and the springed latching lock has locked the slider, the applicator pod 401 and the trigger 405 are removed such that the trigger adhesive releases, it being weaker than the adhesive attaching the housing 180 to the host. As shown, the slider 440, the needle hub 430, and the needle 435 remain attached with the sensor 200 to the host.

FIG. 27D shows that the slider 440, the needle hub 430, and the needle 435 may fold over so as to have a lower profile. Such folding may be caused by a spring causing the slider 440, the hinged frame 455, the needle hub 430, and the needle 435 to rotate about the hinges 456.

Figure 28A:
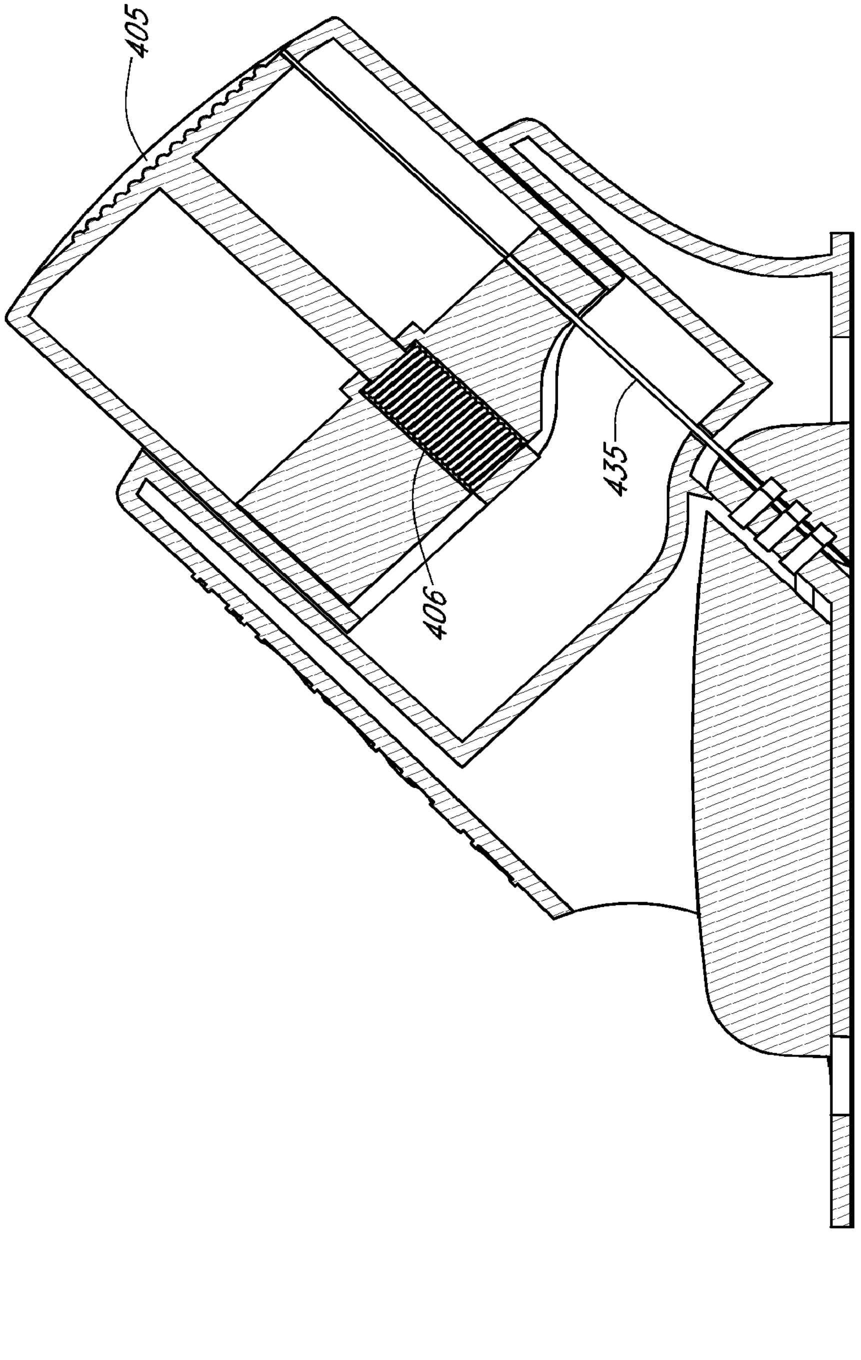
FIGS. 28A and 28B are cross-sectional side views of a generally applicable embodiment of an applicator.
Figure 28B:
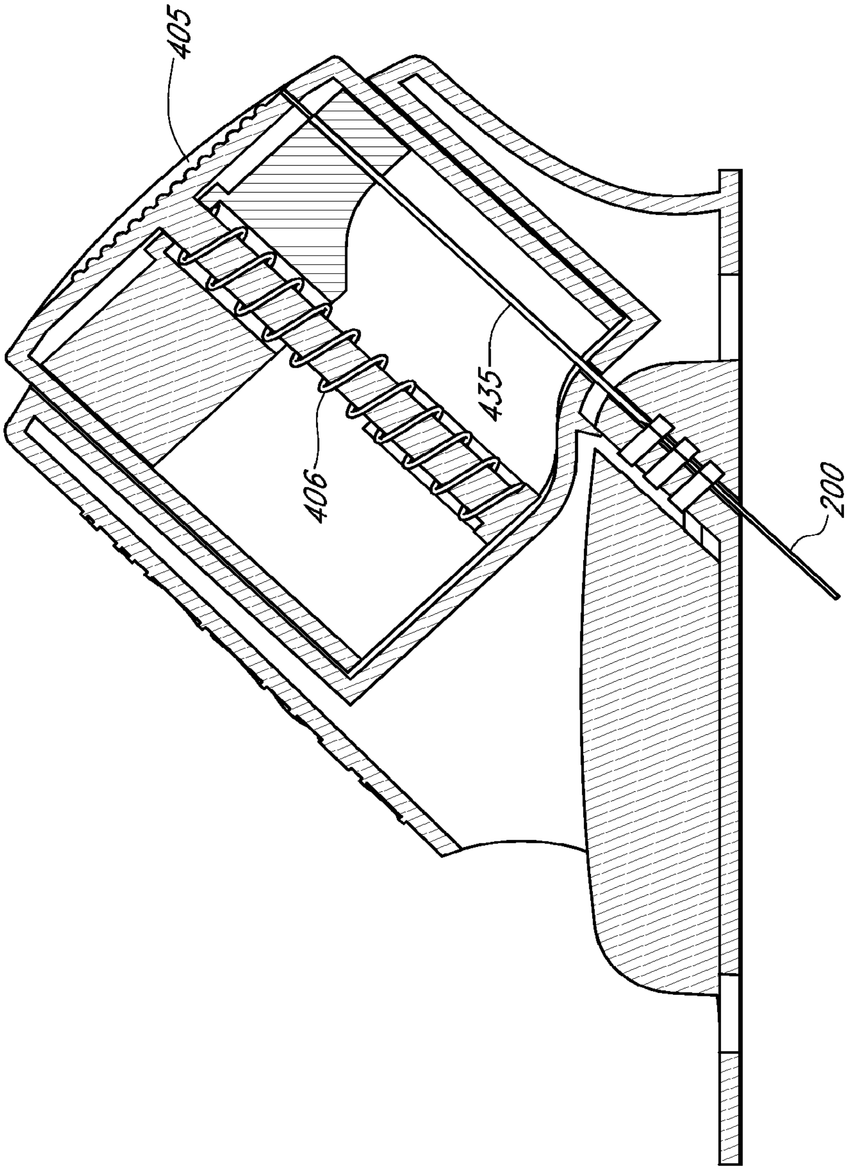

FIGS. 28A and 28B are schematic views of an embodiment of an applicator, which embodiment includes features that are combinable, partly or wholly, with other embodiments described herein. In this embodiment, once the sensor 200 is inserted into the host, a needle spring 406 pushes the needle away from the host after the sensor 200 is inserted into the host.

In some embodiments, the applicator has an exterior formed at least partly of a hard plastic. In some embodiments, an elastomer is used at least partly to relieve strain caused, for example, by movement of the host. The elastomer may be used around the perimeter of the applicator.

Figure 29A:
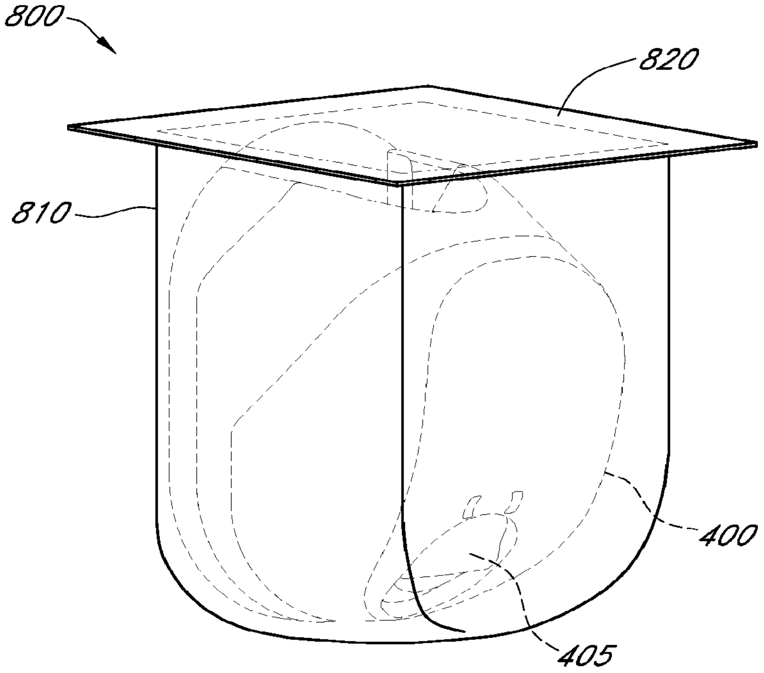
FIGS. 29A and 29B are front perspective views of an applicator in a package and a sensor system for use with the applicator.
Figure 29B:
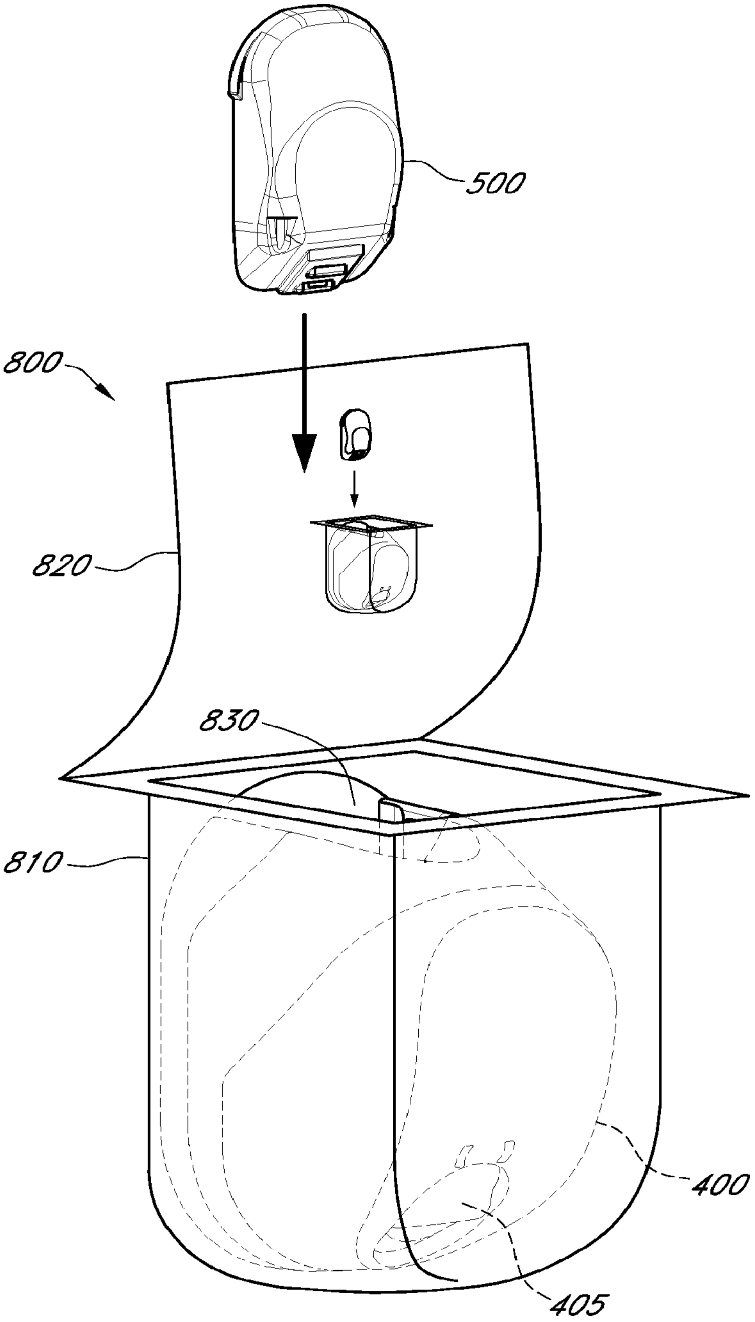
Figure 30A:
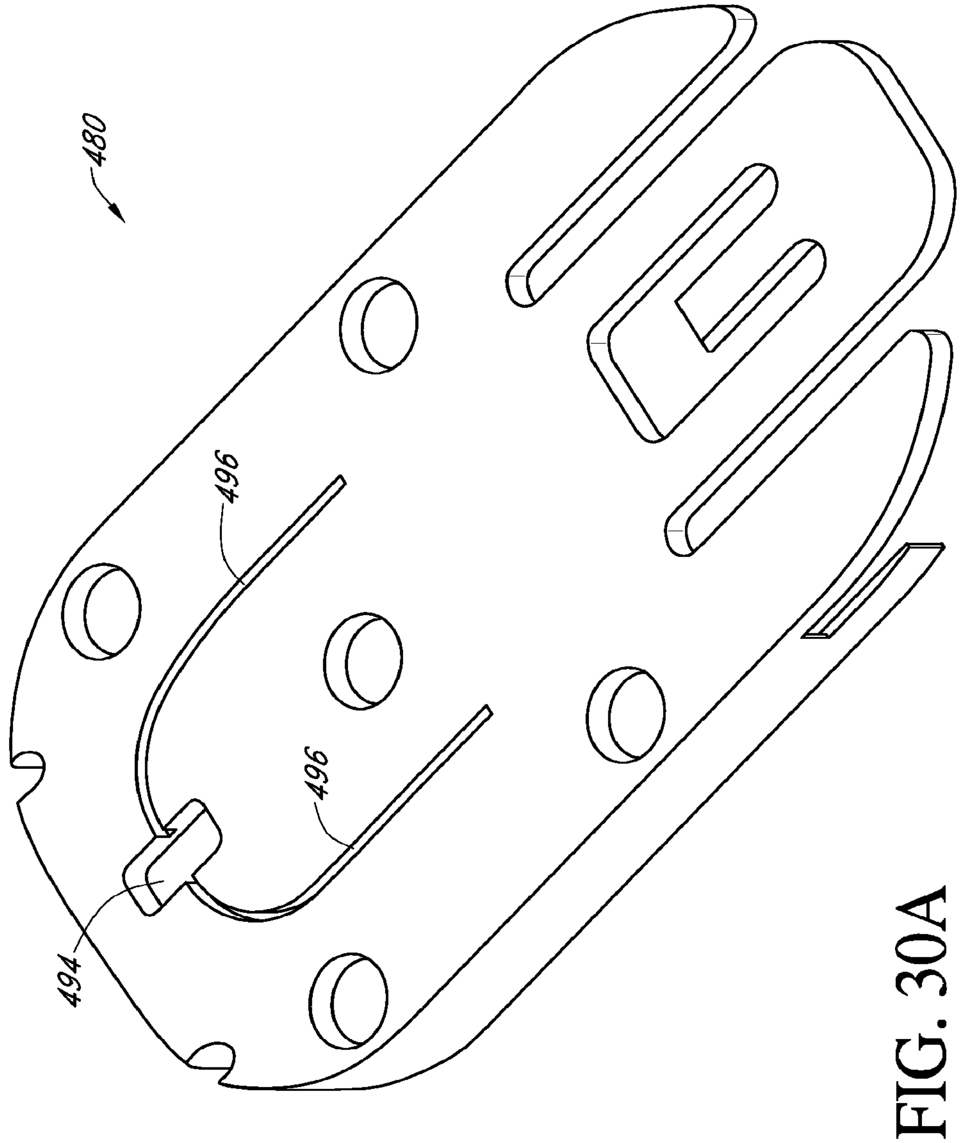
FIGS. 30A-30D are rear perspective views of various generally applicable embodiments of housings having capillary channels.
Figure 30B:
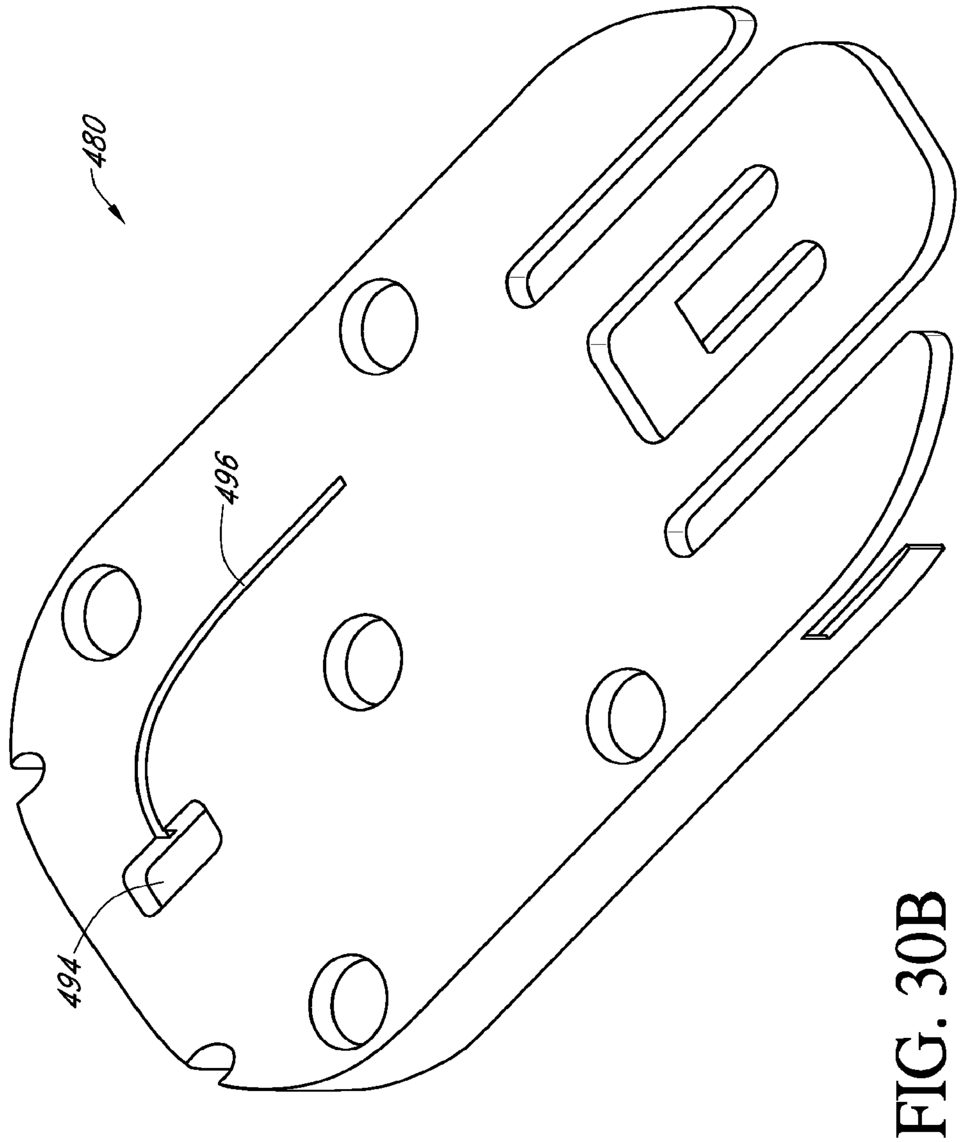
Figure 30C:
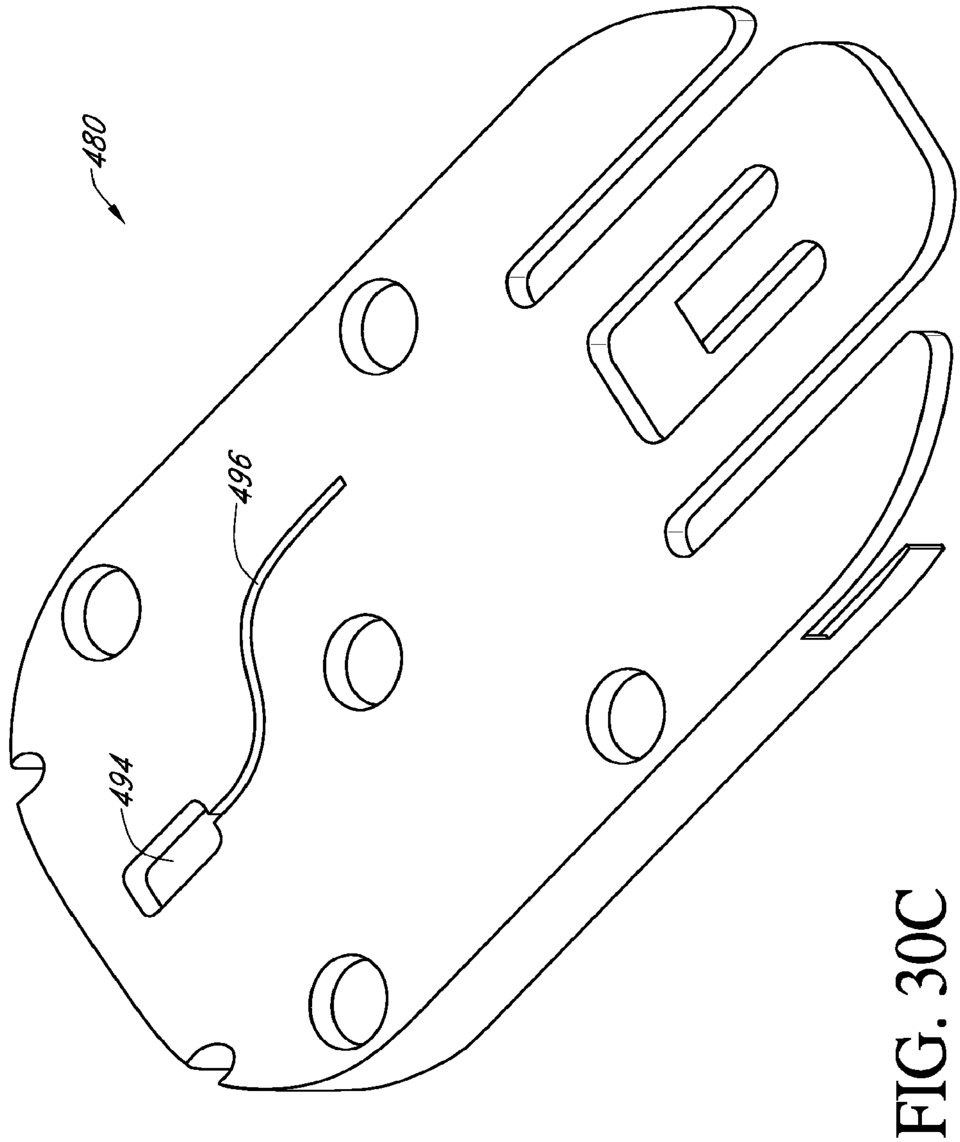
Figure 30D:
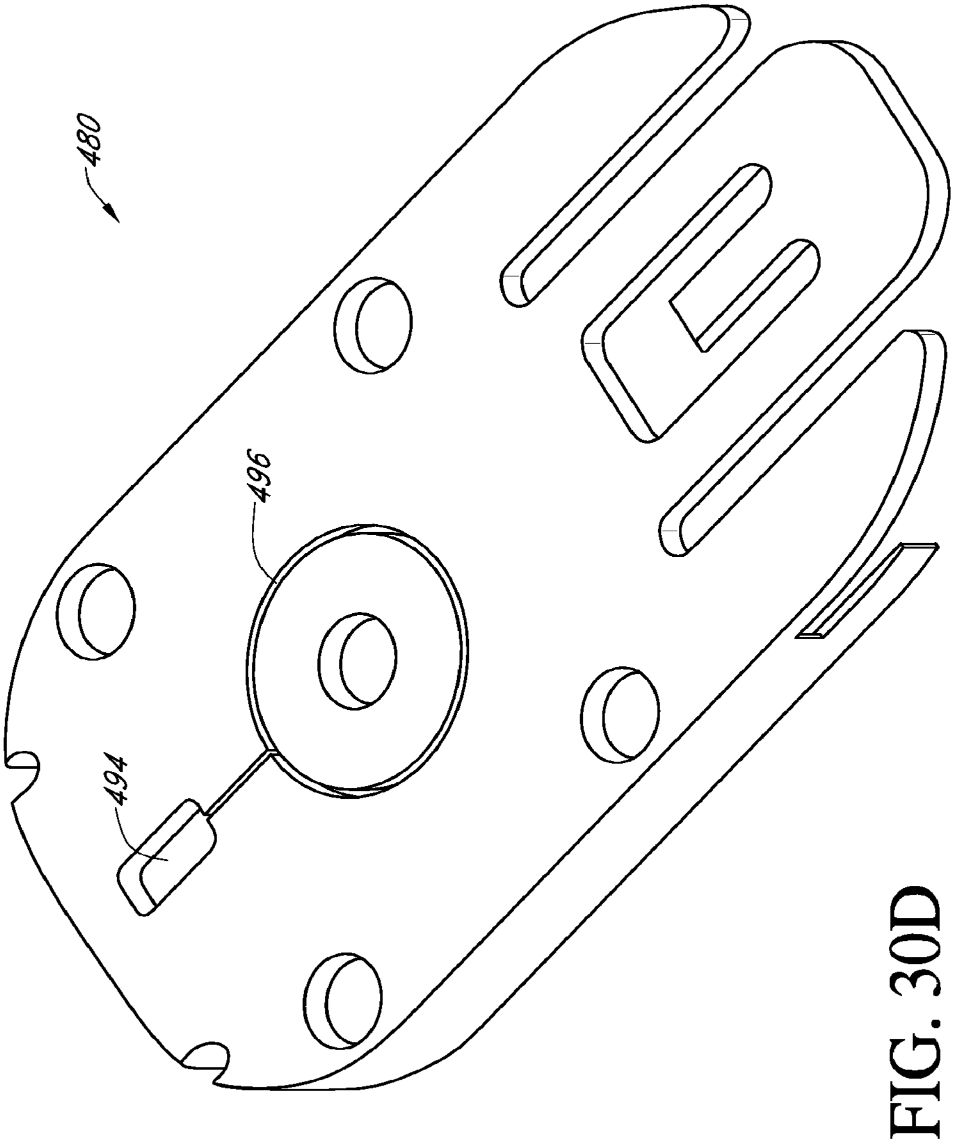

FIGS. 29A and 29B are perspective views of an applicator 400 in a package 800, which is usable with any of the applicator embodiments described herein. In one form, if a user forgets to insert the transmitter 500 before placing the applicator 400, the sensor may be wasted because the applicator cannot be triggered without the transmitter. In addition, handling the applicator with an inserted transmitter can result in undesired activation of the trigger. To remind users to insert the transmitter 500 and to prevent undesired activation of the trigger, package 800 allows for insertion of the transmitter 500 while the applicator 400 is still in the package 800.

In some embodiments, the package 800 includes a shell 810 in which the applicator 400 is held in a fixed position. In some embodiments, the shell 810 is vacuum formed. The shell 810 is sealed with a removable tab 820, which may be peeled off of the shell 810 to expose the applicator 400. The applicator 400 is oriented in the package 800 so that a cavity 830 into which the transmitter 500 is to be inserted is accessible once the tab 820 is removed. The exposed cavity 830 provides a visual cue or reminder to the user that the transmitter 500 should be inserted into the applicator 400. In some embodiments, a portion of the tab 820 which is exposed by its removal may have information, such as graphics, thereon which provides instructions or a reminder to insert the transmitter 500 into the cavity 830.

In some embodiments, the shell 810 is rigid, so that the shell 810 shields the trigger 405 to substantially prevent access to the trigger 405 while the applicator 400 is still in the shell 810. Accordingly, undesired activation of the trigger is substantially prevented.

In some embodiments, the housing 480 has one or more openings around their perimeter and/or side surfaces so that moisture which enters the applicator 400, can quickly be removed. In some embodiments, the housing includes a wicking material which wicks moisture to the perimeter openings. For example, the adhesive patch 485 may include a wicking material, such as a woven or a non-woven wicking material. In some embodiments, the housing 480 has a channel formed therein which draws moisture from within the applicator 400 toward the outside. In some embodiments, all or substantially all water is removed from the applicator 400 within about 15-30 minutes.

When the sensor 200 is inserted into the host, blood may be released by the host. In some embodiments, the blood is collected in a blood reservoir, for example, in the housing 480. The blood may be transmitted to the reservoir through a weep hole in the housing by a capillary channel or wicking material. In the reservoir, the blood may be absorbed, for example, by a sponge, a super absorbent polymer, a wicking material. In some embodiments, the reservoir and/or the insertion site on the host are aerated to, for example, allow for drying and to reduce bacterial growth.

FIGS. 30A-30D are illustrations of generally applicable embodiments of housing 480 showing the host side of the housing 480, which embodiments are combinable, partly or wholly, with other embodiments described herein. The housing 480 has hole 494 through which the needle 435 passes, and one or more capillary channels 496, configured to wick, for example, blood away from the hole 494 and away from the perimeter of the housing 480.

In some embodiments, the applicator base 465 and/or the patch 485 has a barrier to prevent blood from wicking from underneath the applicator 400. The barrier may, for example, comprise a silicon rib or a glue seal. The barrier may be placed, for example, across a portion of the applicator perimeter, for example, near the needle 435. Additionally or alternatively, a barrier may be placed around the needle 435, for example, around and near the hole in the patch 485 through which the needle passes.

910 to detect that the applicator 400 has been placed on the host, which embodiments combinable, partly or wholly, with other embodiments described herein. The sensors are in electrical communication with a safety mechanism 920, which prevents the trigger 405 from being activated unless the applicator 400 has been placed on the host. In these embodiments, the sensors 910 and the safety mechanism 920 form, in part, an electrical circuit. The circuit is completed if the sensors contact the skin of the host. With the circuit open, the safety mechanism 920 prevents the trigger 405 from being activated. Once the circuit is closed in response to the sensors 910 contacting the skin of the host, the safety mechanism 920 allows the trigger 405 to be activated as discussed above. In some embodiments, the safety mechanism 920 includes a battery. In some embodiments, a battery is included in the circuit as a component separate from the safety mechanism 920.

Figure 31A:
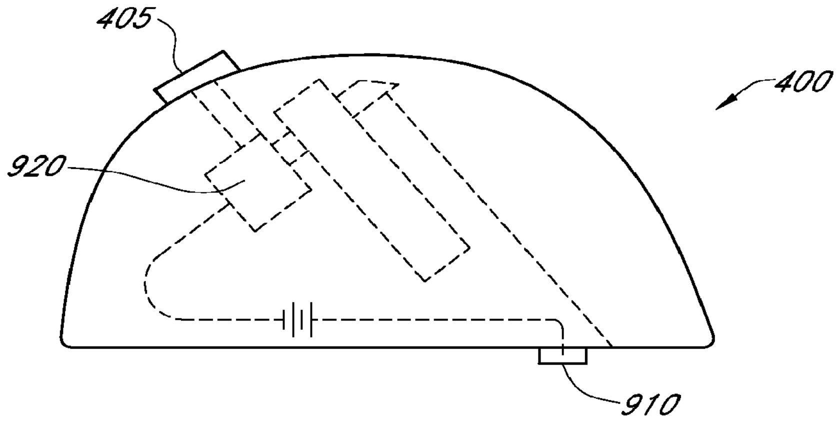
FIG. 31A is a side elevation view of a generally applicable embodiment of an applicator having sensors to detect that the applicator has been placed on the host.
Figure 31B:
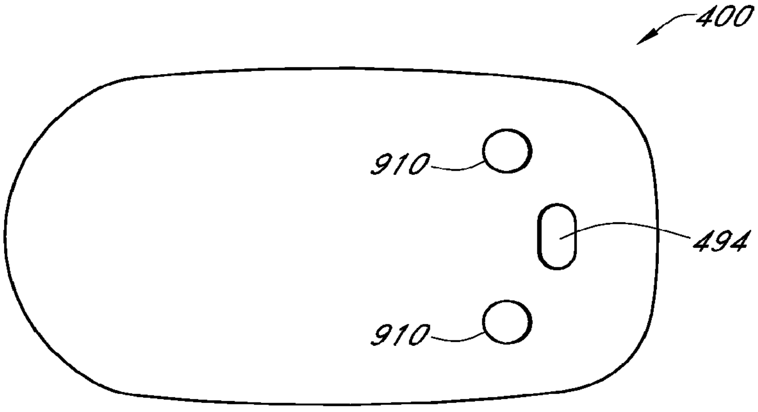
FIG. 31B is a bottom plan view of the applicator of FIG. 31A.
Figure 31C:
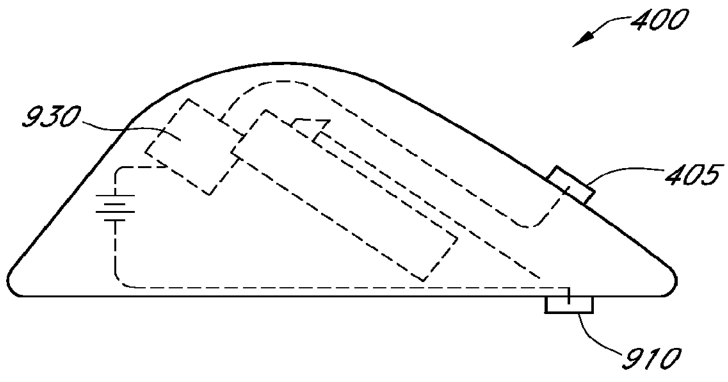
FIG. 31C is a side elevation view of a generally applicable embodiment of an applicator having sensors to detect that the applicator has been placed on the host.
Figure 31D:
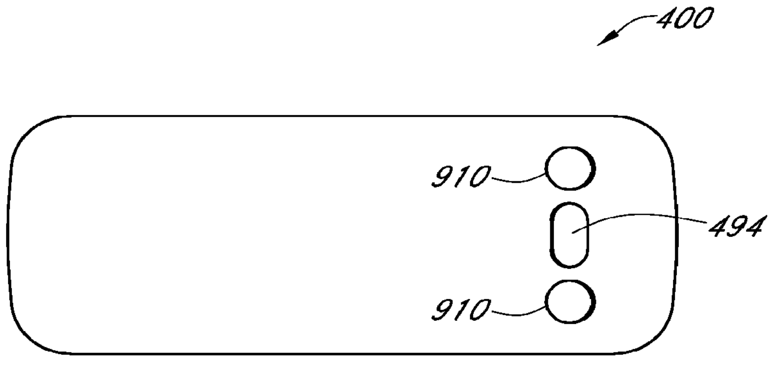
FIG. 31D is a bottom plan view of the applicator of FIG. 31C.

In some embodiments, such as the embodiments shown in FIGS. 31C and 31D, the trigger 405 is electronic. For example, the trigger 405, when activated, provides a signal to an electric actuator 930. In response to the signal the electric actuator 930 causes the applicator 400 to insert the sensor into the host, to seat the transmitter 500 into the housing, and to detach the applicator 400 from the on-skin sensor assembly 600, as discussed above. In such embodiments, the signal may be provided to the electric actuator 930 only if the sensors contact the skin of the host. In some embodiments, the electronic trigger 405 is an electric switch. In such embodiments, the switch, the electric actuator 930, the battery, and the sensors 920 are part of the same circuit. Accordingly, in order to actuate the applicator 400 of such embodiments, the sensors 920 must be on the skin of the host when the switch of the electronic trigger 405 is closed.

FIGS. 32-50 illustrate generally applicable features, which features are combinable, partly or wholly, with other embodiments described herein. For example, as technology enables sensor life spans to be increased, there may be a need for long-term securement of the transmitter sensor combination to the skin 3206 of the user. One challenge is that current adhesive materials generally release from the skin 3206 at about 5-7 days. To provide a way for long-term adhesion, FIGS. 32-35 illustrate an example of a multilayer in-situ renewable adhesive patch 3200.

Figure 32:
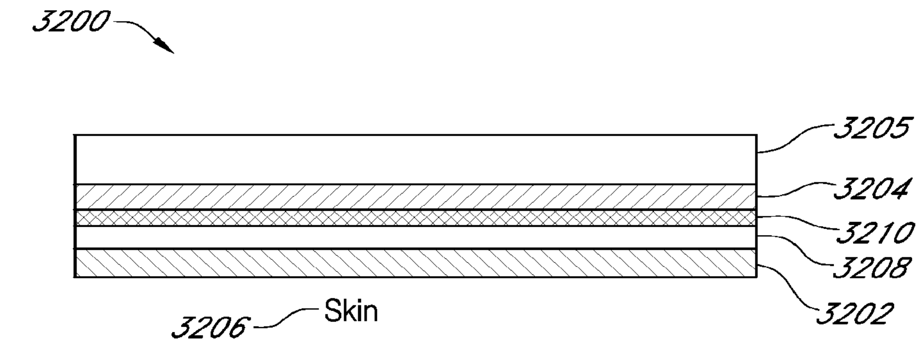
FIGS. 32-35 are schematic views of an in-situ renewable adhesive patch, according to a generally applicable embodiment.

FIG. 32 shows a cross-section of the multilayer patch 3200. A first adhesive layer 3202 and a second adhesive layer 3204 are provided. The sensor base (not shown) will be affixed to a backing layer 3205 of the patch 3200 opposite the skin 3206. After removal of a liner (not shown) the patch 3200 is adhered to the skin 3206 with the first adhesive layer 3202. Between the first and second adhesive layers 3202, 3204 is a backing layer 3208 for providing some mechanical rigidity to the first adhesive layer 3202.

Figure 33:
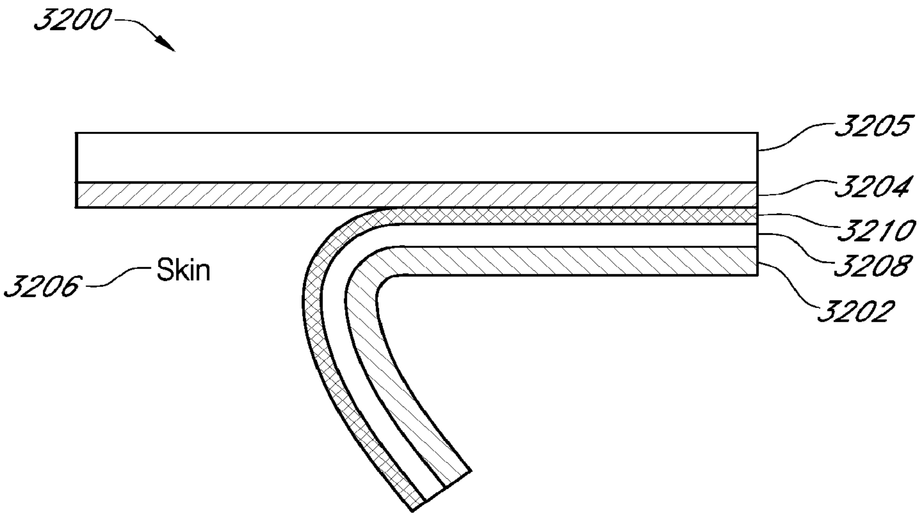

On top of backing layer 3208 is a low-stick coating 3210, which may be silicone for example. This low-stick coating 3210 allows the removal of the first adhesive layer 3202 while the device is kept in place. For instance, after a given number of days, the first adhesive layer 3202 may start to loosen from the skin 3206. The user can then peel off the bottom layer comprising the first adhesive layer 3202, the backing layer 3208, and the low-stick coating 3210, as shown in FIG. 33. While removing this layer from the skin 3206, the second adhesive layer 3204 is exposed and subsequently adhered to the skin 3206, allowing the device to be worn for additional days. Preferably, the low-stick coating 3210 provides enough tack to keep the layers together during the first phase of use, such as 5-7 days, while it still allowing the peeling off of the first adhesive layer 3202. For example, silicone coatings that are used in peel-off liners may provide satisfactory results.

Figure 34:
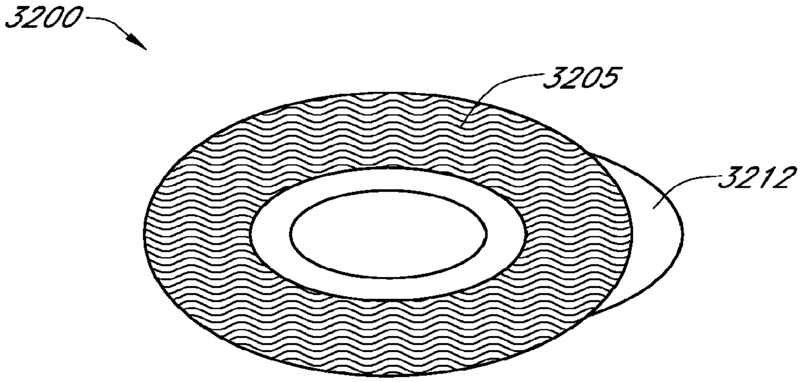
Figure 35:
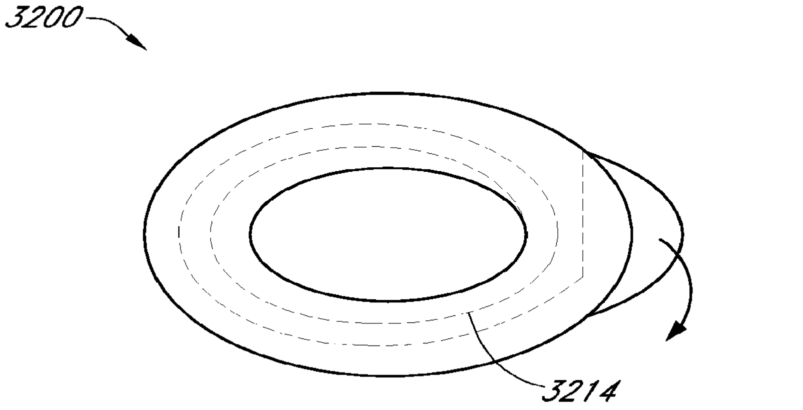

FIGS. 34 and 35 are top and bottom views, respectively, of the patch 3200. FIG. 34 shows the backing layer 3205 on top of which the transmitter (not shown) is attached, while FIG. 35 shows the first adhesive layer 3202. With reference to FIG. 34, on one side a peel-off tab 3212 is provided. The tab 3212 is used to initiate peeling off the first adhesive layer 3202. To ease peel-off, a so called 'kiss-cut' is made through the first adhesive layer 3202 and its low-stick coated backing. For example, with reference to FIG. 35, a circle or spiral cut 3214 can be formed so that the first layer can be removed in a defined, circling manner.

The foregoing embodiment advantageously provides an adhesive patch that supports long term sensor wear, and that can be deployed in-situ (i.e. without removal of the sensor).

Sensor Electronics Encapsulation

In some generally applicable embodiments, which embodiments are combinable, partly or wholly, with other embodiments described herein the transmitter may be encapsulated within a molded body, for example, a thermoset, plastic, polymer, glass, ceramic, or other such material. In some embodiments, the encapsulating body may additionally or alternatively be machined or casted. Bodies formed using other methods may also be used.

In some embodiments, the resistance to water penetration around the contacts may be designed to a standard. For example, the transmitter may be designed to meet the IPX-8 Standard 6.6.1, which mandates that the device be protected against continuous water immersion beyond 1 m, with the depth of immersion to be specified by the manufacturer. The IPX-8 Standard is incorporated herein by reference in its entirety. However, other standards may be used instead.

Figure 42:
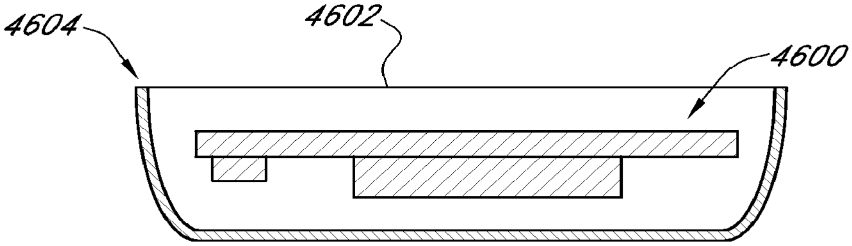
FIGS. 42-44 are schematic views of a process for making a seamless cleanable transmitter, according to a generally applicable embodiment.
Figure 43:
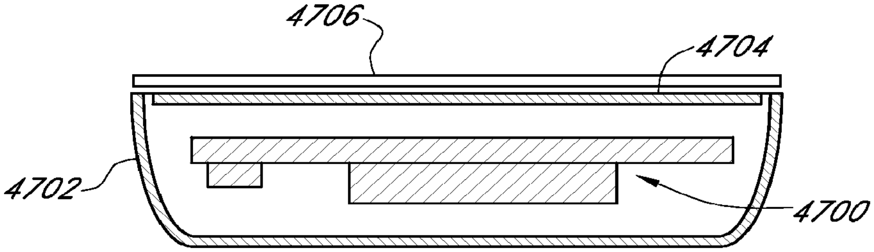
Figure 44:
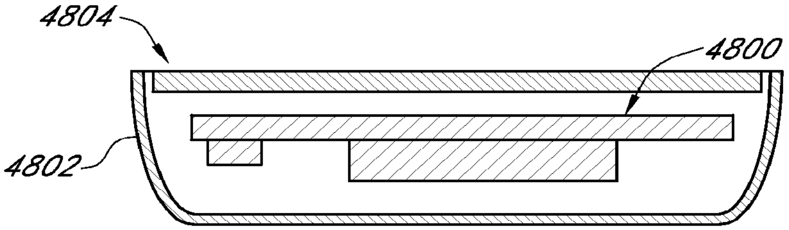

The transmitter is worn on the host's body near the needle insertion site. Thus, it is preferably easy to clean—especially if it is to be used by multiple patients. The present transmitter includes electronics potted within a plastic shell. Three potentially challenging areas to clean are interior corners and crevices, seams around the lower edge (at the opening) of the plastic shell, and around the electrical contacts. FIGS. 42-44 illustrate generally applicable embodiments that provide solutions for each of these challenging areas. Advantageously, the embodiments described herein are usable for multiple patients and pass worst case scenario testing for cleaning between uses, for example, when the transmitter is dunked in a solution of bleach for about 5 minutes, after which the transmitter is tested for cleanliness using standards known to one skilled in the art.

With regard to the first potential challenge above, i.e. small crevices, these are difficult to clean, so if every interior corner is designed with at least a minimum radius, it would ensure that a cleaning instrument could access it, which is generally applicable, particularly with any other embodiment described herein. For example, a typical toothbrush bristle is about 0.007" in diameter, so if a device was designed with every interior corner radiused greater than 0.0035," it would be cleanable with a toothbrush (or similar cleaning brush). And in other embodiments an even larger minimum diameter such as 0.010" or 0.020" may be provided.

With regard to the second potential challenge above, i.e. seams around the lower edge (at the opening) of the plastic shell, one example solution provides a shell with self-leveling epoxy surface, which is generally applicable, particularly with any other embodiment described herein. With reference to FIG. 42, the transmitter electronic assembly 4600 is potted with an encapsulant 4602 such as epoxy, within a plastic shell 4604. The encapsulant 4602 is filled to the top of the shell 4604 where it cures and bonds to the shell 4604. It forms a seamless interface between the plastic of the shell 4604 and the material of the encapsulant 4602. Other types of encapsulants may be used as well, such as urethane or silicone.

Again with regard to the second potential challenge above, the shell may have a machined encapsulant surface, substantially the same as FIG. 42, but the encapsulant surface is machined down to a desired height for a more accurate surface flatness and height, which is generally applicable, particularly with any other embodiment described herein. Alternatively, the shell may have a molded encapsulant surface, substantially the same as FIG. 42, but using a mold, such as a silicone mold, to define the encapsulant surface rather than letting the encapsulant self-level.

Again with regard to the second potential challenge above, the shell may have a lid with a top coating, which is generally applicable, particularly with any other embodiment described herein. With reference to FIG. 43, the transmitter electronic assembly 4700 is potted inside a shell 4702 having a lid 4704. A coating 4706, which may be an encapsulant, covers the seam between the shell and the lid. The coating may be applied on the entire surface of the seam, or just applied along the seam line. The coating advantageously covers up crevices where bacteria could hide, making the device easier to clean.

Again with regard to the second potential challenge above, the shell may have a bonded lid, which is generally applicable, particularly with any other embodiment described herein. Again, the transmitter electronic assembly is fitted inside a shell and lid where the shell is bonded to the lid using ultrasonic welding or laser welding. If potting is used, potting material may be pre-filled leaving room for the lid. Another method is to first bond the lid and use inlet and outlet ports to fill the potting material. Materials at the inlet and outlet ports are then cut flush to lid. Alternatively, the shell may have an over-molded lid. Again, with reference to FIG. 44, the transmitter electronic assembly 4800 is fitted inside a shell 4802 and potted just enough to cover the electronics. Then the lid 4804 is formed by over-molding with a plastic material. A low-pressure or high-pressure molding technique can be used.

Again with regard to the second potential challenge above, the transmitter may be made by using an insert molding process using high or low pressure molding techniques or liquid injection molding techniques, which is generally applicable, particularly with any other embodiment described herein. The transmitter electronics would be placed inside a mold and then surrounded with a polymer. The batteries would need to be protected from the heat spike that would occur in this embodiment, so the mold and process parameters could be tailored so that the heat spike is tolerated by the battery. Alternatively, the transmitter may also be made by completely encapsulating it within an encapsulant. For example, the electronic assembly could be suspended in a silicone mold, and once cured the suspension features would be cut off. If needed the top surface may be machined to form desired features.

With regard to the third potential challenge above, i.e. the electrical contacts, the transmitter exterior is typically an insulator, and electrical connection must be made from the sensor outside the transmitter to the electronics inside, which is generally applicable, particularly with any other embodiment described herein. Typically this involves installing electrical contacts through holes in the transmitter, but this creates a seam with a small gap around the edges of the contacts that is difficult to clean. This gap could be filled with glue or other material, but this is a challenge to control and is costly.

In one embodiment of a solution to this problem, if conductive polymer contacts, such as a polymer filled with carbon particles, are over-molded directly in place into holes in the shell, the over-molding process will slightly re-melt the shell material, causing the contact and shell materials to weld together, thereby forming a hermetic seal, which is generally applicable, particularly with any other embodiment described herein. In this way, electrical contact can be made through the shell and leave a smooth seam with no crevice to present a cleaning challenge.

The foregoing embodiments provide advantages, including at least no seams or crevices to accumulate bodily fluids or debris, ease of cleaning, and waterproofing/water resistance.

Figure 45:
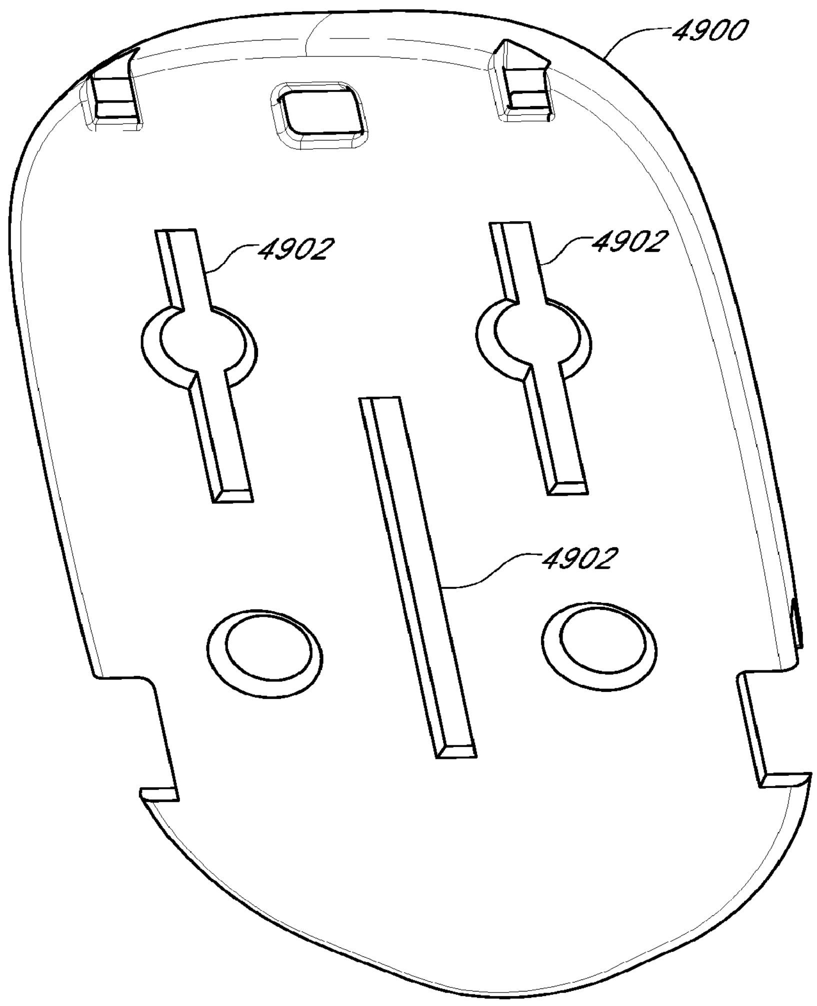
FIG. 45 is a lower perspective view of a housing, according to a generally applicable embodiment.

With reference to FIG. 45, in a generally applicable embodiment of the housing 4900 including slots 4902 in a bottom thereof. The slots provide a mechanism for emergency transmitter removal from a jammed applicator, so that the user can salvage the transmitter and try again with a new applicator. After the applicator is removed from the host's skin, a paperclip inserted through the slots can be used to pull the transmitter back out of the applicator. In certain embodiments, the slots are cut through the adhesive patch as well to increase the ease of access to the transmitter.

Figure 46:
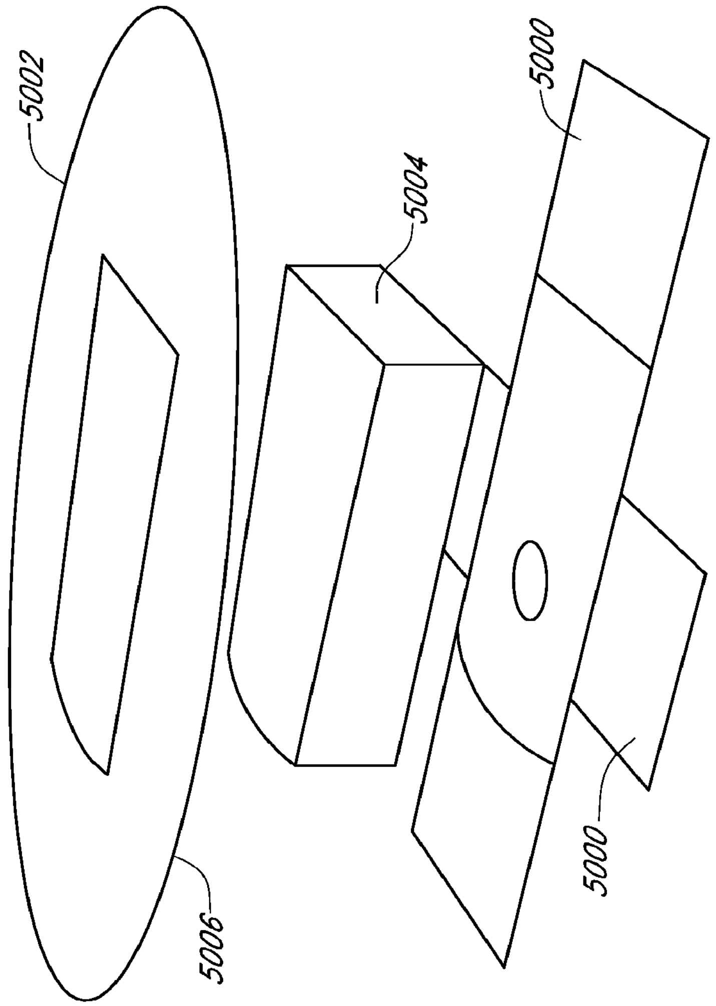
FIG. 46 is a schematic view of a sensor pod adhesive design, according to a generally applicable embodiment.
Figure 47:
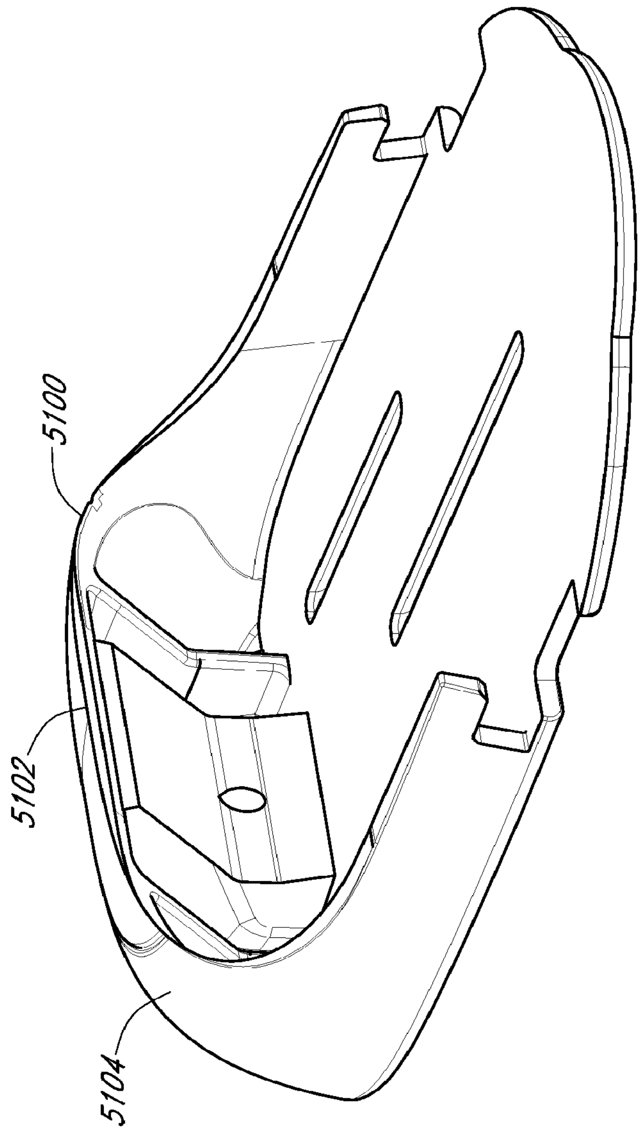
FIG. 47 is a rear perspective view of a housing, according to a generally applicable embodiment.

With reference to FIG. 46, in a generally applicable embodiment butterfly stitches 5000 (also referred to as "strips") are incorporated into (and under) the adhesive patch 5002, which embodiment is combinable, partly or wholly, with other embodiments described herein. In the illustrated embodiment, two strips are provided in a perpendicular crossing pattern ("X" shape), but in other embodiments any number of strips may be provided in any configuration. The surfaces of the strips in contact with the sticky surface of the adhesive patch are only lightly tacky. The strips are preferably sufficiently narrow to minimize interruption with the primary adhesive patch, yet provide adequate security for the user to replace a failing adhesive patch without accidental removal of the on-skin sensor assembly 5004. The existing patch is removed by peeling patch at a perforated line 5006 at a corner of the patch. A new adhesive patch with a donut shape is applied to skin over the butterfly stitches for continued use of the CGM. This embodiment provides avoidance of re-puncturing the skin with a new sensor, mitigation of existing user nuisance (adhesive failure), uninterrupted use of the CGM, and may reduce ingress of foreign matter/fluid FIG. 47 is a rear perspective view of a housing 5100, according to a generally applicable embodiment, which embodiment is combinable, partly or wholly, with other embodiments described herein. As with previous embodiments, the housing includes a seal 5102 at a front end thereof and abutting an inner surface. The seal, which will abut the transmitter and hold the sensor when the sensor is implanted, may be constructed of an elastomeric or conformable material. In one embodiment of a method for making the housing, the seal is overmolded with the thermoplastic portions 5104 of the housing.

Figure 48:
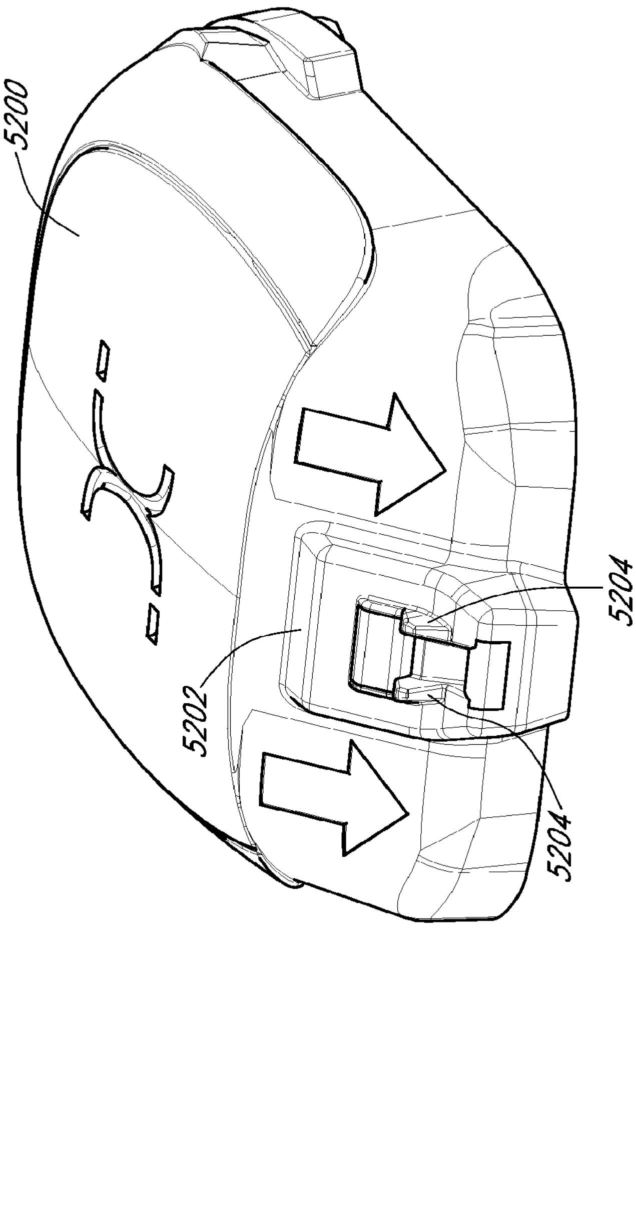
FIGS. 48-51 are various perspective and elevation views of a transmitter, according to a generally applicable embodiment.
Figure 49:
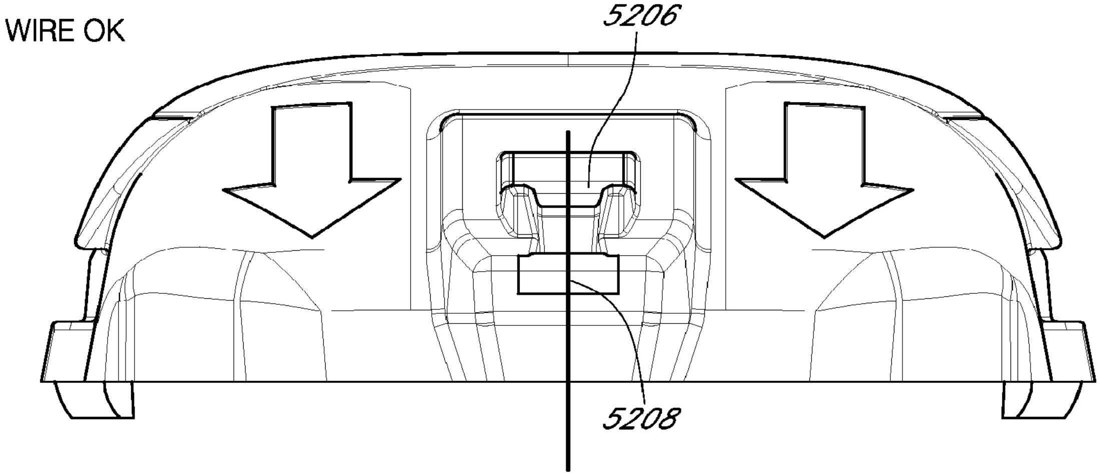
Figure 50:
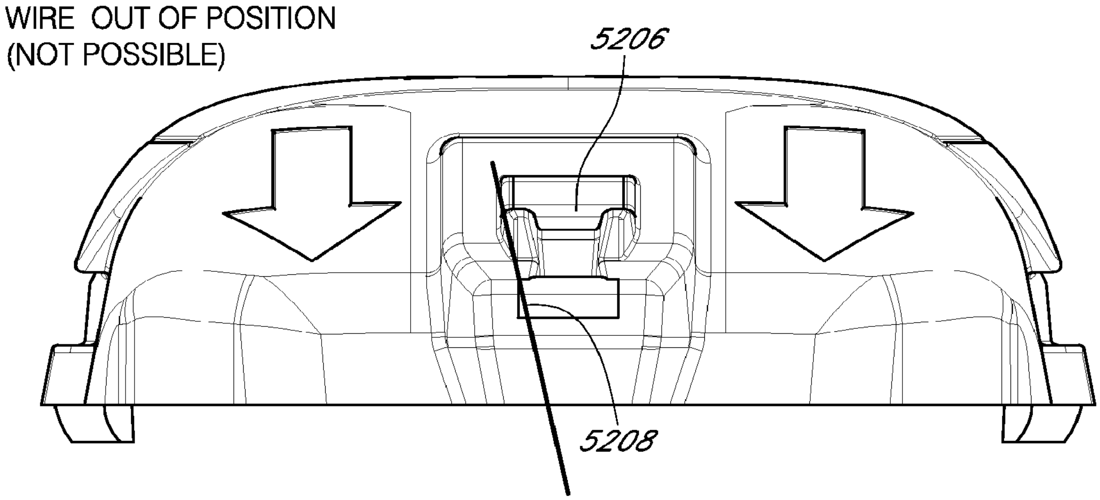
Figure 51:
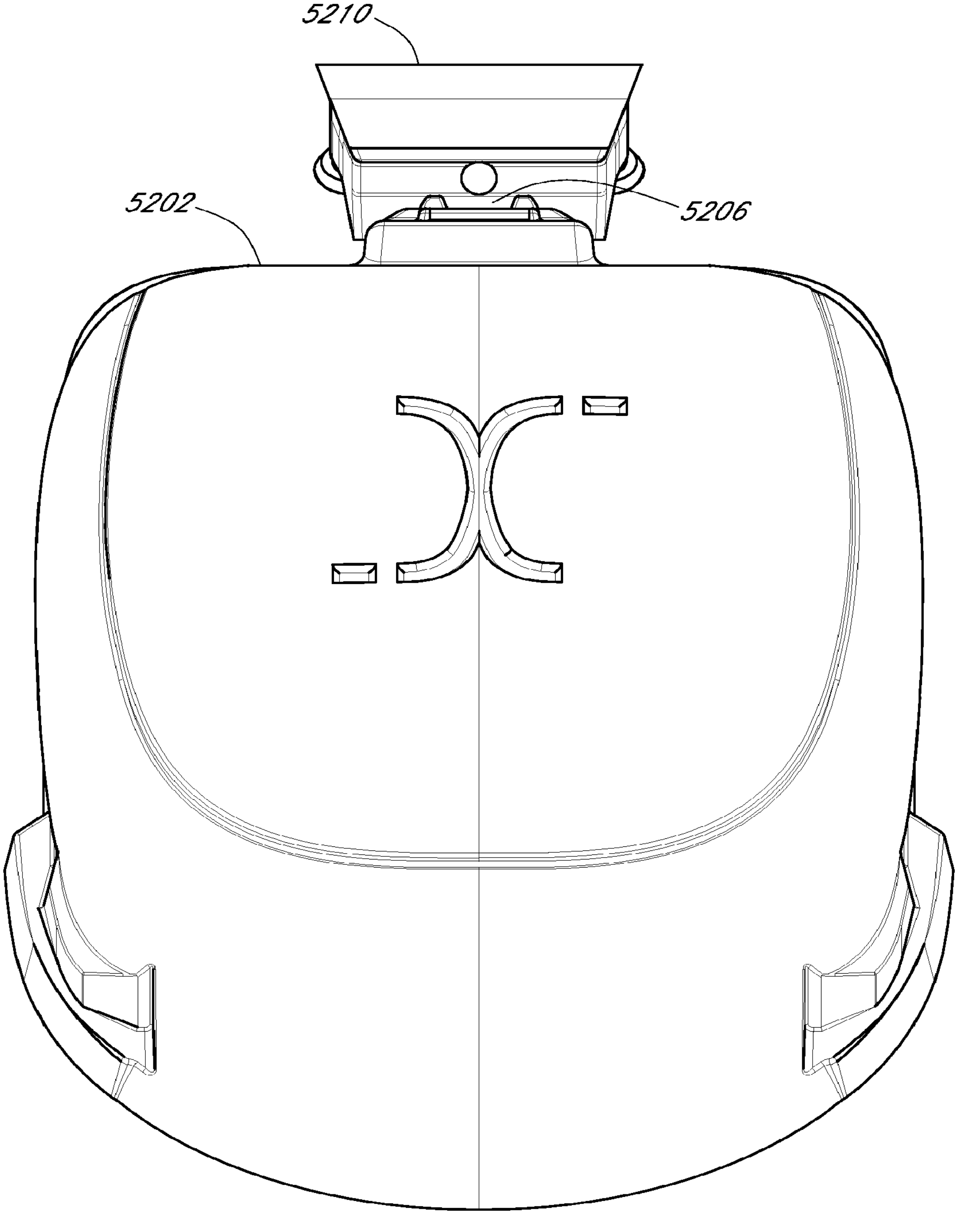

FIGS. 48-51 are various perspective and elevation views of a transmitter 5200, according to a generally applicable embodiment, which embodiment is combinable, partly or wholly, with other embodiments described herein. With reference to FIG. 48, the seal 5202 at the front end of the transmitter includes first and second spaced protrusions 5204. A space between the protrusions receives the sensor when it is implanted. With reference to FIGS. 49-51, that space creates a protected area 5206 that traps the sensor 5208 during the process of compressing the seal against the housing 5210 (FIG. 51) in order to prevent misalignment of the sensor (which is illustrated in FIG. 50).

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Further, any combination of devices or systems may be used to implement the present methods and processes.

Methods and devices that are suitable for use in conjunction with aspects of the preferred embodiments are disclosed in U.S. Pat. No. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976-A1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S.

Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; U.S. Patent Publication No. 2005-0182451-A1; U.S. Patent Publication No. 2013000536650A1; and U.S. Patent Publication No. 2013-0053666-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "SENSORS FOR CONTINUOUS ANALYTE MONITORING, AND RELATED METHODS"; U.S. application Ser. No. 13/784,523 filed on Mar. 4, 2013 and entitled "ANALYTE SENSOR WITH INCREASED REFERENCE CAPACITY"; U.S. application Ser. No. 13/789,371 filed on Mar. 7, 2013 and entitled "MULTIPLE ELECTRODE SYSTEM FOR A CONTINUOUS ANALYTE SENSOR, AND RELATED METHODS"; U.S. application Ser. No. 13/789,279 filed on Mar. 7, 2013 and entitled "USE OF SENSOR REDUNDANCY TO DETECT SENSOR FAILURES"; U.S. application Ser. No. 13/789,339 filed on Mar. 7, 2013 and entitled "DYNAMIC REPORT BUILDING"; U.S. application Ser. No. 13/789,341 filed on Mar. 7, 2013 and entitled "REPORTING MODULES"; and U.S. application Ser. No. 13/790,281 filed on Mar. 8, 2013 and entitled "SYSTEMS AND METHODS FOR MANAGING GLYCEMIC VARIABILITY".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A device for applying an on-skin sensor assembly to skin of a host, the device comprising:

a housing configured to receive an electronics unit, wherein the housing includes an insertion hole, wherein the electronics unit is configured to generate analyte information based on a signal from a sensor, wherein the electronics unit includes conductive polymer contacts to electrically connect the electronics unit to the sensor, wherein the electrical connection between the electronics unit and the sensor is formed at a factory;

a sensor insertion mechanism including a needle configured to insert the sensor into the host; and wherein the housing includes one or more capillary channels, the one or more capillary channels configured to wick blood away from the insertion hole, wherein the one or more capillary channels includes a first channel and a second channel, the first channel is a linear channel, the second channel is an annular ring channel, wherein the first end channel is in fluidic communication with the insertion hole and with the second channel.

2. The device of claim 1, wherein the housing is configured such that the electronics unit cannot be removed from the housing while the housing is adhered to the skin of the host.

3. The device of claim 1, wherein the device is configured to disengage from the housing and from the electronics unit in response to the electronics unit being released from a lock.

4. The device of claim 1, wherein the device is configured to provide one or more tactile, auditory, or visual indications that the electronics unit has been inserted into the housing to the extent permitted by a lock.

5. The device of claim 1, further comprising a trigger lock configured to prevent activation of a trigger for the sensor insertion mechanism.

6. The device of claim 1, wherein the sensor is permanently connected to the conductive polymer contacts.

7. The device of claim 1, wherein the electronics unit and the sensor are integral with the housing.

8. The device of claim 7, wherein the electronics unit, the sensor, and the housing are configured to be disposed together.

* * * * *